United States Patent
Wong et al.

(10) Patent No.: US 9,920,360 B2
(45) Date of Patent: Mar. 20, 2018

(54) SMALL RNA CAPTURE, DETECTION AND QUANTIFICATION

(71) Applicant: LIFE TECHNOLOGIES CORPORATION, Carlsbad, CA (US)

(72) Inventors: Linda Wong, San Bruno, CA (US); Caifu Chen, Palo Alto, CA (US); Yalei Wu, Foster City, CA (US); Shoulian Dong, Mountain View, CA (US); Chunmei Liu, Palo Alto, CA (US)

(73) Assignee: LIFE TECHNOLOGIES CORPORATION, Carlsbad, CA (US)

(*) Notice: Subject to any disclaimer, the term of this patent is extended or adjusted under 35 U.S.C. 154(b) by 0 days.

(21) Appl. No.: 14/233,711

(22) PCT Filed: Nov. 4, 2013

(86) PCT No.: PCT/US2013/068350
§ 371 (c)(1),
(2) Date: Jan. 17, 2014

(87) PCT Pub. No.: WO2014/071322
PCT Pub. Date: May 8, 2014

(65) Prior Publication Data
US 2015/0105275 A1  Apr. 16, 2015

Related U.S. Application Data

(60) Provisional application No. 61/721,968, filed on Nov. 2, 2012, provisional application No. 61/740,242, filed on Dec. 20, 2012.

(51) Int. Cl.
*C12Q 1/68* (2006.01)
*C12P 19/34* (2006.01)

(52) U.S. Cl.
CPC ............ *C12Q 1/6855* (2013.01); *C12P 19/34* (2013.01); *C12Q 1/686* (2013.01); *C12Q 1/6851* (2013.01);
(Continued)

(58) Field of Classification Search
USPC ....................................... 435/6.12, 91.1, 91.2
See application file for complete search history.

(56) References Cited

U.S. PATENT DOCUMENTS 5,770,365 A * 6/1998 Lane .................... C12Q 1/6834
                                                              435/6.1
6,706,476 B1 * 3/2004 Thirstrup ............... C07H 21/04
                                                              435/6.12
(Continued)

FOREIGN PATENT DOCUMENTS

WO  WO-2004/013354   2/2004
WO  WO-2007/127999  11/2007
(Continued)

OTHER PUBLICATIONS

Fu et al. Identification of human fetal liver miRNAs by a novel method. FEBS Letters 579:3849-3854 (2005).*
(Continued)

*Primary Examiner* — Samuel C Woolwine

(57) ABSTRACT

Methods, compositions and kits for capturing, detecting and quantifying mature small RNAs are provided herein. Embodiments of the methods comprise ligating 5' and 3' ligation adaptors to the 5' and 3' ends of the mature small RNAs, respectively, in the presence of 5' and 3' semi-degenerate ligation splints to generate a ligation product. Other embodiments comprise reverse transcribing polyadenylated mature small RNA with a universal reverse transcription primer and ligating an adaptor to the 3' end of the
(Continued)

Poly A tailing with oligo dT adaptor cDNA in the presence of a semi-degenerate ligation splint to generate a cDNA ligation product.

19 Claims, 19 Drawing Sheets

(52) U.S. Cl.
CPC ......... *C12Q 1/6858* (2013.01); *C12Q 1/6832* (2013.01); *C12Q 1/6848* (2013.01)

(56) References Cited

U.S. PATENT DOCUMENTS

| | | | |
|---|---|---|---|
| 2005/0272075 A1 | 12/2005 | Jacobsen et al. | |
| 2007/0020672 A1* | 1/2007 | Wittwer | C07D 413/06 435/6.11 |
| 2007/0031857 A1* | 2/2007 | Makarov | C12P 19/34 435/6.18 |
| 2007/0054287 A1* | 3/2007 | Bloch | C12Q 1/686 435/6.12 |
| 2007/0059752 A1* | 3/2007 | Cook | C12Q 1/6876 435/6.12 |
| 2007/0072208 A1* | 3/2007 | Drmanac | C12Q 1/682 435/5 |
| 2007/0111226 A1* | 5/2007 | Tan | C12Q 1/6851 435/6.14 |
| 2007/0117112 A1* | 5/2007 | Diener | C12N 9/1247 435/6.11 |
| 2008/0194416 A1* | 8/2008 | Chen | C12Q 1/6816 506/9 |
| 2008/0248469 A1 | 10/2008 | Spier | |
| 2010/0279305 A1* | 11/2010 | Kuersten | C12Q 1/6855 435/6.16 |
| 2012/0015823 A1* | 1/2012 | Bignell | C12Q 1/6874 506/2 |
| 2013/0045885 A1* | 2/2013 | Mohapatra | C12Q 1/6851 435/6.12 |
| 2014/0128291 A1* | 5/2014 | Gu | C12Q 1/6848 506/26 |
| 2014/0134614 A1 | 5/2014 | Dong et al. | |

FOREIGN PATENT DOCUMENTS

| | | |
|---|---|---|
| WO | WO-2008/045251 | 4/2008 |
| WO | WO-2008/097957 | 8/2008 |
| WO | WO-2011/100057 | 8/2011 |
| WO | WO-2014/071322 | 5/2014 |

OTHER PUBLICATIONS

Blewett, N. et al., "A quantitative assay for measuring mRNA decapping by splinted ligation reverse transcription polymerase chain reaction: qSL-RT-PCR", *RNA Journal*, vol. 17, No. 3, Cold Spring Harbor Laboratory Press, Mar. 2011, 535-543.

Huang, Y. et al., "The discovery approaches and detection methods of microRNAs", *Molecular Biology Reports*, vol. 38, No. 6, Nov. 25, 2010, 4125-4135.

Maroney, et al., "Direct detection of small RNAs using splinted ligation", *Nature Protocols*, vol. 3, No. 2, 2008, 279-287.

PCT/US2013/068335, "International Search Report", dated Jan. 23, 2014, 5 pages.

PCT/US2013/068350, "International Search Report", dated Feb. 24, 2014, 6 pages.

* cited by examiner

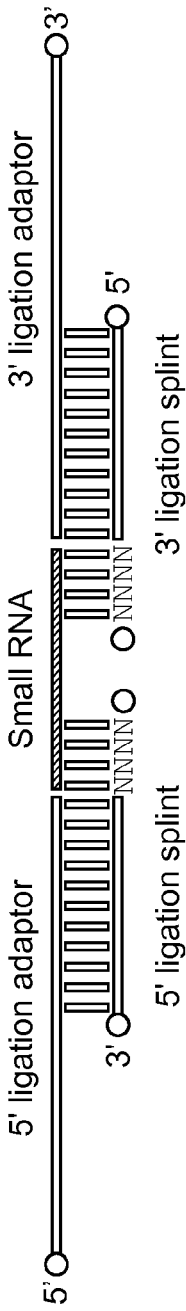
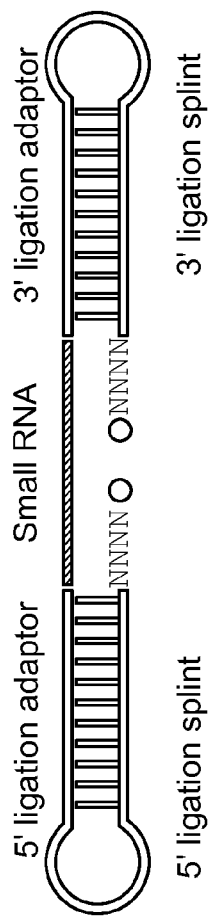
FIG. 3
FIG. 4

Background Blocking Strategies

A. MGB

B. STAR (Sequence Targeted Amplification Restrictive) URP/Blockers

C. 2-O-Methyl RNA

D. Poly(A) Stem-loop blocker

SEQUENCE LISTING

<160> NUMBER OF SEQ ID NOS: 2

<210> SEQ ID NO 1
<211> LENGTH: 22
<212> TYPE: RNA
<213> ORGANISM: Homo Sapien

<400> SEQUENCE: 1
ugagguagua gguugugugg uu          22

<210> SEQ ID NO 2
<211> LENGTH: 22
<212> TYPE: RNA
<213> ORGANISM: Homo Sapien

<400> SEQUENCE: 2
ugagguagua gguuguaugg uu          22

US 9,920,360 B2

SMALL RNA CAPTURE, DETECTION AND QUANTIFICATION

RELATED APPLICATIONS

This application is a U.S. National Application filed under 35 U.S.C. § 371 of International Application No. PCT/US2013/068350, filed Nov. 4, 2013, which claims priority to U.S. Provisional Patent Application No. 61/740,242, filed Dec. 20, 2012, and U.S. Provisional Patent Application No. 61/721,968, filed Nov. 2, 2012, the disclosures of which are hereby incorporated by reference in their entirety as if set forth fully herein.

FIELD

The present teachings are in the field of molecular and cell biology, specifically in the field of detecting target polynucleotides such as small RNA species.

INTRODUCTION

Small, non-coding, regulatory RNA species, such as microRNA (miRNA), are an abundant class of regulatory elements that have been shown to impact all aspects of normal cellular processes in both plants and animals, including cell death, differentiation, and proliferation. miRNAs have also been implicated in a number of diseases including cancer, heart disease and neurological diseases, consequently, miRNAs are studied as diagnostic and prognostic biomarkers. Small RNAs, including miRNAs, are generated by specific enzyme complexes from much larger RNA precursors. In general, a mature miRNA is composed of a highly conserved core sequence of 20-30 nucleotides and typically has a 5'-terminal monophosphate and a 3'-terminal hydroxyl group. miRNAs generally induce gene silencing by binding to target sites within the 3'-UTR of a targeted mRNA. This interaction suppresses protein synthesis and/or initiates mRNA degradation.

Attempts to detect, quantify and analyze mature small RNAs, such as miRNAs, have been hindered by several factors including their small sizes and similarity between related yet distinct species. Closely related miRNA family members can differ by only one nucleotide, thus there is a need for high specificity and the ability to discriminate between single nucleotide mismatches.

Nucleic acid microarrays have been used to quantify mature small RNAs, but this method requires a high concentration of input target for efficient hybridization. The small size of mature small RNAs precludes their amplification by quantitative or reverse transcriptase polymerase chain reaction (PCR), although the larger precursors may be amplified by PCR. Methods have been developed to facilitate PCR amplification of mature small RNAs. For example, mature small RNAs have been lengthened by the addition of at least one oligonucleotide adaptor. Alternatively, probes comprising a portion that hybridizes to a small RNA are ligated together and then used for PCR amplification. These methods are less than ideal because the ligation of single-stranded molecules is inefficient and/or the small RNA is not directly detected. Thus, a need still exists for a method of small RNA capture, detection and analysis that is improved over the prior art with respect to at least one of the following attributes: sensitivity, speed, efficiency and cost-effectiveness.

SUMMARY

Provided herein are methods, compositions and kits for the capture and detection of mature small RNAs. In certain embodiments, the present teachings provide a method for capturing, detecting and quantifying a mature small RNA, such as a microRNA (miRNA), from a sample using universal ligation adaptors on both the 5' and 3' ends of the mature small RNA by utilizing the 5'-terminal phosphate group and the 3' terminal hydroxyl group of a mature small RNA (see FIG. 1). Dual-end ligation of a ligation adaptor to each of the 5' end and 3' end of a mature small RNA is catalyzed by a template-dependent ligase in the presence of semi-degenerate ligation splints. The resulting ligation product comprises the mature small RNA, a universal 5' ligation adaptor and a universal 3' ligation adaptor and may be extended and amplified to directly detect and quantify the mature small RNA. After ligation, all mature small RNAs present in the sample that were modified by the ligation will comprise a universal sequence at both the 5' and 3' ends of the newly ligated regions allowing universal reverse transcription (RT) and universal pre-amplification (pre-amp) and/or amplification. Post-ligation digestion of ligation adaptors and ligation splints is optional but not required. In certain embodiments, the ligation, reverse transcription and pre-amplification and/or amplification steps may be performed together in a single reaction vessel (a 1-step or 3-in-1 method). In certain embodiments, the ligation and extension steps are performed together in a single reaction vessel (a 2-step method (1-step ligation/RT)). In certain embodiments, the reverse transcription and pre-amplification and/or amplification steps are performed together in a single reaction vessel (a 2-step method (1-step RT/pre-amp)).

In certain embodiments, the present teachings provide a method for capturing, detecting and quantifying a mature small RNA, such as a microRNA (miRNA), from a sample by polyadenylating and reverse transcribing the RNA with a universal reverse transcription primer to generate a cDNA with a universal primer portion at its 5' end, and ligating a universal ligation adaptor at the 3' end of the cDNA by utilizing the 5' terminal phosphate group on the adaptor and the 3' terminal hydroxyl group of cDNA (see FIG. 2). Ligation of a ligation adaptor to the 3' end of the cDNA is catalyzed by a ligase in the presence of a ligation splint that spans the ligation junction. The resulting ligation product comprises the cDNA of mature small RNA and a universal 3'-ligation adaptor, and comprises a universal sequence at both the 5' and 3' ends of the cDNA ligation product allowing universal pre-amplification (pre-amp) and/or amplification using a single pair of universal forward and reverse primers. In certain embodiments, the ligation splint is a semi-degenerate ligation splint. In certain embodiments, the sample may be a preparation of total RNA, a cellular extract, an intact cell, an in vitro transcription reaction, or a chemical synthesis. Post-ligation digestion of the ligation adaptor and ligation splint is optional but not required. In certain embodiments, the polyadenylation and reverse transcription steps may be performed together in a single reaction vessel (a 2-step method (1-step polyadenylation/RT)). In certain embodiments, the ligation and pre-amplification and/or amplification steps are performed together in a single reaction vessel (a 2-step method (1-step ligation/pre-amp)).

In certain embodiments, a blocking agent may be used. Detection of the target polynucleotides may be performed using amplification methods such as the polymerase chain reaction (PCR), such as quantitative real-time PCR, quantitative endpoint PCR, and standard PCR. In certain embodiments, the amplification methods comprise the use of activation by polyphosphorolysis (APP) reactions and polyphosphorolyzing agents. The 1-step and 2-step methods using universal RT and pre-amp/amplification that are provided herein, offer a simplified workflow that is highly desirable and improves detection, sensitivity and reproducibility.

By using universal 5' and 3' ligation adaptors, a single primer can be used as a universal reverse transcription primer (e.g., a universal RT/reverse primer) for the mature small RNA molecules in the sample that have been modified with ligation adaptors. Similarly, the universal primer pair can be used for pre-amplification and/or amplification (e.g., universal forward and universal RT/reverse primers) for the mature small RNA molecules in the sample that have been modified with ligation adaptors. By polyadenylating mature small RNA molecules, a single primer is used as a universal reverse transcription primer and is shared by all cDNA from the target polynucleotides in the sample. Similarly, a universal primer pair can be used for pre-amplification and/or amplification (e.g., universal forward and universal reverse primers) for the small RNA cDNA molecules that have been modified with a ligation adaptor.

The use of universal primers gives one or more of the following advantages: 1) allows for a single-plex reaction; 2) reduces target-specific biases; 3) eliminates fixed or custom pools; 4) eliminates target number restriction; 5) eliminates the need for design updates based on newly discovered mature small RNA species; 6) eliminates the need for pool development and validation; and 7) simplifies manufacturing since only one or two universal ligation adaptors and one set of universal primers are required. In addition, this system allows for increased flexibility for gene-specific primer design and probe design since the mature small RNA can be directly detected via assay methods such as PCR. Furthermore, the combined polyadenylation/universal RT (a 2-step method), combined ligation/universal pre-amp (a 2-step method), combined ligation/universal RT (a 2-step method), combined universal RT/universal pre-amp (a 2-step method) or combined ligation/universal RT/universal pre-amp (a 1-step or 3-in-1 method) methods provided herein provides the following advantages: 1) eliminates post-ligation digestion of the ligation adaptors and ligation splints; 2) simplifies the workflow; 3) decreases the time to results; 4) reduces the hands-on time; and 5) reduces the variation between assays.

In certain embodiments, the present teachings provide a method for detecting a target polynucleotide in a sample, the method including: ligating a universal 5' ligation adaptor to the 5' end of the target polynucleotide in the presence of a 5' semi-degenerate ligation splint that spans the 5' ligation junction, and ligating a universal 3' ligation adaptor to the 3' end of the target polynucleotide in the presence of a 3' semi-degenerate ligation splint that spans the 3' ligation junction, whereby a ligation product is formed; extending or reverse transcribing the ligation product to form an extension product using a universal RT/reverse primer; amplifying the extension product using a universal forward and RT/reverse primer pair to form an amplification product; and detecting the target polynucleotide. In certain embodiments, the target polynucleotide is a mature small RNA. In certain embodiments, the target polynucleotide is a miRNA. In certain embodiments, the sample may be an isolated preparation of total RNA, a cellular extract, an intact cell, an in vitro transcription reaction, or a chemical synthesis. In certain embodiments, the ligation, reverse transcription and pre-amplification and/or amplification steps are performed together or essentially concurrently in a single reaction vessel (a 1-step or 3-in-1 method). In certain embodiments, the ligation and reverse transcription steps are performed together or essentially concurrently in a single reaction vessel (a 2-step method (1-step ligation/RT)). In certain embodiments, the reverse transcription and pre-amplification and/or amplification steps are performed together or essentially concurrently in a single reaction vessel (a 2-step method (1-step RT/pre-amp)). In certain embodiments, a blocking oligonucleotide may be used. In certain embodiments, a blocking oligonucleotide may be used in the ligating step. In certain embodiments, a blocking oligonucleotide may be used in the reverse transcription step. In certain embodiments, a blocking oligonucleotide may be used in the amplification step. In certain embodiments, a blocking oligonucleotide may be used in the 1-step method. In certain embodiments, a blocking oligonucleotide may be used in the 2-step method. In certain embodiments, ligating the universal 5' ligation adaptor to the 5' end of the target polynucleotide is performed essentially concurrently with ligating the universal 3' ligation adaptor to the 3' end of the target polynucleotide. In certain embodiments, ligating the universal 5' ligation adaptor to the 5' end of the target polynucleotide is performed before ligating the universal 3' ligation adaptor to the 3' end of the target polynucleotide. In certain embodiments, ligating the universal 5' ligation adaptor to the 5' end of the target polynucleotide is performed after ligating the universal 3' ligation adaptor to the 3' end of the target polynucleotide. Detection of the target polynucleotides may be performed using amplification methods such as the polymerase chain reaction (PCR), such as quantitative real-time PCR, quantitative endpoint PCR, and standard PCR.

In certain embodiments, the present teachings provide a method for detecting a mature small RNA in a sample, the method including: ligating a universal 5' ligation adaptor to the 5' end of the mature small RNA in the presence of a 5' semi-degenerate ligation splint that spans the 5' ligation junction, and ligating a universal 3' ligation adaptor to the 3' end of the mature small RNA in the presence of a 3' semi-degenerate ligation splint that spans the 3' ligation junction, whereby a ligation product is formed; extending or reverse transcribing the ligation product to form an extension product using a universal RT/reverse primer; amplifying the extension product using a universal forward and RT/reverse primer pair to form an amplification product; and detecting the mature small RNA. In certain embodiments, the mature small RNA is a miRNA. In certain embodiments, the sample may be an isolated preparation of total RNA, a cellular extract, an intact cell, an in vitro transcription reaction, or a chemical synthesis. In certain embodiments, the ligation, reverse transcription and pre-amplification and/or amplification steps are performed together or essentially concurrently in a single reaction vessel (a 1-step or 3-in-1 method). In certain embodiments, the ligation and reverse transcription steps are performed together or essentially concurrently in a single reaction vessel (a 2-step method (1-step ligation/RT)). In certain embodiments, the reverse transcription and pre-amplification and/or amplification steps are performed together or essentially concurrently in a single reaction vessel (a 2-step method (1-step RT/pre-amp)). In certain embodiments, a blocking oligonucleotide may be used. In certain embodiments, a blocking oligonucleotide may be used in the ligating step. In certain embodiments, a blocking oligonucleotide may be used in the reverse transcription step. In certain embodiments, a blocking oligonucleotide may be used in the amplification step. In certain embodiments, a blocking oligonucleotide may be used in the 1-step method. In certain embodiments, a blocking oligonucleotide may be used in the 2-step method. In certain embodiments, ligating the universal 5' ligation adaptor to the 5' end of the mature small RNA is performed essentially concurrently with ligating the universal 3' ligation adaptor to the 3' end of the mature small RNA. In certain embodiments, ligating the universal 5' ligation adaptor to the 5' end of the mature small RNA is performed before ligating the universal 3' ligation adaptor to the 3' end of the mature small RNA. In certain embodiments, ligating the universal 5' ligation adaptor to the 5' end of the mature small RNA is performed after ligating the universal 3' ligation adaptor to the 3' end of the mature small RNA. Detection of the target polynucleotides may be performed using amplification methods such as the polymerase chain reaction (PCR), such as quantitative real-time PCR, quantitative endpoint PCR, and standard PCR.

In certain embodiments, the present teachings provide a method for detecting a microRNA (miRNA) in a sample, the method including: ligating a universal 5' ligation adaptor to the 5' end of the miRNA in the presence of a 5' semi-degenerate ligation splint that spans the 5' ligation junction, and ligating a universal 3' ligation adaptor to the 3' end of the miRNA in the presence of a 3' semi-degenerate ligation splint that spans the 3' ligation junction, whereby a ligation product is formed; extending or reverse transcribing the ligation product to form an extension product using a universal RT/reverse primer; amplifying the extension product using a universal primer pair to form an amplification product; and detecting the miRNA. In certain embodiments, the sample may be an isolated preparation of total RNA, a cellular extract, an intact cell, an in vitro transcription reaction, or a chemical synthesis. In certain embodiments, the ligation, reverse transcription and pre-amplification and/or amplification steps are performed together or essentially concurrently in a single reaction vessel (a 1-step or 3-in-1 method). In certain embodiments, the ligation and reverse transcription steps are performed together or essentially concurrently in a single reaction vessel (a 2-step method (1-step ligation/RT)). In certain embodiments, the reverse transcription and pre-amplification and/or amplification steps are performed together or essentially concurrently in a single reaction vessel (a 2-step method (1-step RT/pre-amp)). In certain embodiments, a blocking oligonucleotide may be used. In certain embodiments, a blocking oligonucleotide may be used in the ligating step. In certain embodiments, a blocking oligonucleotide may be used in the reverse transcription step. In certain embodiments, a blocking oligonucleotide may be used in the amplification step. In certain embodiments, a blocking oligonucleotide may be used in the 1-step method. In certain embodiments, a blocking oligonucleotide may be used in the 2-step method. In certain embodiments, ligating the universal 5' ligation adaptor to the 5' end of the miRNA is performed essentially concurrently with ligating the universal 3' ligation adaptor to the 3' end of the miRNA. In certain embodiments, ligating the universal 5' ligation adaptor to the 5' end of the miRNA is performed before ligating the universal 3' ligation adaptor to the 3' end of the miRNA. In certain embodiments, ligating the universal 5' ligation adaptor to the 5' end of the miRNA is performed after ligating the universal 3' ligation adaptor to the 3' end of the miRNA. Detection of the target polynucleotides may be performed using amplification methods such as the polymerase chain reaction (PCR), such as quantitative real-time PCR, quantitative endpoint PCR, and standard PCR.

In certain embodiments, the present teachings provide a method for detecting a mature small RNA in a sample, the method including: ligating a universal 5' ligation adaptor to the 5' end of the mature small RNA in the presence of a 5' semi-degenerate ligation splint that spans the 5' ligation junction, whereby a ligation product is formed; polyadenylating the 3' end of the mature small RNA; extending the ligation product to form an extension product using a universal poly(T) primer, wherein the universal poly(T) primer comprises a poly(T) portion and a tail portion, wherein the tail portion comprises a universal RT primer binding site (see FIG. 6); amplifying the extension product to form an amplification product; and detecting the mature small RNA. In certain embodiments, the mature small RNA is a miRNA. In certain embodiments, the polyadenylation step, extension step and amplification step are performed together in the same reaction vessel (a 1-step method). In certain embodiments, the polyadenylation and extension steps are performed together in a single reaction vessel (a 2-step method). In certain embodiments, the reverse transcription and pre-amplification and/or amplification steps are performed together in a single reaction vessel (a 2-step method (1-step RT/pre-amp)). In certain embodiments, the sample may be an isolated preparation of total RNA, a cellular extract, an intact cell, an in vitro transcription reaction, or a chemical synthesis. Detection of the target polynucleotides may be performed using amplification methods such as the polymerase chain reaction (PCR), such as quantitative real-time PCR, quantitative endpoint PCR, and standard PCR.

In certain embodiments, the present teachings provide a method for detecting a mature small RNA in a sample, the method including: polyadenylating the 3' end of the mature small RNA; reverse transcribing the polyadenylated RNA to form a cDNA using a universal reverse transcription (RT) primer (FIG. 2), wherein the universal RT primer comprises a poly(T) portion and a tail portion, the tail portion comprising a universal primer portion; ligating a universal ligation adaptor to the 3' end of the cDNA in the presence of a ligation splint that spans the ligation junction, whereby a cDNA ligation product is formed; amplifying the cDNA ligation product using a pair of universal forward and reverse primers and/or detecting the mature small RNA by PCR. In certain embodiments, the mature small RNA is a miRNA. In certain embodiments, the ligation splint is a semi-degenerate ligation splint. In certain embodiments, the sample may be an isolated preparation of total RNA, a cellular extract, an intact cell, an in vitro transcription reaction, or a chemical synthesis. In certain embodiments, the polyadenylation and reverse transcription steps are performed together or essentially concurrently in a single reaction vessel (a 2-step method (1-step polyadenylation/RT)). In certain embodiments, the ligation and pre-amplification steps are performed together or essentially concurrently in a single reaction vessel (a 2-step method (1-step ligation/pre-amp)). In certain embodiments a blocking oligonucleotide may be used. In certain embodiments, a blocking oligonucleotide may be used in the ligation step and/or the pre-amplification step. In certain embodiments, a blocking oligonucleotide may be used in the 1-step method. In certain embodiments, a blocking oligonucleotide may be used in the 2-step method. Detection of the target polynucleotides may be performed using amplification methods such as the polymerase chain reaction (PCR), such as quantitative real-time PCR, quantitative endpoint PCR, and standard PCR.

In certain embodiments, the 5' ligation adaptor and the 3' ligation adaptor are linear oligonucleotides (see FIG. 3). In certain embodiments, the 5' ligation adaptor comprises a 5' ligation splint complementary region at the 3' terminal region that is complementary to the 3' region of the 5' ligation splint and a universal forward primer binding site located at the 5' terminal region. The universal forward primer binding site in the 5' ligation adaptor is complementary to or includes the sequence of the universal forward primer. In certain embodiments, the 3' ligation adaptor comprises a blocking group at the 3' end, a 3' ligation splint complementary region at the 5' terminal region that is complementary to the 5' portion of the 3' ligation splint and a universal RT/reverse primer binding site located at the 3' terminal region. The universal RT/reverse primer binding site is complementary to the universal reverse primer. In certain embodiments, the 3' ligation adaptor is for ligation to the 3' end of cDNA and comprises a 3' ligation splint complementary region at the 5' terminal region that is complementary to the 5' portion of the 3' ligation splint and a universal primer binding site located at the 3' terminal region. In certain embodiments, the 3' ligation adaptor for ligation to the 3' end of cDNA comprises a blocking group at the 3' end, a 3' ligation splint complementary region at the 5' terminal region that is complementary to the 5' portion of the 3' ligation splint, and a universal forward primer binding site located at the 3' terminal region. The universal forward primer binding site is complementary to the universal forward primer. In certain embodiments, the 5' ligation adaptor is an RNA oligonucleotide and the 3' ligation adaptor is a DNA oligonucleotide.

In certain embodiments, the 5' semi-degenerate ligation splint comprises two distinct regions (see FIG. 3): a 5' terminal region containing degenerate nucleotide bases ranging from about 3 nucleotides to about 6 nucleotides that hybridize with the 5' end of the mature small RNA and a 3' region that hybridizes with the 3' end of the 5' ligation adaptor. In certain embodiments, the 5' semi-degenerate ligation splint comprises two distinct regions: a 5' terminal region containing from about 3 nucleotides to about 6 nucleotides that hybridize with the 5' end of the mature small RNA and a 3' region that hybridizes with the 3' end of the 5' ligation adaptor. In certain embodiments, the 3' ligation splint comprises two distinct regions: a 3' terminal region that contains degenerate nucleotide bases ranging from about 3 nucleotides to about 6 nucleotides that hybridize with the 3' end of the mature small RNA and a 5' region that hybridizes with the 5' end of the 3' ligation adaptor. In certain embodiments, the 3' ligation splint comprises two distinct regions: a 3' terminal region that contains from about 3 nucleotides to about 6 nucleotides that hybridize with the 3' end of the cDNA of the mature small RNA and a 5' region that hybridizes with the 5' end of the 3' ligation adaptor. In certain embodiments, the 3' ligation splint comprises two distinct regions: a 3' terminal region that contains degenerate nucleotide bases ranging from about 3 nucleotides to about 6 nucleotides that hybridize with the 3' end of the cDNA of the mature small RNA and a 5' region that hybridizes with the 5' end of the 3' ligation adaptor.

In certain embodiments, the 5' ligation adaptor and 3' ligation adaptor contain a stem-loop structure (herein referred to as "5' or 3' stem-loop ligation adaptors") (see FIG. 4), wherein the 5' stem-loop ligation adaptor comprises a 5' single-stranded overhang, a stem and a loop, wherein the 3' end of the stem portion is ligated to the 5' end of the mature small RNA and the 5' single-stranded overhang comprises 3 to 6 degenerate bases which hybridize with the 5' terminal portion of the mature small RNA and which serves as a ligation splint. In certain embodiments, the 3' stem-loop ligation adaptor comprises a 3' single-stranded overhang, a stem and a loop, wherein the 5' end of the stem portion is ligated to the 3' end of the mature small RNA and the 3' single-stranded overhang comprises 3 to 6 degenerate bases which hybridize with the 3' terminal region of the mature small RNA and which serves as a ligation splint. In certain embodiments, the 3' stem-loop ligation adaptor comprises a 3' single-stranded overhang, a stem and a loop, wherein the 5' end of the stem portion is ligated to the 3' end of the cDNA of a mature small RNA and the 3' single-stranded overhang comprises from about 3 to about 6 nucleotides which hybridize with the 3' terminal region of the cDNA and which serves as a ligation splint. In certain embodiments, 3' single-stranded overhang of this 3' stem-loop ligation adaptor comprises from about 3 to about 6 degenerate bases which hybridize with the 3' terminal region of the cDNA and which serves as a ligation splint.

In certain embodiments, both the 5' and 3' stem-loop ligation adaptors are DNA-RNA hybrid oligonucleotides. In certain embodiments, the 3' stem-loop ligation adaptor is a DNA oligonucleotide. In certain embodiments, the universal forward primer binding site is located in the stem portion of the 5' stem-loop ligation adaptor. In certain embodiments, the universal forward primer binding site is located in the loop portion of the 5' stem-loop ligation adaptor. In certain embodiments, the universal forward primer binding site is located in the stem and loop portions of the 5' stem-loop ligation adaptor. In certain embodiments, the universal RT/reverse primer binding site is located in the stem portion of the 3' stem-loop ligation adaptor. In certain embodiments, the universal RT/reverse primer binding site is located in the loop portion of the 3'-stem-loop ligation adaptor. In certain embodiments, the universal RT/reverse primer binding site is located in the stem and loop portions of the 3' stem-loop ligation adaptor. In certain embodiments, the universal forward primer binding site is located in the stem portion of the 3' stem-loop ligation adaptor. In certain embodiments, the universal forward primer binding site is located in the loop portion of the 3' stem-loop ligation adaptor. In certain embodiments, the universal forward primer binding site is located in the stem and loop portions of the 3'-stem-loop ligation adaptor.

In certain embodiments, the 5' ligation adaptor is a linear oligonucleotide and the 3' ligation adaptor is a stem-loop ligation adaptor (see FIG. 5). In certain embodiments, the 5' ligation adaptor is a stem-loop ligation adaptor and the 3' ligation adaptor is a linear oligonucleotide. In certain embodiments, the 3' ligation adaptor is a linear oligonucleotide and used for ligation to cDNA (see FIG. 2). In certain embodiments, the 3' ligation adaptor is a stem-loop ligation adaptor and used for ligation to cDNA.

In certain embodiments, the present teachings provide a kit for detecting a mature small RNA molecule, the kit comprising: a universal 5' ligation adaptor for ligating to the 5' end of the mature small RNA, a universal 3' ligation adaptor for ligating to the 3' end of the mature small RNA, a 5' semi-degenerate ligation splint that spans the 5' ligation junction, a 3' semi-degenerate ligation splint that spans the 3' ligation junction and instructions for using the kit. In certain embodiments, the kit further comprises one or more of a ligase, a reverse transcriptase and a DNA polymerase. In certain embodiments, the kit further comprises a universal RT/reverse primer and a universal forward primer. In certain embodiments, the 5' and 3' ligation adaptors are linear. In certain embodiments, the 5' and 3' ligation adaptors are stem-loop ligation adaptors. In certain embodiments, the kit further comprises a blocking oligonucleotide.

In certain embodiments, the present teachings provide a kit comprising a universal reverse transcription (RT) primer, a 3' ligation adaptor, and a 3' ligation splint, where the reverse transcription primer comprises a poly(T) portion and a tail portion comprises a universal primer portion. In certain embodiments, the kit further comprises one or more of a ligase, a reverse transcriptase and a DNA polymerase. In certain embodiments, the kit further comprises a universal reverse primer and a universal forward primer. In certain embodiments, the 3' ligation adaptor is linear. In certain embodiments, the 3' ligation adaptor is a stem-loop ligation adaptor. In certain embodiments, the kit further comprises a blocking oligonucleotide.

In certain embodiments, compositions, such as reaction compositions, are provided that comprise a universal 5' ligation adaptor, a universal 3' ligation adaptor, a 5' semi-degenerate ligation splint and a 3' semi-degenerate ligation splint. In certain embodiments, compositions are provided that further comprise a blocking oligonucleotide and/or a universal forward and RT/reverse primer pair. In certain embodiments, compositions are provided that comprise a universal reverse transcription primer comprising a poly(T) portion and a tail portion comprising a universal primer portion, a universal 3' ligation adaptor, and a 3' ligation splint. In certain embodiments, compositions are provided that further comprise a blocking oligonucleotide and/or a universal forward and reverse primer pair.

In certain embodiments, compositions are provided that comprise a blocking oligonucleotide to block the ligation adaptor self-ligated by-product or adaptor-primer ligated by-product formation and/or amplification (see FIG. 15). In certain embodiments, the blocking oligonucleotide is DNA. In certain embodiments, the blocking oligonucleotide is RNA. In certain embodiments, the blocking oligonucleotide comprises a poly(A) portion. In certain embodiments, the blocking oligonucleotide comprises a blocking agent, including, but not limited to, 2'-O-methyl, acridine, a minor groove binder (MGB), and an intercalating dye compound. In certain embodiments, the blocking agent is located at the 3' end of the blocking oligonucleotide. In certain embodiments, the blocking agent is located at the 5' end of the blocking oligonucleotide.

Certain embodiments provide for the use of any of the methods disclosed herein for the diagnosis and/or prognosis of diseases, for example, cancer, including but not limited to breast cancer, prostate cancer, lung cancer, skin cancer, cancers of the reproductive tract, brain cancer, liver cancer, pancreatic cancer, stomach cancer, blood cancers (e.g., leukemia and lymphoma), sarcomas, melanomas, and the like; cardiovascular diseases; autoimmune diseases and disorders; and metabolic diseases and disorders. Another embodiment provides for the use of any of the methods disclosed herein in the diagnosis or determination of responsiveness to drugs and medical treatment.

Other embodiments and illustrative aspects, features and advantages of the present disclosure will become apparent from the following detailed description. It should be understood that the detailed description and the specific examples, while indicating preferred embodiments, are given by way of illustration only, since various changes and modifications within the spirit and scope of the present disclosure will become apparent to those skilled in the art from this detailed description.

BRIEF DESCRIPTION OF THE DRAWINGS

The skilled artisan will understand that the drawings described below, are for illustration purposes only. The drawings are not intended to limit the scope of the present teachings in any way.

FIG. 3 schematically depicts linear ligation adaptors in accordance with one of the embodiments of the present teachings.

FIG. 4 schematically depicts stem-loop ligation adaptors in accordance with one of the embodiments of the present teachings.

DESCRIPTION OF EXEMPLARY EMBODIMENTS

Figure 1:
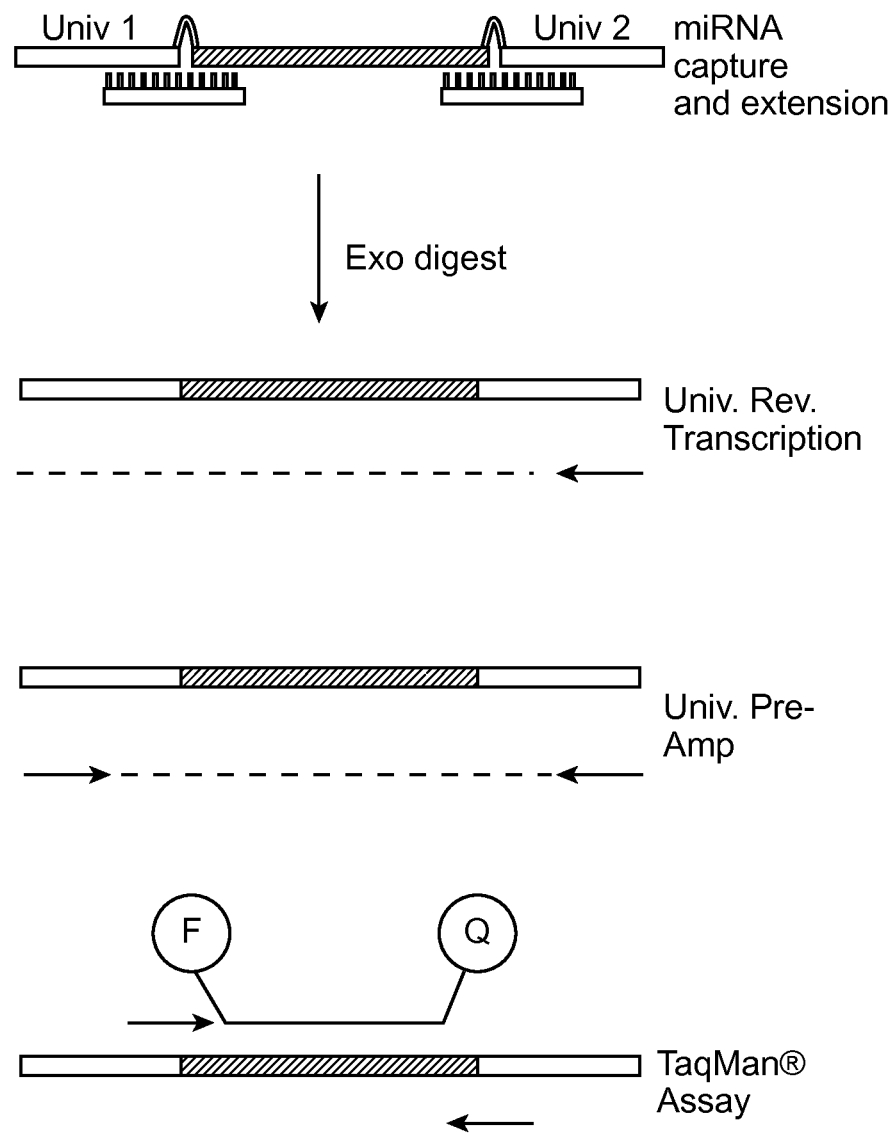
FIG. 1 schematically depicts the workflow for a dual-end ligation small RNA assay in accordance with one of the embodiments of the present teachings.

Provided herein are methods, compositions and kits for the capture and detection of mature small RNAs. In certain embodiments, the present teachings provide a method for capturing, detecting and quantifying a mature small RNA, such as a microRNA (miRNA), from a sample using universal ligation adaptors on both the 5' and 3' ends of the mature small RNA by utilizing the 5' terminal phosphate group and the 3' terminal hydroxyl group of a mature small RNA (see FIG. 1). Dual-end ligation of a ligation adaptor to each of the 5' end and 3' end of a mature small RNA is catalyzed by a template-dependent ligase in the presence of 5' and 3' semi-degenerate ligation splints. The resulting ligation product comprises the mature small RNA, a universal 5' ligation adaptor and a universal 3'-ligation adaptor and may be extended and amplified to directly detect and quantify the mature small RNA. After ligation, all mature small RNAs present in the sample that were modified by the ligation will comprise a universal sequence at both the 5' and 3' ends of the newly ligated regions allowing universal reverse transcription (RT) and universal pre-amplification (pre-amp) and/or amplification. In certain embodiments, the sample may be a preparation of total RNA, a cellular extract, an intact cell, an in vitro transcription reaction, or a chemical synthesis. Post-ligation digestion of ligation adaptors and ligation splints is optional but not required. In certain embodiments, the ligation, reverse transcription and pre-amplification and/or amplification steps may be performed together in a single reaction vessel (a 1-step or 3-in-1 method). In certain embodiments, the ligation and extension steps are performed together in a single reaction vessel (a 2-step method (1-step ligation/RT)). In certain embodiments, the reverse transcription and pre-amplification and/or amplification steps are performed together in a single reaction vessel (a 2-step method (1-step RT/pre-amp)).

Figure 2:
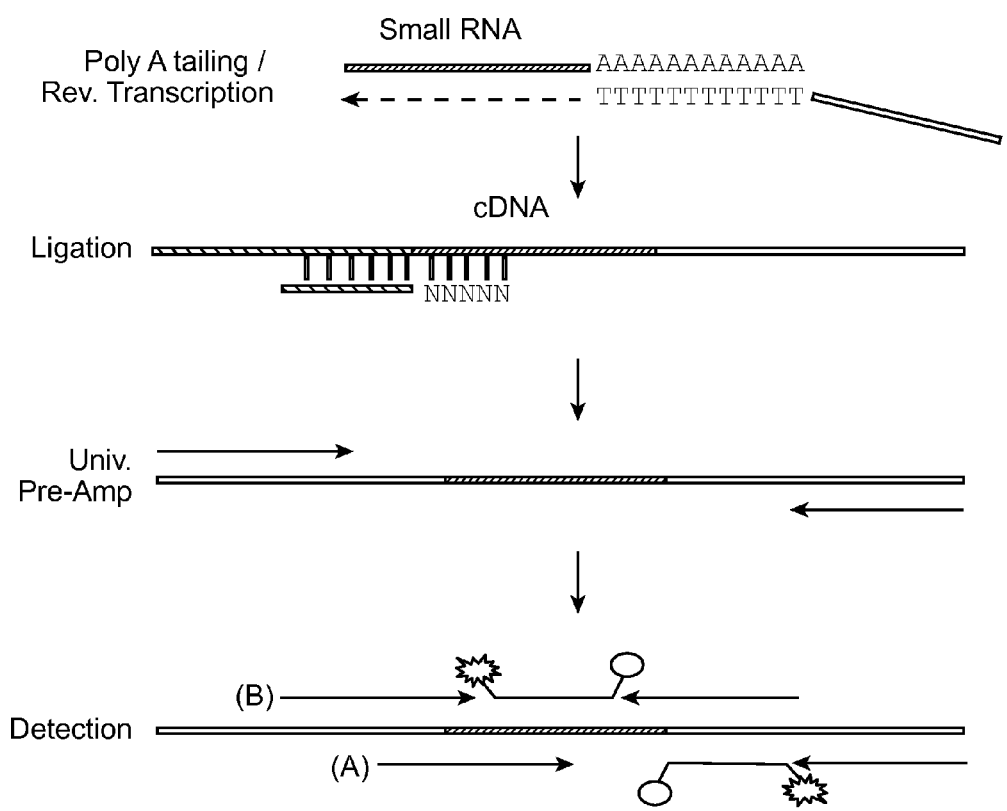
FIG. 2 schematically depicts the workflow for a two-ended small RNA extension assay in accordance with one of the embodiments of the present teachings.

In certain embodiments, the present teachings provide a method for capturing, detecting and quantifying a mature small RNA, such as a microRNA (miRNA), from a sample by polyadenylating and reverse transcribing the RNA with a universal reverse transcription primer to generate a cDNA with a universal primer portion at its 5' end, and ligating a universal ligation adaptor at the 3' end of the cDNA by utilizing the 5' terminal phosphate group on the adaptor and the 3' terminal hydroxyl group of cDNA (see FIG. 2). Ligation of a ligation adaptor to the 3' end of the cDNA is catalyzed by a template-dependent ligase in the presence of a ligation splint that spans the ligation junction. The resulting ligation product comprises the cDNA of mature small RNA and a universal 3'-ligation adaptor, and comprises a universal sequence at both the 5' and 3' ends of the cDNA ligation product allowing universal pre-amplification (pre-amp) and/or amplification using a single pair of universal forward and reverse primers. In certain embodiments, the ligation splint is a semi-degenerate ligation splint. In certain embodiments, the sample may be a preparation of total RNA, a cellular extract, an intact cell, an in vitro transcription reaction, or a chemical synthesis. Post-ligation digestion of the ligation adaptor and ligation splint is optional but not required. In certain embodiments, the polyadenylation and reverse transcription steps may be performed together in a single reaction vessel (a 2-step method (1-step polyadenylation/RT)). In certain embodiments, the ligation and pre-amplification and/or amplification steps are performed together in a single reaction vessel (a 2-step method (1-step ligation/pre-amp)).

In certain embodiments, a blocking oligonucleotide may be used. In certain embodiments, a blocking oligonucleotide may be used in the ligation and/or pre-amplification steps. Detection of the target polynucleotides may be performed using amplification methods such as the polymerase chain reaction (PCR), such as quantitative real-time PCR, quantitative endpoint PCR, and standard PCR. The 1-step and 2-step methods using universal RT and pre-amp/amplification that are provided herein, offer a simplified workflow that is highly desirable and improves detection, sensitivity and reproducibility.

By using universal 5' and 3' ligation adaptors, a single primer is used as a universal reverse transcription primer (e.g., a universal reverse primer) and is shared by all mature small RNA molecules in the sample that have been modified with ligation adaptors. Similarly, the universal primer pair can be used for pre-amplification and/or amplification (e.g., universal forward and universal RT/reverse primers) for the mature small RNA molecules in the sample that have been modified with ligation adaptors. By polyadenylating mature small RNA molecules, a single primer comprising a poly(T) portion is used as a universal reverse transcription primer and is shared by all cDNA from the target polynucleotides in the sample. Similarly, a universal primer pair can be used for pre-amplification and/or amplification (e.g., universal forward and universal reverse primers) for the small RNA cDNA molecules that have been modified with a ligation adaptor.

The use of universal primers gives one or more of the following advantages: 1) allows for a single-plex reaction; 2) reduces target-specific biases; 3) eliminates fixed or custom pools; 4) eliminates target number restriction; 5) eliminates the need for design updates based on newly discovered mature small RNA species; 6) eliminates the need for pool development and validation; and 7) simplifies manufacturing since only one or two ligation adaptors and one set of universal primers are required. In addition, this system allows for increased flexibility for gene-specific primer design and probe design since the mature small RNA can be directly detected via assay methods such as PCR. Furthermore, the combined polyadenylation/universal RT (a 2-step method), combined ligation/universal pre-amp (a 2-step method), combined ligation/universal RT (a 2-step method), combined universal RT/universal pre-amp (a 2-step method) or combined ligation/universal RT/universal pre-amp (a 1-step or 3-in-1 method) methods provided herein provides the following advantages: 1) eliminates post-ligation digestion of the ligation adaptors and ligation splints; 2) simplifies the workflow; 3) decreases the time to results; 4) decreases the hands-on time; and 5) reduces the variation between assays.

In certain embodiments, the present teachings provide a method for detecting a target polynucleotide in a sample, the method including: ligating a universal 5' ligation adaptor to the 5' end of the target polynucleotide in the presence of a 5' semi-degenerate ligation splint that spans the 5' ligation junction, and ligating a universal 3' ligation adaptor to the 3' end of the target polynucleotide in the presence of a 3' semi-degenerate ligation splint that spans the 3' ligation junction, whereby a ligation product is formed; extending or reverse transcribing the ligation product to form an extension product using a universal RT/reverse primer; amplifying the extension product using a universal forward and RT/reverse primer pair to form an amplification product; and detecting the target polynucleotide. In certain embodiments, the target polynucleotide is a mature small RNA. In certain embodiments, the target polynucleotide is a miRNA. In certain embodiments, the sample may be an isolated preparation of total RNA, a cellular extract, an intact cell, an in vitro transcription reaction, or a chemical synthesis. In certain embodiments, the ligation, reverse transcription and pre-amplification and/or amplification steps are performed together or essentially concurrently in a single reaction vessel (a 1-step or 3-in-1 method). In certain embodiments, the ligation and reverse transcription steps are performed together or essentially concurrently in a single reaction vessel (a 2-step method (1-step ligation/RT)). In certain embodiments, the reverse transcription and pre-amplification and/or amplification steps are performed together or essentially concurrently in a single reaction vessel (a 2-step method (1-step RT/pre-amp)). In certain embodiments, a blocking oligonucleotide may be used. In certain embodiments, a blocking oligonucleotide may be used in the ligating step. In certain embodiments, a blocking oligonucleotide may be used in the reverse transcription step. In certain embodiments, a blocking oligonucleotide may be used in the amplification step. In certain embodiments, a blocking oligonucleotide may be used in the 1-step method. In certain embodiments, a blocking oligonucleotide may be used in the 2-step method. In certain embodiments, ligating the universal 5' ligation adaptor to the 5' end of the target polynucleotide is performed essentially concurrently with ligating the universal 3' ligation adaptor to the 3' end of the target polynucleotide. In certain embodiments, ligating the universal 5' ligation adaptor to the 5' end of the target polynucleotide is performed before ligating the universal 3' ligation adaptor to the 3' end of the target polynucleotide. In certain embodiments, ligating the universal 5' ligation adaptor to the 5' end of the target polynucleotide is performed after ligating the universal 3' ligation adaptor to the 3' end of the target polynucleotide. Detection of the target polynucleotides may be performed using amplification methods such as the polymerase chain reaction (PCR), such as quantitative real-time PCR, quantitative endpoint PCR, and standard PCR.

In certain embodiments, the present teachings provide a method for detecting a mature small RNA from a sample, the method including: ligating a universal 5' ligation adaptor to the 5' end of the mature small RNA in the presence of a 5' semi-degenerate ligation splint that spans the 5' ligation junction, and ligating a universal 3' ligation adaptor to the 3' end of the mature small RNA in the presence of a 3' semi-degenerate ligation splint that spans the 3' ligation junction, whereby a ligation product is formed; extending or reverse transcribing the ligation product to form an extension product using a universal RT/reverse primer; amplifying the extension product using a universal forward and RT/reverse primer pair to form an amplification product; and detecting the mature small RNA. In certain embodiments, the mature small RNA is a miRNA. In certain embodiments, the sample may be an isolated preparation of total RNA, a cellular extract, an intact cell, an in vitro transcription reaction, or a chemical synthesis. In certain embodiments, the ligation, reverse transcription and pre-amplification and/or amplification steps are performed together in a single reaction vessel (a 1-step or 3-in-1 method). In certain embodiments, the ligation and reverse transcription steps are performed together or essentially concurrently in a single reaction vessel (a 2-step method (1-step ligation/RT)). In certain embodiments, the reverse transcription and pre-amplification and/or amplification steps are performed together or essentially concurrently in a single reaction vessel (a 2-step method (1-step RT/pre-amp)). In certain embodiments, a blocking oligonucleotide may be used. In certain embodiments, a blocking oligonucleotide may be used in the ligating step. In certain embodiments, a blocking oligonucleotide may be used in the reverse transcription step. In certain embodiments, a blocking oligonucleotide may be used in the amplification step. In certain embodiments, a blocking oligonucleotide may be used in the 1-step method. In certain embodiments, a blocking oligonucleotide may be used in the 2-step method. In certain embodiments, ligating the universal 5' ligation adaptor to the 5' end of the mature small RNA is performed essentially concurrently with ligating the universal 3' ligation adaptor to the 3' end of the mature small RNA. In certain embodiments, ligating the universal 5' ligation adaptor to the 5' end of the mature small RNA is performed before ligating the universal 3' ligation adaptor to the 3' end of the mature small RNA. In certain embodiments, ligating the universal 5' ligation adaptor to the 5' end of the mature small RNA is performed after ligating the universal 3' ligation adaptor to the 3' end of the mature small RNA. Detection of the target polynucleotides may be performed using amplification methods such as the polymerase chain reaction (PCR), such as quantitative real-time PCR, quantitative endpoint PCR, and standard PCR.

In certain embodiments, the present teachings provide a method for detecting a microRNA (miRNA) in a sample, the method including: ligating a universal 5' ligation adaptor to the 5' end of the miRNA in the presence of a 5'-semi-degenerate ligation splint that spans the 5' ligation junction, and ligating a universal 3' ligation adaptor to the 3' end of the miRNA in the presence of a 3' semi-degenerate ligation splint that spans the 3' ligation junction, whereby a ligation product is formed; extending or reverse transcribing the ligation product to form an extension product using a universal RT/reverse primer; amplifying the extension product using a universal forward and RT/reverse primer pair to form an amplification product; and detecting the miRNA. In certain embodiments, the sample may be an isolated preparation of total RNA, a cellular extract, an intact cell, an in vitro transcription reaction, or a chemical synthesis. In certain embodiments, the ligation, reverse transcription and pre-amplification and/or amplification steps are performed together or essentially concurrently in a single reaction vessel (a 1-step or 3-in-1 method). In certain embodiments, the ligation and reverse transcription steps are performed together or essentially concurrently in a single reaction vessel (a 2-step method (1-step ligation/RT)). In certain embodiments, the reverse transcription and pre-amplification and/or amplification steps are performed together or essentially concurrently in a single reaction vessel (a 2-step method (1-step RT/pre-amp)). In certain embodiments, a blocking oligonucleotide may be used. In certain embodiments, a blocking oligonucleotide may be used in the ligating step. In certain embodiments, a blocking oligonucleotide may be used in the reverse transcription step. In certain embodiments, a blocking oligonucleotide may be used in the amplification step. In certain embodiments, a blocking oligonucleotide may be used in the 1-step method. In certain embodiments, a blocking oligonucleotide may be used in the 2-step method. In certain embodiments, ligating the universal 5' ligation adaptor to the 5' end of the miRNA is performed essentially concurrently with ligating the universal 3' ligation adaptor to the 3' end of the miRNA. In certain embodiments, ligating the universal 5' ligation adaptor to the 5' end of the miRNA is performed before ligating the universal 3' ligation adaptor to the 3' end of the miRNA. In certain embodiments, ligating the universal 5' ligation adaptor to the 5' end of the miRNA is performed after ligating the universal 3' ligation adaptor to the 3' end of the miRNA. Detection of the target polynucleotides may be performed using amplification methods such as the polymerase chain reaction (PCR), such as quantitative real-time PCR, quantitative endpoint PCR, and standard PCR.

Figure 6:
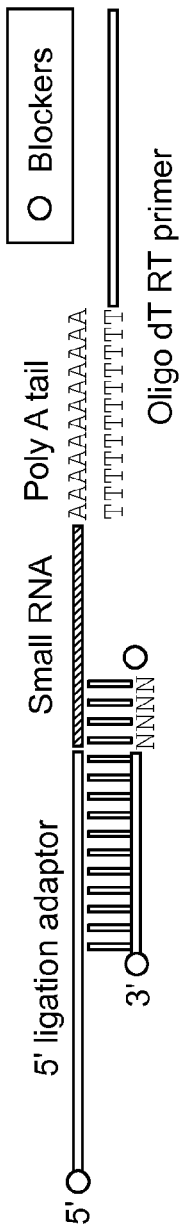
FIG. 6 schematically depicts poly(A) tailing with an oligo-dT primer in accordance with one of the embodiments of the present teachings.

In certain embodiments, the present teachings provide a method for detecting a mature small RNA in a sample, the method including: ligating a universal 5' ligation adaptor to the 5' end of the mature small RNA in the presence of a 5' semi-degenerate ligation splint that spans the 5' ligation junction, whereby a ligation product is formed; polyadenylating the 3' end of the mature small RNA; extending the ligation product to form an extension product using a universal poly(T) primer, wherein the universal poly(T) primer comprises a poly(T) portion and a tail portion, wherein the tail portion comprises a universal RT primer binding site (see FIG. 6); amplifying the extension product to form an amplification product; and detecting the mature small RNA. In certain embodiments, the mature small RNA is a miRNA. In certain embodiments, the sample may be an isolated preparation of total RNA, a cellular extract, an intact cell, an in vitro transcription reaction, or a chemical synthesis. In certain embodiments, the polyadenylation step, extension step and amplification step are performed together in the same reaction vessel (a 1-step method). In certain embodiments, the polyadenylation step and extension step are performed together in the same reaction vessel (a 2-step method). In certain embodiments, the extension step and the amplification step are performed together in the same reaction vessel (a 2-step method (1-step RT/pre-amp)). Detection of the target polynucleotides may be performed using amplification methods such as the polymerase chain reaction (PCR), such as quantitative real-time PCR, quantitative endpoint PCR, and standard PCR.

In certain embodiments, the present teachings provide a method for detecting a mature small RNA in a sample, the method including: polyadenylating the 3' end of the small mature RNA; reverse transcribing the polyadenylated RNA to form a cDNA using a universal reverse transcription (RT) primer (FIG. 2), wherein the universal RT primer comprises a poly(T) portion and a tail portion, the tail portion comprising a universal primer portion; ligating a universal ligation adaptor to the 3' end of the cDNA in the presence of a ligation splint that spans the ligation junction, whereby a cDNA ligation product is formed; amplifying the cDNA ligation product using a pair of universal forward and reverse primers and/or detecting the mature small RNA by PCR. In certain embodiments, the mature small RNA is a miRNA. In certain embodiments, the ligation splint is a semi-degenerate ligation splint. In certain embodiments, the sample may be an isolated preparation of total RNA, a cellular extract, an intact cell, an in vitro transcription reaction, or a chemical synthesis. In certain embodiments, the polyadenylation and reverse transcription steps are performed together or essentially concurrently in a single reaction vessel (a 2-step method (1-step polyadenylation/RT)). In certain embodiments, the ligation and pre-amplification steps are performed together or essentially concurrently in a single reaction vessel (a 2-step method (1-step ligation/pre-amp)). In certain embodiments a blocking oligonucleotide may be used. In certain embodiments, a blocking oligonucleotide may be used in the ligation step and/or the pre-amplification step. In certain embodiments, a blocking oligonucleotide may be used in the 1-step method. In certain embodiments, a blocking oligonucleotide may be used in the 2-step method. Detection of the target polynucleotides may be performed using amplification methods such as the polymerase chain reaction (PCR), such as quantitative real-time PCR, quantitative endpoint PCR, and standard PCR.

In certain embodiments, the 5' ligation adaptor and the 3' ligation adaptor are linear oligonucleotides (see FIG. 3). In certain embodiments, the 5' ligation adaptor comprises a 5' ligation splint complementary region at the 3' terminal region that is complementary to the 3' region of the 5' ligation splint and a universal forward primer binding site located at the 5' terminal region. The universal forward primer binding site in the 5' ligation adaptor is complementary to or includes the sequence of the universal forward primer. In certain embodiments, the 3' ligation adaptor comprises a blocking group at the 3' end, a 3' ligation splint complementary region at the 5' terminal region that is complementary to the 5' portion of the 3' ligation splint and a universal RT/reverse primer binding site located at the 3' terminal region. The universal RT/reverse primer binding site is complementary to the universal reverse primer. In certain embodiments, the 3' ligation adaptor is for ligation to the 3' end of cDNA and comprises a 3' ligation splint complementary region at the 5' terminal region that is complementary to the 5' portion of the 3' ligation splint and a universal primer binding site located at the 3' terminal region. In certain embodiments, the 3' ligation adaptor is for ligation to the 3' end of cDNA and comprises a blocking group at the 3' end, a 3' ligation splint complementary region at the 5' terminal region that is complementary to the 5' portion of the 3' ligation splint and a universal forward primer binding site located at the 3' terminal region. The universal forward primer binding site is complementary to the universal forward primer. In certain embodiments, the 5' ligation adaptor is an RNA oligonucleotide and the 3' ligation adaptor is a DNA oligonucleotide.

In certain embodiments, the 5' semi-degenerate ligation splint comprises two distinct regions (see FIG. 3): a 5' terminal region containing degenerate nucleotide bases ranging from about 3 nucleotides to about 6 nucleotides that hybridize with the 5' end of the mature small RNA and a 3' region that hybridizes with the 3' end of the 5' ligation adaptor. In certain embodiments, the 3' ligation splint comprises two distinct regions: a 3' terminal region that contains degenerate nucleotide bases ranging from about 3 nucleotides to about 6 nucleotides that hybridize with the 3' end of the mature small RNA and a 5' region that hybridizes with the 5' end of the 3' ligation adaptor. In certain embodiments, the 3' ligation splint comprises two distinct regions: a 3' terminal region that contains from about 3 nucleotides to about 6 nucleotides that hybridize with the 3' end of the cDNA of the mature small RNA and a 5' region that hybridizes with the 5' end of the 3' ligation adaptor. In certain embodiments, the 3' ligation splint comprises two distinct regions: a 3' terminal region that contains degenerate nucleotide bases ranging from about 3 nucleotides to about 6 nucleotides that hybridize with the 3' end of the cDNA of the mature small RNA and a 5' region that hybridizes with the 5' end of the 3' ligation adaptor.

In certain embodiments, the 5' ligation adaptor and 3'-ligation adaptor contain a stem-loop structure (herein referred to as "5' or 3' stem-loop ligation adaptors") (see FIG. 4), wherein the 5' stem-loop ligation adaptor comprises a 5' single-stranded overhang, a stem and a loop, wherein the 3' end of the stem portion is ligated to the 5' end of the mature small RNA and the 5' single-stranded overhang comprises 3 to 6 degenerate bases which hybridize with the 5' terminal region of the mature small RNA and which serves as a ligation splint. In certain embodiments, the 3' stem-loop ligation adaptor comprises a 3' single-stranded overhang, a stem and a loop, wherein the 5' end of the stem portion is ligated to the 3' end of the mature small RNA and the 3' single-stranded overhang comprises 3 to 6 degenerate bases which hybridize with the 3' terminal region of the mature small RNA and which serves as a ligation splint. In certain embodiments, the 3' stem-loop ligation adaptor comprises a 3' single-stranded overhang, a stem and a loop, wherein the 5' end of the stem portion is ligated to the 3' end of the cDNA of a mature small RNA and the 3' single-stranded overhang comprises from about 3 to about 6 nucleotides which hybridize with the 3' terminal region of the cDNA and which serves as a ligation splint. In certain embodiments, 3' single-stranded overhang of this 3' stem-loop ligation adaptor comprises from about 3 to about 6 degenerate bases which hybridize with the 3' terminal region of the cDNA and which serves as a ligation splint.

In certain embodiments, the ligation splints and the ligation adaptors may comprise natural nucleotide bases (e.g, A, C, G, T, U) or degenerate nucleotide bases in regions designed to hybridize with the mature small RNAs or cDNAs thereof. The semi-degenerate ligation splints and the ligation adaptors may comprise natural nucleotide bases and degenerate nucleotide bases in regions designed to hybridize with the mature small RNAs or cDNAs thereof. In certain embodiments, the ligation splints and adaptors comprise a terminal region that contains from about 2 to about 13 nucleotide bases that hybridize to the 3' or 5' end of the mature small RNA or to the 3' end of the cDNA of the mature small RNA. In certain embodiments, such terminal regions of the ligation splints and adaptors comprise about 3 to about 10 nucleotides, about 3 to about 8 nucleotides, or about 3 to about 6 nucleotides that hybridize to the mature small RNA or cDNA thereof. In certain embodiments, the ligation splints and adaptors comprise a terminal region that contains from about 3 to about 6 degenerate nucleotide bases that hybridize to the 3' or 5' end of the mature small RNA or to the 3' end of the cDNA of the mature small RNA. In certain embodiments, the ligation splints and adaptors comprise a terminal region that contains about 6 degenerate nucleotide bases. In certain embodiments, the ligation splints and adaptors comprise a terminal region that contains about 5 degenerate nucleotide bases. In certain embodiments, the ligation splints and adaptors comprise a terminal region that contains about 4 degenerate nucleotide bases. In certain embodiments, the ligation splints and adaptors comprise a terminal region that contains about 3 degenerate nucleotide bases. In certain embodiments, the degenerate nucleotide bases of the ligation splints and adaptors are selected from the group consisting of deoxyinosine, 5-nitroindole, and 2-amino purine. In particular embodiments, the degenerate nucleotide bases of the ligation splints and adaptors are deoxyinosine.

In certain embodiments, both the 5' and 3' stem-loop ligation adaptors are DNA-RNA hybrid oligonucleotides. In certain embodiments, the 3' stem-loop ligation adaptor is a DNA oligonucleotide. In certain embodiments, the universal primer binding site is located in the stem portion of the 5' stem-loop ligation adaptor. In certain embodiments, the universal forward primer binding site is located in the loop portion of the 5' stem-loop ligation adaptor. In certain embodiments, the universal forward primer binding site is located in the stem and loop portions of the 5' stem-loop ligation adaptor. In certain embodiments, the universal RT/reverse primer binding site is located in the stem portion of the 3' stem-loop ligation adaptor. In certain embodiments, the universal RT/reverse primer binding site is located in the loop portion of the 3' stem-loop ligation adaptor. In certain embodiments, the universal RT/reverse primer binding site is located in the stem and loop portions of the 3'-stem-loop ligation adaptor. In certain embodiments, the universal forward primer binding site is located in the stem portion of the 3' stem-loop ligation adaptor. In certain embodiments, the universal forward primer binding site is located in the loop portion of the 3' stem-loop ligation adaptor. In certain embodiments, the universal forward primer binding site is located in the stem and loop portions of the 3'-stem-loop ligation adaptor.

Figure 5:
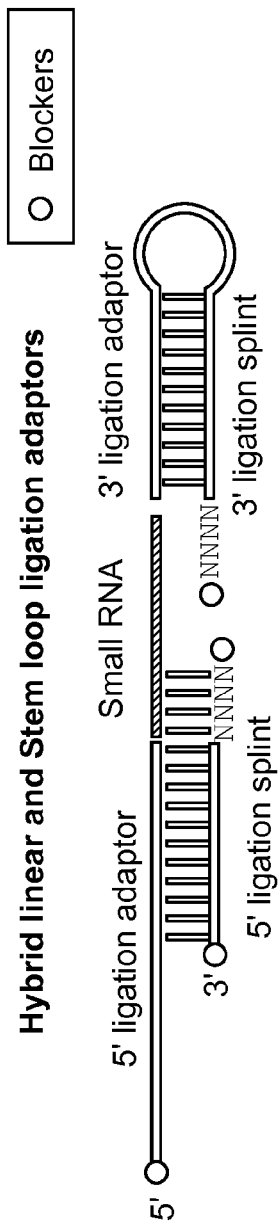
FIG. 5 schematically depicts a combination of a linear ligation adaptor and a stem-loop ligation adaptor in accordance with one of the embodiments of the present teachings.

In certain embodiments, the 5' ligation adaptor is a linear oligonucleotide and the 3' ligation adaptor is a stem-loop ligation adaptor (see FIG. 5). In certain embodiments, the 5' ligation adaptor is a stem-loop ligation adaptor and the 3' ligation adaptor is a linear oligonucleotide. In certain embodiments, the 3' ligation adaptor is a linear oligonucleotide and used for ligation to cDNA (see FIG. 2). In certain embodiments, the 3' ligation adaptor is a stem-loop ligation adaptor and used for ligation to cDNA.

Figure 15:
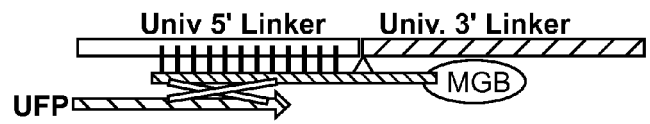
FIG. 15 schematically represents four strategies to block background adaptor-adaptor or adaptor-primer ligation by-product using: A) a blocking oligonucleotide that has a MGB molecule bound to its 3' end, b) a sequence targeted amplification restrictive (STAR) URP blocking oligonucleotide, C) a blocking oligonucleotide that has a 2'-O-methyl group attached to its 5' end (in this embodiment, the blocking oligonucleotide is RNA), or D) a blocking oligonucleotide with a stem-loop structure and a poly(A) containing single-stranded overhang portion at its 3' end.
Figure 15:
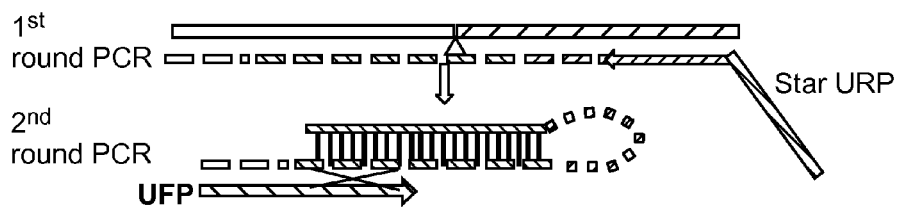
Figure 15:
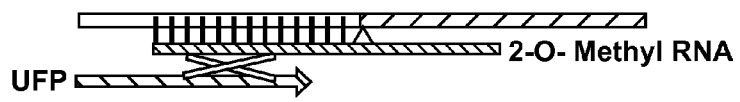
Figure 15:
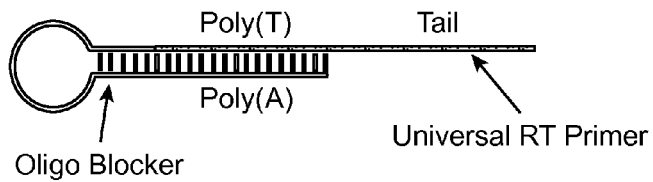

In certain embodiments, compositions are provided that comprise a blocking oligonucleotide to block the ligation adaptor self-ligated by-product or adaptor-primer ligated by-product formation and/or amplification (see FIG. 15). In certain embodiments, the blocking oligonucleotide is DNA. In certain embodiments, the blocking oligonucleotide is RNA. In certain embodiments, the blocking oligonucleotide comprises a poly(A) portion. In certain embodiments, the blocking oligonucleotide comprises a blocking agent, including, but not limited to, 2'-O-methyl, acridine, a minor groove binder (MGB), and an intercalating dye compound.

To more clearly and concisely describe and point out the subject matter of the present disclosure, the following definitions are provided for specific terms which are used in the following description and the appended claims. Throughout the specification, exemplification of specific terms should be considered as non-limiting examples.

As used in this specification, the words "a" or "an" means at least one, unless specifically stated otherwise. In this specification, the use of the singular includes the plural unless specifically stated otherwise. For example, but not as a limitation, "a target nucleic acid" means that more than one target nucleic acid can be present; for example, one or more copies of a particular target nucleic acid species, as well as two or more different species of target nucleic acid. The term "and/or" means that the terms before and after the slash can be taken together or separately. For illustration purposes, but not as a limitation, "X and/or Y" can mean "X" or "Y" or "X" and "Y".

It will be appreciated that there is an implied "about" prior to the temperatures, concentrations, times, etc. discussed in the present disclosure, such that slight and insubstantial deviations are within the scope of the present teachings herein. Also, the use of "comprise", "comprises", "comprising", "contain", "contains", "containing", "include", "includes", and "including" are not intended to be limiting. It is to be understood that both the foregoing general description and detailed description are exemplary and explanatory only and are not restrictive of the teachings.

Unless specifically noted in the above specification, embodiments in the above specification that recite "comprising" various components are also contemplated as "consisting of" or "consisting essentially of" the recited components; embodiments in the specification that recite "consisting of" various components are also contemplated as "comprising" or "consisting essentially of" the recited components; and embodiments in the specification that recite "consisting essentially of" various components are also contemplated as "consisting of" or "comprising" the recited components (this interchangeability does not apply to the use of these terms in the claims).

The term "or combinations thereof" as used herein refers to all permutations and combinations of the listed terms preceding the term. For example, "A, B, C, or combinations thereof" is intended to include at least one of: A, B, C, AB, AC, BC, or ABC, and if order is important in a particular context, also BA, CA, CB, ACB, CBA, BCA, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

The section headings used herein are for organizational purposes only and are not to be construed as limiting the desired subject matter in any way. All literature cited in the specification, including but not limited to, patent, patent applications, articles, books and treatises are expressly incorporated by reference in their entirety for any purpose. In the event that any of the incorporated literature contradicts any term defined in this specification, this specification controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

The term "hybridizing", including, without limitation, variations of the root words "hybridize", is used interchangeably and means the complementary nucleotide base-pairing interaction of one nucleic acid with another nucleic acid that results in the formation of a duplex, triplex, or other higher-ordered structure. The primary interaction is typically nucleotide base specific, e.g., A:T, A:U, and G:C, by Watson-Crick and Hoogsteen-type hydrogen bonding. In certain embodiments, base-stacking and hydrophobic interactions may also contribute to duplex stability. Conditions under which primers and probes anneal to complementary sequences are well known in the art, e.g., as described in Nucleic Acid Hybridization, A Practical Approach, Hames and Higgins, eds., IRL Press, Washington, D.C. (1985) and Wetmur and Davidson, Mol. Biol. 31:349 (1968).

In general, whether such annealing takes place is influenced by, among other things, the length of the polynucleotides and the complementarity, the pH, the temperature, the presence of mono- and divalent cations, the proportion of G and C nucleotides in the hybridizing region, the viscosity of the medium, and the presence of denaturants. Such variables influence the time required for hybridization. Thus, the preferred annealing conditions will depend upon the particular application. Such conditions, however, can be routinely determined by persons of ordinary skill in the art, without undue experimentation. It will be appreciated that complementarity need not be perfect; there can be a small number of base pair mismatches that will minimally interfere with hybridization between the target sequence and the single-stranded nucleic acids of the present teachings. However, if the number of base pair mismatches is so great that no hybridization can occur under minimally stringent conditions, then the sequence is generally not a complementary target sequence. Thus, "complementarity" herein is meant that the probes or primers are sufficiently complementary to the target sequence to hybridize under the selected reaction conditions to achieve the ends of the present teachings. Preferably, annealing conditions are selected to allow the primers and/or probes to selectively hybridize with a complementary sequence in the corresponding target flanking sequence or amplicon, but not hybridize to any significant degree to different target nucleic acids or non-target sequences in the reaction composition at the second reaction temperature.

The term "minor groove binder" or "MGB" as used herein refers to a small molecule that fits into the minor groove of double-stranded DNA, sometimes in a sequence specific manner. Generally, minor groove binders are long, flat molecules that can adopt a crescent-like shape and thus, fit snugly into the minor groove of a double helix, often displacing water. Minor groove binding molecules typically comprise several aromatic rings connected by bonds with torsional freedom, for example, but not limited to, furan, benzene, or pyrrole rings.

As used herein, the terms "polynucleotide", "oligonucleotide," and "nucleic acid" are used interchangeably and refer to single-stranded and double-stranded polymers of nucleotide monomers, including without limitation, 2'-deoxyribonucleotides (DNA) and ribonucleotides (RNA) linked by internucleotide phosphodiester bond linkages, or internucleotide analogs, and associated counter ions, e.g., H+, NH4+, trialkylammonium, Mg2+, Na+, and the like. A polynucleotide may be composed entirely of deoxyribonucleotides, entirely of ribonucleotides, or chimeric mixtures thereof and may include nucleotide analogs. The nucleotide monomer units may comprise any of the nucleotides described herein, including, but not limited to, nucleotides and/or nucleotide analogs. Polynucleotides typically range in size from a few monomeric units, e.g., 5-40 when they are sometimes referred to in the art as oligonucleotides, to several thousands of monomeric nucleotide units. Unless denoted otherwise, whenever a polynucleotide sequence is represented, it will be understood that the nucleotides are in the 5'-to-3' order from left to right and that "A" denotes deoxyadenosine, "C" denotes deoxycytosine, "G" denotes deoxyguanosine, "T" denotes deoxythymidine, and "U" denotes deoxyuridine, unless otherwise noted.

The term "nucleotide" refers to a phosphate ester of a nucleoside, e.g., triphosphate esters, wherein the most common site of esterification is the hydroxyl group attached at the C-5 position of the pentose.

The term "nucleoside" refers to a compound consisting of a purine, deazapurine, or pyrimidine nucleoside base, e.g., adenine, guanine, cytosine, uracil, thymine, deazaadenine, deazaguanosine, and the like, linked to a pentose at the 1'-position, including 2'-deoxy and 2'-hydroxyl forms. When the nucleoside base is purine or 7-deazapurine, the pentose is attached to the nucleobase at the 9-position of the purine or deazapurine, and when the nucleobase is pyrimidine, the pentose is attached to the nucleobase at the 1-position of the pyrimidine.

The term "degenerate" nucleotide or nucleoside base refers to the base's ability to pair indiscriminately with more than one base, for example, with all pyrimidines, with all purines or with any natural nucleotide. Typically, a degenerate base has the ability to replace any of the four natural bases without significantly destabilizing either neighboring base-pair interaction or disrupting the expected functional capability of the resulting modified oligonucleotide. Examples of degenerate bases include, but are not limited to deoxyinosine, iso-deoxyguanosine, 5-nitroindole, 5-methyl isodeoxycytosine, and 2-amino purine.

The term "analog" includes synthetic analogs having modified base moieties, modified sugar moieties, and/or modified phosphate ester moieties. Phosphate analogs generally comprise analogs of phosphate wherein the phosphorous atom is in the +5 oxidation state and one or more of the oxygen atoms is replaced with a non-oxygen moiety, e.g. sulfur. Exemplary phosphate analogs include: phosphorothioate, phosphorodithioate, phosphoroselenoate, phosphorodiselenoate, phosphoroanilothioate, phosphoranilidate, phosphoramidate, boronophosphates, including associated counterions, e.g., H+, NH4+, Na+. Exemplary base analogs include: 2,6-diaminopurine, hypoxanthine, pseudouridine, C-5-propyne, isocytosine, isoguanine, 2-thiopyrimidine. Exemplary sugar analogs include: 2'- or 3'-modifications where the 2'- or 3'-position is hydrogen, hydroxy, alkoxy, e.g., methoxy, ethoxy, allyloxy, isopropoxy, butoxy, isobutoxy and phenoxy, azido, amino or alkylamino, fluoro, chloro, and bromo.

As used herein, the term "target polynucleotide" refers to a polynucleotide sequence that is sought to be detected. The target polynucleotide may be obtained from any source, and may comprise any number of different compositional components. For example, the target may be a nucleic acid (e.g., DNA or RNA), transfer RNA (tRNA), small interfering RNA (siRNA), microRNA (miRNA), or other mature small RNA, and may comprise nucleic acid analogs or other nucleic acid mimics. The target may be methylated, non-methylated, or both. The target may be bisulfite-treated and non-methylated cytosines converted to uracil. Further, it will be appreciated that "target polynucleotide" may refer to the target polynucleotide itself, as well as surrogates thereof, for example, amplification products and native sequences. In certain embodiments, the target polynucleotide is a miRNA molecule. In certain embodiments, the target polynucleotide lacks a poly-A tail. In certain embodiments, the target polynucleotide is a mature small RNA molecule. The target polynucleotides of the present teachings may be derived from any number of sources, including without limitation, viruses, archae, protists, prokaryotes and eukaryotes, for example, but not limited to, plants, fungi, and animals. These sources may include, but are not limited to, whole blood, a tissue biopsy, lymph, bone marrow, amniotic fluid, hair, skin, semen, biowarfare agents, anal secretions, vaginal secretions, perspiration, saliva, buccal swabs, various environmental samples (for example, agricultural, water, and soil), research samples generally, purified samples generally, cultured cells and lysed cells. It will be appreciated that target polynucleotides may be isolated from samples using any of a variety of procedures known in the art, for example, the Applied Biosystems ABI Prism® 6100 Nucleic Acid PrepStation (Life Technologies, Foster City, Calif.) and the ABI Prism® 6700 Automated Nucleic Acid Workstation (Life Technologies, Foster City, Calif.), Ambion® mirVana™ RNA isolation kit (Life Technologies, Austin, Tex.), and the like. It will be appreciated that target polynucleotides may be cut or sheared prior to analysis, including the use of such procedures as mechanical force, sonication, restriction endonuclease cleavage, or any method known in the art. In general, the target polynucleotides of the present teachings will be single-stranded, though in some embodiments the target polynucleotide may be double-stranded, and a single-strand may result from denaturation.

As used herein, the term "mature small RNA" refers to a small RNA molecule generally comprising about 20-30 nucleotides that was processed from a larger RNA precursor. Typically, a mature small RNA has a 5' terminal phosphate group and a 3' terminal hydroxyl group. Several different types of small RNA molecules may be detected by the methods provided herein. Examples of mature small RNAs that may be detected include, but are not limited to, microRNA (miRNA), short interfering RNA (siRNA), short (or small) hairpin RNA (shRNA), repeat-associated siRNA (rasiRNA), transacting siRNA (tasiRNA), Piwi-interacting RNA (piRNA) and 21U RNA. The small RNA may be encoded in the genome or may originate from an exogenous double-stranded RNA molecule. The length of the mature small RNA that may be detected by the methods described herein may vary. In certain embodiments, the mature small RNA may range from about 10 nucleotides to about 50 nucleotides in length. In certain embodiments, the mature small RNA may range from about 15 nucleotides to about 35 nucleotides in length. In other embodiments, the mature small RNA may be from about 17, 18, 19, 20, 21, 22, 23, 24, 25, 26, 27, 28, 29, 30, 31 or 32 nucleotides in length.

The amount of small mature RNA in the sample added to the ligation reaction or to the polyadenylation reaction may vary depending on the source of the RNA-containing sample. In general, any amount of small mature RNA that can be ligated to a ligation adaptor can be used in a ligation step and any amount of small mature RNA that can be polyadenylated can be used in the polyadenylation step. Typically, the amount of purified small mature RNA used per reaction volume will be less than the amount of total RNA used per reaction volume. In certain embodiments, the amount of total RNA ranges from about 100 ng to about 20 pg. In certain embodiments, the amount of total RNA ranges from about 100 ng to about 2.5 ng.

As used herein, the terms "adaptor" and "ligation adaptor" are equivalent and used interchangeably and refer to an oligonucleotide that is ligated to the 5' end of the mature small RNA (i.e., a 5' ligation adaptor) or the 3' end of the mature small RNA or of the cDNA thereof (i.e., a 3' ligation adaptor). The nucleotides of the 5' ligation adaptor and the 3' ligation adaptor may be standard or natural (i.e., adenosine, guanosine, cytidine, thymidine, and uridine) as well as non-standard nucleotides. Non-limiting examples of non-standard nucleotides include inosine, xanthosine, isoguanosine, isocytidine, diaminopyrimidine and deoxyuridine. The ligation adaptors may comprise modified or derivatized nucleotides. Non-limiting examples of modifications in the ribose or base moieties include the addition, or removal, of acetyl groups, amino groups, carboxyl groups, carboxymethyl groups, hydroxyl groups, methyl groups, phosphoryl groups and thiol groups. In particular, included are 2'-O-methyl and locked nucleic acids (LNA) nucleotides. Suitable examples of derivatized nucleotides include those with covalently attached dyes, such as fluorescent dyes or quenching dyes, or other molecules such as biotin, digoxygenin, or magnetic particles or microspheres. The ligation adaptors may also comprise synthetic nucleotide analogs such as morpholinos or peptide nucleic acids (PNA). Phosphodiester bonds or phosphothioate bonds may link the nucleotides or nucleotide analogs of the linkers.

In certain embodiments, the 5' ligation adaptor and the 3' ligation adaptor are linear oligonucleotides (see FIG. 3). In certain embodiments, the 5' ligation adaptor comprises a 5' ligation splint complementary region at the 3' terminal region that is complementary to the 3' region of the 5' ligation splint and a universal forward primer binding site located upstream of the 5' ligation splint complementary region. The universal forward primer binding site in the 5' ligation adaptor is complementary to the universal forward primer. In certain embodiments, the 3' ligation adaptor comprises a blocking group at the 3' end, a 3' ligation splint complementary region at the 5' terminal region that is complementary to the 5' portion of the 3' ligation splint and a universal RT/reverse primer binding site located downstream of the 3' ligation splint complementary region. The universal RT/reverse primer binding site is complementary to the universal RT/reverse primer. In certain embodiments, the 5' ligation adaptor is an RNA oligonucleotide and the 3' ligation adaptor is a DNA oligonucleotide.

In certain embodiments, the 3' ligation adaptor is for ligation to the 3' end of cDNA and comprises a 3' ligation splint complementary region at the 5' terminal region that is complementary to the 5' portion of the 3' ligation splint and a universal forward primer binding site located at the 3' terminal region. The universal forward primer binding site is complementary to the universal forward primer. In certain embodiments, the 3' ligation adaptor further comprises a blocking group at the 3' end. In certain embodiments, the 3' ligation adaptor is a DNA oligonucleotide.

The length of the 5' and 3' ligation adaptors will vary depending upon, for example, the desired length of the ligation product and the desired features of the linkers. In general, the 5' ligation adaptor may range from about 15 to about 30 nucleotides in length, more preferably from about 19 nucleotides to about 26 nucleotides in length. In certain embodiments, the 5' ligation adaptor may be about 15, 16, 17, 18, 19, 20, 21, 22, 23, 24, 25, 26, 27, 28, 29, or 30 nucleotides in length. In general, the 3' ligation adaptor may range from about 15 to about 30 nucleotides in length, more preferably from about 19 nucleotides to about 26 nucleotides in length. In certain embodiments, the 3' ligation adaptor may be about 15, 16, 17, 18, 19, 20, 21, 22, 23, 24, 25, 26, 27, 28, 29 or 30 nucleotides in length. In certain embodiments, the Tm of the ligation adaptors ranges from about 30° C. to about 60° C., more preferably from about 33° C. to about 55° C.

In certain embodiments, the 5' ligation adaptor and 3'-ligation adaptor contain a stem-loop structure (herein referred to as "5' or 3' stem-loop ligation adaptors"), wherein the 5' stem-loop ligation adaptor comprises a 5' single-stranded overhang, a stem and a loop, wherein the 3' end of the stem portion is ligated to the 5' end of the mature small RNA and the 5' single-stranded overhang comprises 3 to 6 degenerate nucleotide bases which hybridize with the 5' terminal region of the mature small RNA and which serves as a ligation splint (see FIG. 4). In certain embodiments, the 3' stem-loop ligation adaptor comprises a 3' single-stranded overhang, a stem and a loop, wherein the 5' end of the stem portion is ligated to the 3' end of the mature small RNA and the 3' single-stranded overhang comprises 3 to 6 degenerate nucleotide bases which hybridize/anneal with the 3' terminal region of the mature small RNA and which serves as a ligation splint. In certain embodiments, both the 5' and 3' stem-loop ligation adaptors are DNA-RNA hybrid oligonucleotides. In certain embodiments, the 3' stem-loop ligation adaptor is a DNA oligonucleotide. In certain embodiments, the universal forward primer binding site is located in the stem portion of the 5' stem-loop ligation adaptor. In certain embodiments, the universal forward primer binding site is located in the loop portion of the 5' stem-loop ligation adaptor. In certain embodiments, the universal forward primer binding site is located in the stem and loop portions of the 5' stem-loop ligation adaptor. In certain embodiments, the universal RT/reverse primer binding site is located in the stem portion of the 3' stem-loop ligation adaptor. In certain embodiments, the universal RT/reverse primer binding site is located in the loop portion of the 3' stem-loop ligation adaptor. In certain embodiments, the universal RT/reverse primer binding site is located in the stem and loop portions of the 3'-stem-loop ligation adaptor.

In certain embodiments, the 3' stem-loop ligation adaptor comprises a 3' single-stranded overhang, a stem and a loop, wherein the 5' end of the stem portion is ligated to the 3' end of the cDNA of a mature small RNA and the 3' single-stranded overhang comprises about 3 to about 6 nucleotide bases which hybridize with the 3' terminal region of the cDNA and which serves as a ligation splint. In certain embodiments, the 3' single-stranded overhang comprises about 3 to about 6 degenerate bases. In certain embodiments, the 3'stem-loop ligation adaptor is a DNA-RNA hybrid oligonucleotide. In certain embodiments, the 3' stem-loop ligation adaptor is a DNA oligonucleotide. In certain embodiments, the universal primer binding site is located in the stem portion of the 3' stem-loop ligation adaptor. In certain embodiments, the universal primer binding site is located in the loop portion of the 3' stem-loop ligation adaptor. In certain embodiments, the universal primer binding site is located in the stem and loop portions of the 3'-stem-loop ligation adaptor.

As used herein, the term "stem" refers to the double-stranded region of the stem-loop ligation adaptor that is located between the 3' degenerate overhang (in the case of the 3' stem-loop ligation adaptor) or the 5' degenerate overhang (in the case of the 5' stem-loop ligation adaptor) and the loop. Generally, the stem is between about 10 nucleotides and about 20 nucleotides in length, more preferably the stem is between 12 and about 15 nucleotides in length. In certain embodiments, the stem is about 10, 11, 12, 13, 14, 15, 16, 17, 18, 19 or 20 nucleotides in length. As a general matter, in those embodiments in which a portion of the universal primer is encoded in the stem, the stem may be longer. In those embodiments in which a portion of the universal primer is not encoded in the stem, the stem may be shorter. Those in the art will appreciate that stems shorter than about 10 nucleotides and longer than about 20 nucleotides may be identified in the course of routine methodology and without undue experimentation such that shorter and longer stems are contemplated by the present teachings.

As used herein, the term "loop" refers to the single-stranded region of the stem-loop ligation adaptor that is located between the two complementary strands of the stem and typically the loop comprises single-stranded nucleotides, although other moieties such as modified DNA or RNA, carbon spacers such as C18, and/or polyethylene glycol (PEG) are also possible. Generally, the loop is between about 10 and about 20 nucleotides in length, more preferably the loop is between 17 nucleotides and 19 nucleotides in length. In certain embodiments, the loop is about 10, 11, 12, 13, 14, 15, 16, 17, 18, 19 or 20 nucleotides in length. As a general matter, in those embodiments in which a universal primer is encoded in the loop, the loop may generally be longer. In those embodiments in which a universal primer is not encoded in the loop, the loop my generally be shorter. Those in the art will appreciate that loops shorter than about 10 nucleotides and longer than about 20 nucleotides may be identified in the course of routine methodology without undue experimentation and that shorter and longer loops are contemplated by the present teachings.

As used herein, the term "ligation product" refers to a hybrid molecule comprising at least one ligation adaptor and a mature small RNA or a hybrid molecule comprising at least one ligation adaptor and a cDNA.

In certain embodiments, ligation of the mature small RNA is performed in the presence of 5' and 3' semi-degenerate ligation splints (see FIG. 3). The 5' ligation splint comprises two distinct regions: a 5' terminal region containing degenerate nucleotide bases, ranging from about 3 nucleotides to about 6 nucleotides that hybridizes with the 5' end of the mature small RNA and a 3' region that hybridizes with the 3' end of the 5' ligation adaptor. The 3' ligation splint comprises two distinct regions: a 3' terminal region that contains degenerate nucleotide bases, ranging from about 3 nucleotides to about 6 nucleotides, that hybridizes with the 3' end of the mature small RNA and a 5' region that hybridizes with the 5' end of the 3' ligation adaptor. The non-degenerate portion of the 5' ligation splint may be an exact complement or it may be a nearly exact complement of the 5' ligation adaptor sequence. The non-degenerate portion of the 3' ligation splint may be an exact complement or it may be a nearly exact complement of the 3' ligation adaptor sequence. Since the ligation splints hybridize to the ligation adaptors and the mature small RNA, they span the ligation junctions such that for the 5' ligation splint, the 3' end of the 5' ligation adaptor is brought into close proximity to the 5' end of the mature small RNA and for the 3' ligation splint, the 5' end of the 3' ligation linker is brought into close proximity to the 3' end of the mature small RNA.

In certain embodiments, ligation of the cDNA of a mature small RNA is performed in the presence of a 3' ligation splint (see FIG. 2). The 3' ligation splint comprises two distinct regions: a 3' terminal region that contains nucleotide bases, ranging for example from about 3 nucleotides to about 6 nucleotides, that hybridizes with the 3' end of the cDNA and a 5' region that hybridizes with the 5' end of the 3' ligation adaptor. In some embodiments, the 3' ligation splint is semi-degenerate and the 3' terminal region contains degenerate nucleotide bases, ranging for example from about 3 nucleotides to about 6 nucleotides, that hybridizes with the 3' end of the cDNA. Since the ligation splint hybridizes to the ligation adaptor and the cDNA, it spans the ligation junction such that the 5' end of the 3' ligation linker is brought into close proximity to the 3' end of the cDNA.

In general, the ligation splints may range from about 10 to about 20 nucleotides in length, more preferably from about 15 to about 19 nucleotides in length with about 3 to about 6 nucleotides being degenerate in order to interact with a variety of mature small RNA molecules or cDNA molecules thereof and the remainder of the nucleotides being complementary to either the 3' portion of the 5' ligation adaptor or the 5' portion of the 3' ligation adaptor. A person skilled in the art will appreciate that the ligation splint may be longer than 20 nucleotides or shorter than about 10 nucleotides provided it hybridizes with the 5' or 3' ligation adaptor.

In certain embodiments, the ligation splint may be an RNA oligonucleotide. In certain embodiments, the ligation splint may be a chimeric DNA/RNA oligonucleotide. In certain embodiments, the ligation splint may be a DNA oligonucleotide. In a preferred embodiment, the 5' ligation splint is a DNA oligonucleotide and the 3' ligation splint is a DNA oligonucleotide. In yet another embodiment, the ligation splint is a DNA oligonucleotide comprising at least one blocking agent such that the ligation template may not serve as a primer for PCR amplification or as a substrate for non-specific (or false) ligation. Non-limiting examples of blocking groups include dideoxynucleotides, amine groups, methyl groups, phosphate groups, or carbon spacers. Preferred blocking groups include 2'-O methyl and phosphothioate. The 5' and 3' ligation splints may comprise standard, non-standard, modified or derivatized nucleotides or nucleotide analogs as described herein above. Phosphodiester bonds or phosphothioate bonds may link the nucleotides of the ligation splints.

The universal ligation adaptor sequences facilitate the synthesis of cDNA in reverse transcription and/or pre-amplification of cDNA in PCR using universal primers. To drive the ligation of ligation adaptors to miRNA, an excess amount of ligation adaptors are used; therefore, ligation between the two ligation linkers may be produced as a non-specific background by-product in the methods disclosed herein. In other embodiments, ligation between free (unannealed) universal reverse transcription primers and 3' ligation adaptors may be produced as a by-product during the ligation step in the provided methods, such by-product leads to non-specific background during detection. This background compromises the detection of low abundant transcripts in both qPCR and next generation sequencing (NGS) analysis and detection. To reduce the background, blocking oligonucleotides were developed to selectively suppress amplification and/or ligation of the adaptor-adaptor by-product or adaptor-primer by-product. DNA oligonucleotides labeled at the 5' or 3' end with blocking groups, such as acridine, MGB, 2'-O-methyl, sequence-targeted amplification restrictive (STAR) blockers, and blocking oligonucleotides comprising a poly(A) sequence, may be used in the ligation, extension and/or amplification steps. The addition of such blocking oligonucleotide was found to dramatically reduce background amplification and increase sensitivity of miRNA detection by qPCR with TaqMan® qPCR assays (see Example 4).

A STAR blocker oligonucleotide comprises a STAR tag sequence at the 5' end of the oligonucleotide, the STAR tag sequence being complementary to all or a portion of another primer sequence that is used in the amplification reaction (see FIG. 15). When the STAR blocker primer is extended, the extension product comprises both the STAR tag sequence at the 5' end and the complement of the STAR tag sequence in the 3' region of the extension product. Thus, the STAR primer extension product can may fold back to self-anneal thereby forming a stem-loop structure. The stem-loop structure of the extended STAR primer excludes binding of the other primer used to amplify the target molecule, thereby inhibiting amplification of the unwanted target (for example, an adaptor-adaptor ligation product). In certain embodiments, the STAR tag sequence may comprise a portion of the amplicon internal sequence to block the annealing of another primer or the extension of a DNA polymerase. STAR primers may be used for selective amplification suppression of ligated ligation adaptors in the pre-amplification of adaptor-ligated small mature RNA or cDNA in the methods provided. STAR primers are described in co-owned, U.S. Provisional Patent Application No. 61/740,242, filed Dec. 20, 2012, herein incorporated by reference in its entirety.

In certain embodiments, the blocking oligonucleotide comprises a poly(A) portion and is present during the ligation reaction. In methods in which a polyadenylated mature small RNA is reverse transcribed using a universal reverse transcription primer to generate a cDNA and a ligation adaptor is ligated to the 3' end of the cDNA, the inclusion of a blocking oligonucleotide during the ligation reaction can selectively suppress formation of adaptor-universal RT primer by-product. In certain embodiments, a blocking oligonucleotide has a stem-loop structure and a poly(A) containing single-stranded overhang portion at its 3' end (see FIG. 15 D). In other embodiments, the blocking oligonucleotide is a linear oligonucleotide and has a poly(A) portion at its 5' end and sequences complementary to the universal reverse transcription primer at its 3' end. In certain embodiments, the non-poly(A) portion of the blocking oligonucleotide comprises deoxyuridine. Hybridization of such a blocking oligonucleotide to a free (unannealed, unextended) universal RT primer prevents the ligation splint from annealing to the primer and facilitating ligation of the ligation adaptor, thereby suppressing unwanted formation of adaptor-universal RT primer byproduct. In certain embodiments, the Tm of the RT primer and blockers comprising a poly(A) portion ranges from about 30° C. to about 60° C., from about 35° C. to about 50° C., or about 38° C. to about 42° C.

A "blocking group" is a chemical moiety that can be added to a nucleotide or a nucleic acid to prevent or minimize nucleotide addition by a DNA polymerase. By adding a blocking group to the terminal 3'-OH, the nucleotide is no longer able to participate in phosphodiester bond formation catalyzed by the DNA polymerase. Some non-limiting examples include, an alkyl group, non-nucleotide linkers, phosphorothioate, alkane-diol residues, PNA, LNA, nucleotide analogs comprising a 3'-amino group in place of the 3'-OH group, nucleotide analogs comprising a 5'-OH group in place of the 5'-phosphate group, nucleotide derivatives lacking a 3'-OH group, biotin, nucleic acid intercalators, acridine, and minor groove binders. An alkyl blocking group is a saturated hydrocarbon that can be straight chained, branched, cyclic, or combinations thereof. Some non-limiting examples of non-extendable nucleotides include nucleotides that have a 3'-hydroxyl group that has been modified such as by substitution with hydrogen or fluorine or by formation of an ester, amide, sulfate or glycoside. These nucleotides are generally not chain extendable. Other examples of non-extendable nucleotides that can be used include nucleotides that have modified ribose moieties. In certain embodiments, ribonucleotides may serve as non-extendable nucleotides because oligonucleotides terminating in ribonucleotides cannot be extended by certain DNA polymerases. The ribose can be modified to include 3'-deoxy derivatives including those in which the 3'-hydroxy is replaced by a functional group other than hydrogen, for example, as an azide group. In certain embodiments, a non-extendible nucleotide comprises a dideoxynucleotide (ddN), for example but not limited to, a dideoxyadenosine (ddA), a dideoxycytosine (ddC), a dideoxyguanosine (ddG), a dideoxythymidine (ddT), or a dideoxyuridine (ddU). In a preferred embodiment, the blocking group is selected from the group consisting of a minor groove binder, a 2'-O-methyl group, a biotin, an acridine, and a phosphothioate group.

Ligation of the ligation adaptors to the mature small RNA or the cDNA thereof is catalyzed by a ligase, for example a template-dependent DNA ligase. Exemplary ligases used in the methods, kits and compositions provided herein include, but are not limited to, T4 DNA ligase, Tfi DNA ligase, DNA ligase I, DNA ligase II, DNA ligase III, DNA ligase IV, and small footprint DNA ligases. In a preferred embodiment, T4 DNA ligase is used.

The conditions of the ligation reaction are typically adjusted so that the ligase functions near its optimal activity level. A buffering agent may be utilized to adjust and maintain the pH at the desired level. Representative examples of suitable buffers include, but are not limited to, MOPS, HEPES, TAPS, Bicine, Tricine, TES, PIPES, MES, sodium acetate and Tris buffer.

The ligation mixture may further comprise a divalent cation. Suitable divalent cations include, but are not limited to calcium, magnesium and manganese. The reaction mixture may further comprise a reducing agent. Non-limiting examples include dithiothreitol and β-mercaptoethanol. A ribonuclease (RNase) inhibitor may also be added to the ligation mixture. The ligation mixture may further comprise ATP.

As used herein, the term "extension reaction" refers to an elongation reaction in which the 3' ligation adaptor ligated to the 3' end of the mature small RNA is extended to form an "extension reaction product" comprising a strand complementary to the target polynucleotide. As used herein, extension reaction is also referred to as "reverse transcription." In some embodiments, the elongation reaction comprises extending the polyadenylated portion of the 3' end of the mature small RNA. In some embodiments, the target polynucleotide is a miRNA molecule and the extension reaction is a reverse transcription reaction comprising a reverse transcriptase, whereby a DNA copy of the ligation product is made. In certain embodiments, the extension reaction is a reverse transcription reaction comprising a polymerase, such as a reverse transcriptase.

Reverse transcriptases include any enzyme having reverse transcriptase activity. Such enzymes include, but are not limited to, retroviral reverse transcriptase (e.g., Moloney Murine Leukemia Virus (M-MLV), Avian Myeloblastosis Virus (AMV) or Rous Sarcoma Virus (RSV) reverse transcriptases), Superscript I®, Superscript II®, Superscript III®, retrotransposon reverse transcriptase, hepatitis B reverse transcriptase, cauliflower mosaic virus reverse transcriptase, bacterial reverse transcriptase, Tth DNA polymerase, Taq DNA polymerase, Tne DNA polymerase, Tma DNA polymerase, and mutants, variants or derivatives thereof.

In one embodiment, reverse transcriptases include those that have reduced, substantially reduced or eliminated RNase H activity. By an enzyme "substantially reduced in RNase H activity" is meant that the enzyme has less than about 20%, 15%, 10%, 5%, or 2%, of the RNase H activity of the corresponding wild type or RNase H+ enzyme such as wild type Moloney Murine Leukemia Virus (M-MLV), Avian Myeloblastosis Virus (AMV) or Rous Sarcoma Virus (RSV) reverse transcriptases. The RNase H activity of any enzyme may be determined by a variety of assays, such as those described, for example, in U.S. Pat. No. 5,244,797, in Kotewicz, M. L., et al, Nucl. Acids Res. 16:265 (1988) and in Gerard, G. F., et al., FOCUS 14:91 (1992), the disclosures of all of which are fully incorporated herein by reference. Polypeptides suitable for use in the compositions and methods described herein include, but are not limited to, M-MLV H-reverse transcriptase, RSV H-reverse transcriptase, AMV H-reverse transcriptase, RAV (Rous-associated virus) H-reverse transcriptase, MAV (myeloblastosis-associated virus) H-reverse transcriptase, HIV H-reverse transcriptase, and Superscript III®, and mutants, variants or derivatives thereof. It will be understood by one of ordinary skill, however, that any enzyme capable of producing a DNA molecule from a ribonucleic acid molecule (i.e., having reverse transcriptase activity) may be equivalently used in the compositions, methods and kits described herein.

The enzymes having reverse transcriptase and/or polymerase activity may be obtained commercially, for example from Life Technologies Corp. (Carlsbad, Calif.), Perkin-Elmer (Branchburg, N.J.), New England BioLabs (Beverly, Mass.) or Boehringer Mannheim Biochemicals (Indianapolis, Ind.). Alternatively, polymerases or reverse transcriptases having polymerase activity may be isolated from their natural viral or bacterial sources according to standard procedures for isolating and purifying natural proteins that are well-known to one of ordinary skill in the art (see, e.g., Houts, G. E., et al., J. Virol. 29:517 (1979)). In addition, such polymerases and/or reverse transcriptases may be prepared by routine recombinant DNA techniques well know to those skilled in the art (see, e.g., Kotewicz, M. L., et al., Nucl. Acids Res. 16:265 (1988); U.S. Pat. No. 5,244,797; PCT Patent Application Publication No. WO 98/47912; Soltis, D. A., and Skalka, A. M., Proc. Natl. Acad. Sci. USA 85:3372-3376 (1988)).

In some embodiments, newly-formed nucleic acid duplexes are not initially denatured, but are used in their double-stranded form in one or more subsequent steps. An extension reaction is an amplifying technique that comprises elongating a ligation product that is annealed to a template in the 5' to 3' direction using an amplifying means such as a polymerase and/or reverse transcriptase (and a universal RT/reverse primer). According to some embodiments, with appropriate buffers, salts, pH, temperature, and nucleotide triphosphates, including analogs thereof, i.e., under appropriate conditions, a polymerase incorporates nucleotides complementary to the template strand starting at the 3' end of an annealed ligation product, to generate a complementary strand. In some embodiments, the polymerase used for extension lacks or substantially lacks 5' exonuclease activity. In some embodiments of the present teachings, unconventional nucleotide bases may be introduced into the amplification reaction products and the products treated by enzymatic (e.g., glycosylases) and/or physical-chemical means in order to render the product incapable of acting as a template for subsequent amplifications. In some embodiments, uracil can be included as a nucleobase in the reaction mixture, thereby allowing for subsequent reactions to decontaminate carryover of previous uracil-containing products by the use of uracil-N-glycosylase (see for example PCT Application Publication No. WO 92/01814A2). In some embodiments of the present teachings, any of a variety of techniques can be employed prior to amplification in order to facilitate amplification success, as described for example in Radstrom et al., Mol Biotechnol. 26:133-46 (2004). In some embodiments, amplification may be achieved in a self-contained integrated approach comprising sample preparation and detection, as described for example in U.S. Pat. Nos. 6,153,425 and 6,649,378. Reversibly modified enzymes, for example but not limited to those described in U.S. Pat. No. 5,773,258, are also within the scope of the disclosed teachings. The present teachings also contemplate various uracil-based decontamination strategies, wherein for example uracil may be incorporated into an amplification reaction, and subsequent carryover products removed with various glycosylase treatments (see, for example, U.S. Pat. No. 5,536,649). Those in the art will understand that any protein with the desired enzymatic activity may be used in the disclosed methods and kits.

In certain embodiments, the target polynucleotide is a miRNA or other mature small RNA molecule and as such it will be appreciated that the use of polymerases that also comprise reverse transcription properties can allow for some embodiments of the present teachings to comprise a first reverse transcription reaction followed thereafter by an amplification reaction, thereby allowing for the consolidation of two reactions in essentially a single reaction. In certain embodiments, the consolidation of the extension reaction and subsequent amplification reaction is further contemplated by the present teachings.

As used herein, the term "universal primer portion" refers to a region of a ligation adaptor or a universal reverse transcription (RT) primer that may serve directly, or by virtue of its complement, as the template upon which a universal primer may hybridize for any of a variety of primer nucleotide extension reactions known in the art (for example, PCR or RT-PCR). It will be appreciated by those of skill in the art that when two primer portions are present on a single polynucleotide, the orientation of the two primer portions is generally different. For example, one PCR primer may directly hybridize to a first primer portion, while the other PCR primer may hybridize to the complement of the second primer portion. In addition, "universal" primers and primer portions as used herein are generally chosen to be as unique as possible given the particular assays and host genomes to ensure specificity of the assay.

As used herein, the term "universal primer" refers to a primer that may be used in a plurality of different reactions querying different target polynucleotides and hybridizes to the universal primer portion of the ligation adaptor or universal RT primer. Generally, the region of the universal primer that hybridizes to the ligation adaptor or RT primer is between about 15 and about 25 nucleotides in length, more preferably between about 18 nucleotides and about 22 nucleotides in length. In certain embodiments, the region that hybridizes to the ligation adaptor or RT primer is about 15, 16, 17, 18, 19, 20, 21, 22, 23, 24, or 25 nucleotides in length. Those in the art will appreciate that lengths of the ligation adaptor or RT primer portion of the universal primer may be shorter than about 15 nucleotides and longer than about 25 nucleotides in length and may be identified in the course of routine methodology and without undue experimentation and that such longer or shorter ligation adaptor or RT primer portions of universal primers are contemplated by the present teachings. The universal primer may comprise standard, non-standard, derivatized and modified nucleotides as described herein.

As used herein, the term "universal reverse transcription (RT) primer" refers to a primer that may be used in a plurality of different reactions querying different target polynucleotides. The universal RT primer comprises a poly(T) portion and a tail portion, wherein the tail portion comprises a universal primer portion. Typically, the poly(T) portion is at the 3' end of the universal RT primer. In certain embodiments, the poly(T) sequence at the 3' end of the primer is followed by one additional nucleotide base which is not a T. Generally, the universal RT primer is between about 15 and 25 nucleotides in length, more preferably between about 18 nucleotides and about 22 nucleotides in length. In certain embodiments, the universal RT primer is about 15, 16, 17, 18, 19, 20, 21, 22, 23, 24 or 25 nucleotides in length. The universal RT primer may comprise standard, non-standard, derivatized and modified nucleotides as described herein above.

As used herein, the term "universal forward primer" refers to a primer that may be used in a plurality of different reactions querying different target polynucleotides. As used herein, the term "universal RT/reverse primer" refers to a primer that may be used in a plurality of different reactions querying different target polynucleotides. As used herein, the term "universal reverse primer" refers to a primer that may be used in a plurality of different reactions querying different target polynucleotides. In a typical PCR amplification, forward and reverse primers are used to preferentially target and amplify a DNA sequence of interest. As used in the provided methods, a single pair of universal forward and reverse primers allows amplification of different target polynucleotides since the target polynucleotides are modified to include universal primer portions that serve directly, or by virtue of its complement, as a template upon which a universal forward or reverse primer may hybridize.

In certain embodiments, the universal forward primer hybridizes to the universal primer portion of the 5' ligation adaptor. Generally, the region of the universal forward primer that hybridizes to the 5' ligation adaptor is between about 15 and about 25 nucleotides in length, more preferably between about 18 nucleotides and about 22 nucleotides in length. In certain embodiments, the region that hybridizes to the 5' ligation adaptor is about 15, 16, 17, 18, 19, 20, 21, 22, 23, 24, or 25 nucleotides in length. Those in the art will appreciate that lengths of the 5' ligation adaptor portion of the universal forward primer may be shorter than about 15 nucleotides and longer than about 25 nucleotides in length and may be identified in the course of routine methodology and without undue experimentation and that such longer or shorter 5' ligation adaptor portions of universal forward primers are contemplated by the present teachings. The universal forward primer may comprise standard, non-standard, derivatized and modified nucleotides as described herein above.

As used herein, the term "universal RT/reverse primer" refers to a primer that may be used in a plurality of different reactions querying different target polynucleotides. In some embodiments, a universal RT/reverse primer hybridizes to a portion of the 3' ligation adaptor comprising the universal primer portion of the 3' ligation adaptor. Following the extension reaction, the universal forward primer may be extended to form a second strand product. The universal RT/reverse primer may hybridize with this second strand and may be extended to continue the amplification reaction. Generally, the universal RT/reverse primer is between about 15 and 25 nucleotides in length, more preferably between about 18 nucleotides and about 22 nucleotides in length. In certain embodiments, the universal RT/reverse primer is about 15, 16, 17, 18, 19, 20, 21, 22, 23, 24 or 25 nucleotides in length. The universal RT/reverse primer may comprise standard, non-standard, derivatized and modified nucleotides as described herein above.

The term "upstream" as used herein takes on its customary meaning in molecular biology, and refers to the location of a region of a polynucleotide that is on the 5' side of a "downstream" region. Correspondingly, the term "downstream" refers to the location of a polynucleotide that is on the 3' side of an "upstream" region.

In certain embodiments, the methods provided herein further includes assaying the ligation product comprising the mature small RNA and the 5' and 3' ligation adaptors, such that the mature small RNA is detected. In certain embodiments, the methods provided herein further include assaying the ligation product comprising the cDNA of the mature small RNA and the 3' ligation adaptor, such that the mature small RNA is detected. The assays may be quantitative, such that the amount or copies of the mature small RNA in a sample may be determined. Alternatively, the assays may be qualitative, such that the presence of a mature small RNA may be determined in the sample, but its level may not be measured. Furthermore, the assays may be such that the mature small RNA or its cDNA may be isolated from the sample for further study.

In certain embodiments, an amplification method may be used to assay the ligation product. Non-limiting examples of suitable amplification methods include quantitative real-time PCR, quantitative end-point PCR and standard PCR. In certain embodiments, the small mature RNA is polyadenylated and reverse transcribed to a DNA copy by using a reverse transcriptase and a universal RT primer comprising a poly(T) portion. Following reverse transcription, a ligation adaptor comprising a universal primer portion is ligated to the 3' end of the cDNA, whereby the cDNA ligation product can be pre-amplified and/or amplified by suitable methods. Pre-amplification of the cDNA can be accomplished using universal forward and reverse primers. To assay the cDNA ligation product in certain embodiments, the amplification method may use a small RNA-specific forward primer and a universal reverse primer, and the detection of the amplified cDNA may be through use of a universal probe (see, for example, FIG. 2 at (A)). In certain embodiments, the assay amplification method may use universal forward and reverse primers, and the detection of the amplified cDNA may be through use of a small-RNA specific probe (see, for example, FIG. 2 at (B). The universal forward and reverse primers and the small RNA-specific forward and reverse primers may comprise standard, nonstandard, derivatized and modified nucleotides as detailed above. The forward and reverse primers may each range from about 15 to about 25 nucleotides in length, and in certain embodiments, from about 18 nucleotides to about 22 nucleotides in length.

In other embodiments, to amplify the ligation product comprising a small mature RNA, the ligation product is generally converted into a DNA copy. In certain embodiments, a DNA copy of the ligation product may be synthesized during PCR by using a universal RT/reverse primer that hybridizes to the 3' end of the ligation product, whereby a thermostable DNA polymerase extends the primer using the ligation product as the template. The universal RT/reverse primer is complementary to the universal RT/reverse primer portion of the 3' ligation adaptor. The universal RT/reverse primer used to generate a DNA copy of the ligation product will generally also be used to amplify the product, in conjunction with a universal forward primer. In general, the universal forward primer corresponds to a sequence of the 5' ligation adaptor. Both of the universal forward and reverse primers may comprise standard, non-standard, derivatized and modified nucleotides as detailed above. The universal forward and reverse primers may each range from about 15 to about 25 nucleotides in length, more preferably from about 18 nucleotides to about 22 nucleotides in length.

In certain embodiments, quantitative real-time PCR (qPCR) may be used to assay the ligation product. In this method, the amount of PCR product is followed cycle-by-cycle in real time. To measure the amount of PCR product, the reaction may be performed in the presence of a fluorescent dye whose fluorescence increases greatly when bound to double-stranded DNA. Non-limiting examples of suitable fluorescent dyes include SYBR® Green I, PicoGreen® I, EvaGreen™, ethidium bromide and acridine orange. The reaction may also be performed with a fluorogenic reporter probe that is specific for the DNA being amplified. Non-limiting examples of reporter probes include TaqMan® probes, molecular beacons, and Scorpion® primers. The aforementioned probes depend on Förster Resonance Energy Transfer (FRET) to quench the fluorescence signal via the coupling of a fluorogenic dye molecule and a quencher moiety on the same or different oligonucleotide substrates. The fluorescence signal is generated when the fluorogenic dye molecule and the quencher are decoupled via enzymatic or physical means. Fluorescence values are generally recorded during each cycle and represent the amount of product amplified to that point in the amplification reaction. The cycle during which the fluorescence exceeds a defined threshold value is defined as the threshold cycle (Ct). In general, the amount of starting material may be calculated by determining the Ct value of the sample and comparing it to Ct value of control samples.

In certain embodiments, quantitative end-point PCR may also be used to assay the ligation product. This method is similar to qPCR in that the reaction is generally performed in the presence of a fluorescent dye or a fluorogenic probe and/or primer, but the amount of PCR product is not followed cycle-by-cycle. Rather the PCR product is analyzed at the end of the reaction by resolving the amplified product by electrophoresis on a DNA chip, an agarose gel, or a capillary, and then measuring the fluorescence of the product. The reaction typically includes a co-amplified internal control or a co-amplified synthetic nucleic acid for sample normalization.

In certain embodiments, a standard PCR method may also be used to assay the ligation product. Standard PCR procedures are well known in the art and information regarding these may be found in Ausubel et al. Current Protocols in Molecular Biology, John Wiley and Sons, NY, 1998; Ausubel et al, PCR Protocols: A Guide to Methods and Applications, Academic Press, NY, 1990 or Sambrook et al. Molecular Protocols: A Laboratory Manual, 3rd ed., Cold Spring Harbor Press, NY, 2001.

The terms "amplicon" and "amplification product" as used herein generally refer to the product of an amplification reaction. An amplicon may be double-stranded or single-stranded, and may include the separated component strands obtained by denaturing a double-stranded amplification product. In certain embodiments, the amplicon of one amplification cycle can serve as a template in a subsequent amplification cycle.

As used herein, the term "amplifying" refers to any means by which at least a part of a target polynucleotide, target polynucleotide surrogate, or combinations thereof, is reproduced, typically in a template-dependent manner, including without limitation, a broad range of techniques for amplifying nucleic acid sequences, either linearly or exponentially. Any of several methods can be used to amplify the target polynucleotide. Any in vitro means for multiplying the copies of a target sequence of nucleic acid can be utilized. These include linear, logarithmic, or any other amplification method. Exemplary methods include polymerase chain reaction (PCR; see, e.g., U.S. Pat. Nos. 4,683,202; 4,683,195; 4,965,188; and 5,035,996), isothermal procedures (using one or more RNA polymerases (see, e.g., PCT Application Publication No. WO 2006/081222), strand displacement (see, e.g., U.S. Pat. No. RE39,007), partial destruction of primer molecules (see, e.g., PCT Application Publication No. PCT Application Publication No. WO 2006/087574)), ligase chain reaction (LCR) (see, e.g., Wu, et al. Genomics 4:560-569 (1990) and Barany, et al. Proc. Natl. Acad. Sci. USA 88:189-193 (1991)), Qβ RNA replicase systems (see, e.g., WO 1994/016108), RNA transcription-based systems (e.g., TAS, 3SR), rolling circle amplification (RCA) (see, e.g., U.S. Pat. No. 5,854,033; U.S. Patent Application Publication No. 2004/265897; Lizardi, et al. Nat. Genet. 19:225-232 (1998); and Banér, et al. Nucleic Acid Res. 26: 5073-5078 (1998)), and strand displacement amplification (SDA) (Little, et al. Clin. Chem. 45:777-784 (1999)), among others. Many systems are suitable for use in amplifying target nucleic acids and are contemplated herein as would be understood by one of skill in the art.

In certain embodiments, the provided methods can be used to detect a rare mature small RNA in a sample and/or distinguish one small RNA from other similar or highly homologous small RNAs in the sample. In certain embodiments, methods for amplifying target nucleic acids use activation by polyphosphorolysis (APP) reactions to provide highly-specific amplification of the target small mature RNA or cDNA thereof. Polyphosphorolysis refers to the removal of a non-extendable nucleotide from a nucleic acid (e.g., an oligonucleotide) in the presence of one or more polyphosphorolyzing agents and an enzyme that exhibits polyphosphorolyzing activity. In certain embodiments, the polyphosphorolysis-activatable oligonucleotide (APP oligonucleotide) is a target specific oligonucleotide with a dideoxynucleotide at the 3' terminus. The 3' terminal dideoxynucleotide inhibits direct extension by polymerase but can be removed by polyphosphorolysis in the presence of a polyphosphorolyzing agent and the complementary strand of the target. Generally, the dideoxynucleotide is not removed if there is a mismatch between the APP oligonucleotide and its hybridization partner. Typically, the APP oligonucleotide is designed to have a nucleotide which distinguishes one target from another, for example, one miRNA from another miRNA, near the 3' end. APP may be used to polymerize and/or amplify nucleic acid molecules, including but not limited to ribonucleic acid (e.g., RNA) and/or deoxyribonucleic acid (e.g., DNA), or hybrids thereof. APP reactions and such uses thereof are described in U.S. Ser. No. 13/324,676, filed Dec. 13, 2011 and published as U.S. Pat. Pub. No. 2012/0196329, herein incorporated by reference in its entirety.

In some embodiments using APP, the one or more polyphosphorolyzing agents may be represented by Formula I:

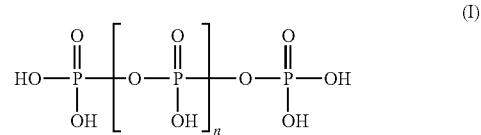

(I)

wherein n is, for example, 1, 2, 3, 4, 5, 6, 7, 8, 9, or 10, or more. In some embodiments, the one or more polyphosphorolyzing agents may be represented by Formula II:

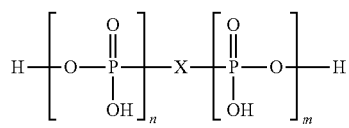

In some embodiments representing compounds of Formula II, n and/or m may be the same or different. And n and/or m may be, for example, 0, 1, 2, 3, 4, 5, 6, 7, 8, 9, or 10 with the proviso that n or m, but not both, may be 0. Thus, if n is 0, then m may be 1, 2, 3, 4, 5, 6, 7, 8, 9, or 10. If m is 0, then n may be 1, 2, 3, 4, 5, 6, 7, 8, 9, or 10. In some embodiments, n and m are both greater than or equal to 1. In some embodiments, n and m are both 1. In some embodiments, the sum of n+m is greater than or equal to 2 (e.g., n≥1 and m≥1, n≥2 and m≥0, n≥0 and m≥2). In some embodiments, such as where (but not limited to) the sum of n+m is greater than or equal to 2, X may be, for example,

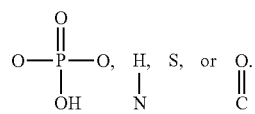

In some embodiments wherein the one or more polyphosphorolyzing agents are represented by Formula II, such as where (but not limited to) n or m=0, X may be, for example,

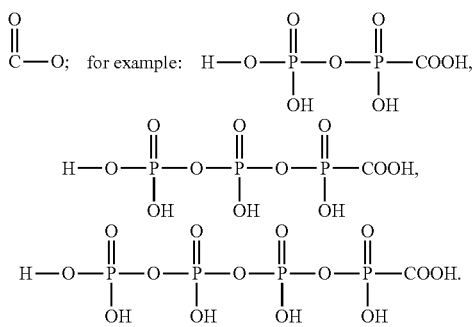

In some embodiments, the one or more polyphosphorolyzing agents may be:

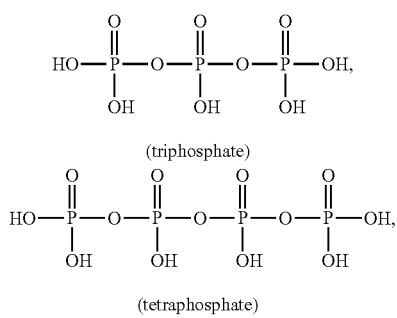

(triphosphate)

(tetraphosphate)

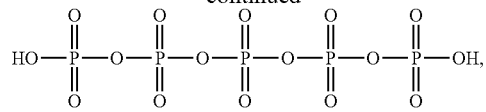

(pentaphosphate)

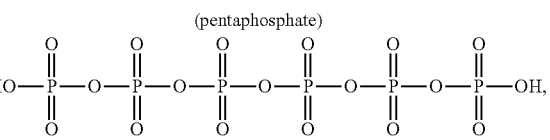

(hexaphosphate)

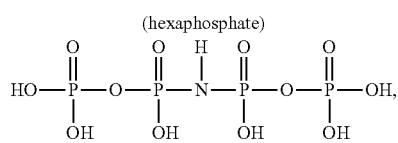

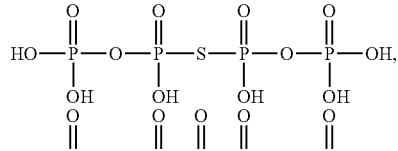

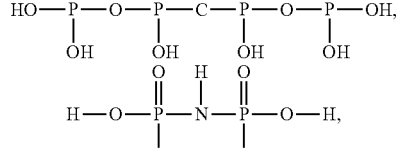

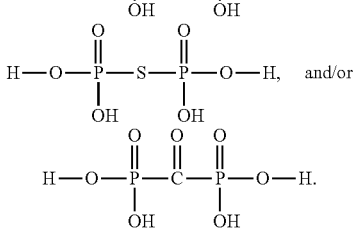

Any of the polyphosphorolyzing agents described herein may be combined with any other polyphosphorolyzing agents. In some embodiments, the one or more polyphosphorolyzing agents may be pyrophosphate ($PP_i$) in combination with at least one or more other polyphosphorolyzing agents. Any of the one or more polyphosphorolyzing agents may be used in the form of a salt (e.g., sodium). Typically, the APP reactions described herein further include one or more biocatalysts (e.g., enzyme(s)) having polyphosphorolysis activity to generate one or more nucleoside triphosphates. As shown above, for example, imidodiphosphate (IDP) links the phosphate moieties using nitrogen; similar diphosphate compounds may substitute sulfur for nitrogen. In some embodiments, a polyphosphate may be any phosphate ester having two or more phosphate moieties. In some embodiments, a polyphosphate may be any phosphate esters having three or more phosphate moieties.

An exemplary one or more biocatalyst that may be used in APP is a DNA polymerase that catalyzes polymerization of nucleoside triphosphates and polyphosphorolysis of duplexes of DNA in the presence of one or more polyphosphorolyzing agents as described herein. Exemplary DNA polymerases having polyphosphorolysis activity include but are not limited to thermostable Tfl, Taq, and/or genetically engineered DNA polymerases (e.g., AMPLITAQFS, THERMOSEQUENASE), those having the active site mutation F667Y or the equivalent of F667Y (e.g., in Tth) which shows improved affinity for dideoxynucleotide as incoming nucleotide (e.g., smaller $K_m$ for ddNTP)), RQ1 as described in U.S. Pat. No. 7,422,872 and mutants thereof (e.g., RQY in which 669 is substituted by tyrosine, which may provide for reverse transcription and/or direct sequencing of RNA), THERMINATOR I (NEB), THERMINATOR II, THERMINATOR III, and/or THERMINATOR GAMMA (all available from NEB), among others. These and other potentially suitable DNA polymerases may be described in, for example, U.S. Pub. 2008/0254525A1, U.S. Pub. 2007/0020622A1, U.S. Pub. 2007/0009924A1, U.S. Pat. No. 4,889,818, U.S. Pat. No. 4,965,188, U.S. Pat. No. 5,047,342, U.S. Pat. No. 5,079,352, U.S. Pat. No. 5,270,179, U.S. Pat. No. 5,374,553, U.S. Pat. No. 5,436,149, U.S. Pat. No. 5,512,462, U.S. Pat. No. 5,614,365, and/or U.S. Pat. No. 6,228,628B1. It has been found that the use of such genetically engineered DNA polymerases may improve the efficiency of APP.

APP provides for the extension of oligonucleotides by converting a non-extendable oligonucleotide into an extendable oligonucleotide, extending the oligonucleotide to produce a desired nucleic acid strand (e.g., a complementary copy of a target nucleic acid), and optionally amplifying and detecting the desired nucleic acid strand. A non-extendable nucleotide refers to a nucleotide, which upon incorporation into a nucleic acid prevents further extension of the nucleic acid, e.g., by at least one biocatalyst (e.g., enzyme). A nucleotide may be extendable by one enzyme, but non-extendable by another enzyme. A non-extendable nucleotide to one enzyme could become extendable or partially extendable under different conditions. An extendable nucleotide may refer to a nucleotide to which at least one other nucleotide can be added or covalently bonded at a 3'-position of the sugar moiety of the extendable nucleotide by a biocatalyst (e.g., enzyme) present in the reaction. Extension may also start from 2'-OH of a nucleotide which may or may not have an extendable 3'-OH. Extending a nucleic acid refers to the addition of or incorporation of one or more nucleotides to or into a given nucleic acid. An extended oligonucleotide is typically an oligonucleotide (e.g., a primer nucleic acid) to which one or more additional nucleotides have been added or otherwise incorporated (e.g., covalently bonded to). APP is typically carried out using the steps of: (a) annealing to a nucleic acid a first oligonucleotide which has a non-extendable 3' end ("P*") that is removable by polyphosphorolysis (i.e., activatable); (b) removing that 3' non-extendable terminus using a polyphosphorylzing agent and a biocatalyst (i.e., a DNA polymerase) having polyphosphorolysis activity to produce an unblocked oligonucleotide; and, (c) extending the unblocked oligonucleotide to produce a desired nucleic acid strand. Further steps of detecting the desired nucleic acid strand may also be included as described below.

The one or more polyphosphorolyzing agents may be included in the reaction mixture at any suitable concentration. For instance, a suitable concentration may be approximately 1-500 µM. Other suitable polyphosphorolyzing agent concentrations ranges may include but are not limited to approximately 1-10 µM, 10-20 µM, 20-30 µM, 30-40 µM, 40-50 µM, up to 50 µM, 50-60 µM, 60-70 µM, 70-80 µM, 90-100 µM, up to 100 µM, 100-150 µM, 150-200 µM, up to 200 µM, 200-250 µM, 250-300 µM, up to 300 µM, 300-350 µM, 350-400 µM, up to 400 µM, 400-450 µM, 450-500 µM. Additionally suitable polyphosphorolyzing agent concentrations include but are not limited to 1 µM, 5 µM, 30 µM, 35 µM, 40 µM, 45 µM, 50 µM, 55 µM, 60 µM, 65 µM, 70 µM, 75 µM, 80 µM, 85 µM, 90 µM, 95 µM, 100 µM, 125 µM, 150 µM, 175 µM, 200 µM, 225 µM, 250 µM, 275 µM, 300 µM, 325 µM, 350 µM, 375 µM, 400 µM, 425 µM, 450 µM, 475 µM, and 500 µM. Particularly suitable concentrations of polyphosphorolyzing agent(s) may include but are not limited to approximately 25 µM, 50 µM, and 100 µM, 150 µM, 200 µM and 250 µM. Other suitable concentrations of polyphosphorolyzing agent may also be suitable as would be understood by one of skill in the art, and are also contemplated to be part of this description.

The methods using APP described herein may be carried out in any of several different forms. In some embodiments, the method comprises the following steps carried out serially:
(a) Annealing to the template strand a complementary activatable oligonucleotide "P*". This activatable oligonucleotide has a non-extendable nucleotide at its 3' terminus. It has no nucleotides at or near its 3' terminus that mismatch the corresponding nucleotides on the template strand. Therefore, the terminal nucleotide is hybridized to the template strand when the oligonucleotide P* is annealed.
(b) Polyphosphorolyzing the annealed activatable oligonucleotide P* with at least one polyphosphorolyzing agent described herein and an enzyme that has polyphosphorolysis activity. This activates the oligonucleotide P* by removal of the hybridized terminal nucleotide.
(c) Polymerizing by extending the activated oligonucleotide P* on the template strand in presence of four nucleoside triphosphates and a nucleic acid polymerase to synthesize the desired nucleic acid strand.

The APP method may also be used to amplify a desired nucleic acid strand by, for example, adding the following additional steps: (d) separating the desired nucleic acid strand of step (c) from the template strand, and (e) repeating steps (a)-(d) until a desired level of amplification of the desired nucleic acid strand is achieved. Steps (a) to (c) of APP can be conducted sequentially as two or more temperature stages on a thermocycler, or they can be conducted as one temperature stage on a thermocycler.

As described above, APP may be used to amplify nucleic acid molecules, including but not limited to ribonucleic acid (e.g., RNA) and/or deoxyribonucleic acid (e.g., DNA). When used to amplify DNA, the non-extendable, activatable oligonucleotide P* is typically a 2'-deoxyoligonucleotide, the terminal deoxynucleotide may be a 2',3'-dideoxynucleotide, the four nucleoside triphosphates are 2'-deoxynucleoside triphosphates, and the nucleic acid polymerase is a DNA polymerase. The DNA polymerase used in step (c) can also be the enzyme having polyphosphorolysis activity used in step (b). Amplification by APP may be linear or exponential. Linear amplification is obtained when the activatable oligonucleotide P* is the only complementary oligonucleotide used. Exponential amplification is obtained when a second oligonucleotide is present that is complementary to the desired nucleic acid strand (e.g., as in PCR). The second oligonucleotide can either be an extendable or an activatable non-extendable oligonucleotide. The activatable oligonucleotide P* and the second oligonucleotide flank the region that is targeted for amplification. In step (a), the second oligonucleotide anneals to the separated desired nucleic acid strand product of step (d). In step (c), polymerization extends the second oligonucleotide on the desired nucleic acid strand to synthesize a copy of the nucleic acid template strand. In step (d), the synthesized nucleic acid template strand is separated from the desired nucleic acid strand. Steps (a) through (d) may then be repeated until the desired level exponential amplification has been achieved.

In certain embodiments, the APP method is used for miRNA-specific amplification. The nucleic acid template strand is typically a sense or antisense cDNA strand of one species of miRNA and is present in mixture with the corresponding (sense or antisense) cDNA strand of other miRNA species. The activatable (e.g., non-extendable) oligonucleotide P* has no mismatches near the 3' terminus of the target miRNA cDNA sequence and has at least one nucleotide at or near its 3' terminus that mismatches the corresponding nucleotide of the non-target miRNA species cDNA. Because of the mismatch, in step (a) of the APP method the terminal non-extendable nucleotide of oligonucleotide P* is not hybridized to the non-target miRNA cDNA. In step (b), polyphosphorolysis does not substantially remove the non-hybridized terminal or near terminal nucleotide from the activatable oligonucleotide P* annealed to the non-target miRNA. In step (c), therefore, the oligonucleotide P* is not substantially extended by polymerization on the non-target miRNA cDNA. As a result, the desired nucleic acid strand of the target miRNA cDNA synthesized on the template strand is amplified preferentially over any nucleic acid strand synthesized on the non-target miRNA cDNA. In one embodiment, the APP method is used for exponential amplification of a specific (target) miRNA species in a mixture containing one or more other (non-target) miRNA species. Following the generation of a cDNA ligation product from a polyadenylated miRNA as described herein or the generation of a miRNA ligation product and subsequent reverse transcription to create a cDNA, strands of the cDNAs may be separated to provide single-stranded DNA, followed by the serial steps (a)-(e):

(a) Annealing to the sense or antisense strands of the target and non-target cDNA a complementary activatable 2'-deoxyoligonucleotide P* that has a non-extendable 2',3'-dideoxynucleotide at its 3' terminus. P* has no nucleotides at or near its 3' terminus that mismatch the corresponding 2'-deoxynucleotides on the target cDNA, but has at least one nucleotide at or near its 3' terminus that mismatches the corresponding 2'-deoxynucleotide on the non-target cDNA. Consequently, the terminal 2',3'-dideoxynucleotide is hybridized to the target strand but not to the non-target strand when the oligonucleotide P* is annealed. Simultaneously, a second 2'-deoxyoligonucleotide that is complementary to the anti-parallel strands of each cDNA is annealed to the anti-parallel strands. The activatable 2'-deoxyoligonucleotide P* and the second 2'-deoxyoligonucleotide flank the region of the cDNA to be amplified.

(b) Polyphosphorolyzing the activatable P* that is annealed to a target cDNA strand with at least one polyphosphorolyzing agent and an enzyme that has polyphosphorolysis activity. This activates the P* that is annealed to the target strand by removal of the hybridized terminal 2',3'-dideoxynucleotide. It does not substantially activate the P* that is annealed to the non-target cDNA strand because the non-hybridized terminal 2',3'-dideoxynucleotide is not substantially removed by the polyphosporolysis.

(c) Polymerizing by extending the activated oligonucleotide P* on the target strand in presence of four nucleoside triphosphates and a DNA polymerase and simultaneously extending the second 2'-deoxyoligonucleotide on both target and non-target cDNA anti-parallel strands.

(d) Separating the extension products of step (c);

(e) Repeating steps (a)-(d) until the desired level of exponential amplification of the target cDNA has been achieved.

In certain embodiments, the provided methods for detecting and/or quantitating miRNA comprise the step of target nucleic acid amplification using activation by polyphosphorolysis (APP) in the presence of at least one phosphorolyzing agent. In certain embodiments, the at least one polyphosphorolyzing agent is a diphosphate, a triphosphate, a tetraphosphate, a pentaphosphate or a hexaphosphate. In certain embodiments of the provided methods, the polyphosphorolyzing agent is triphosphate. In certain embodiments of the provided methods, the polyphosphorolyzing agent is hexaphosphate.

In certain embodiments, methods for amplifying target nucleic acids use activation by pyrophosphorolysis-activated polymerization (PAP) reactions. PAP may be used to polymerize and/or amplify nucleic acid molecules, including but not limited to ribonucleic acid (e.g., RNA) and/or deoxyribonucleic acid (e.g., DNA), or hybrids thereof. PAP reactions and uses thereof in polymerization and amplification reactions is described, for example, in U.S. Pat. No. 7,033,763, herein incorporated by reference in its entirety. In PAP, the annealed activatable oligonucleotide P* is pyrophosphorolyzed with pyrophosphate and an enzyme that exhibits polyphosphorolyzing activity. This activates the oligonucleotide P* by removal of the hybridized non-extendible 3' terminus. Accordingly, in certain embodiments, amplification of the target miRNA cDNA uses PAP and pyrophosphate as the pyrophosphorolyzing agent.

In certain embodiments, for target nucleic acid amplification reactions using APP or PAP, a forward primer or a reverse primer comprises a non-extendible nucleotide at the 3' terminus. In certain embodiments, for target nucleic acid amplification reactions using APP or PAP, both a forward primer and a reverse primer comprises a non-extendible nucleotide at the 3' terminus.

In one embodiment, the amplification reaction is a 5'-nuclease assay (also commercially known as TaqMan® assays) performed using a nucleic acid polymerase, such as DNA polymerase, RNA polymerase, and reverse transcriptase, at least one oligonucleotide primer capable of specifically hybridizing to a target polynucleotide (from which the amplified target nucleic acid is amplified), at least one detectable probe that hybridizes to the amplified target nucleic acid, and which may be incorporated into the at least one primer), and at least one detectable nucleic acid binding agent (e.g., an intercalating or non-intercalating dye) which may be introduced before, during or after amplification. The probe typically contains a detectable label emitting a signal that may be monitored to ascertain whether the target nucleic acid has been amplified. In some embodiments, the probe is an oligonucleotide that hybridizes to the target nucleic acid 3' relative to the at least one primer. In some embodiments, the polymerase has nuclease activity (i.e., 5'-to-3' nuclease activity) for releasing the probe from the amplified nucleic acid. In some embodiments, release from the amplified nucleic acid renders the probe detectable. In some embodiments, the probe comprises a detectable label and a quencher molecule that quenches the detectable label when free but does not quench when the probe is hybridized to the amplified nucleic acid. In some embodiments, two or more probes may be used where at least one probe has a detectable label and at least one other probe has a quencher molecule. When in sufficiently close proximity to one another, the quencher molecule typically suppresses the signal of the detectable label on the other probe. In some embodiments, two or more probes, each having a different detectable label, can be used without quencher molecules. In such embodiments, the probes are rendered detectable, either de novo or by exhibiting a different signal than either probe alone, when in sufficiently close proximity to one another. Typically, the detectable label and quencher molecule are part of a single probe. As amplification proceeds, the polymerase digests the probe to separate the detectable label from the quencher molecule. The detectable label (e.g., fluorescence) is monitored during the reaction, where detection of the label corresponds to the occurrence of nucleic acid amplification (i.e., the higher the signal the greater the amount of amplification). Variations of TaqMan® assays, such as LNA™ spiked TaqMan® assay, are known in the art and would be suitable for use in the methods described herein.

Any of several methods can be used to detect amplified target nucleic acids using primers or probes. Many different reagents, systems, or detectable labels can be used in the methods described herein. These include, for example, TaqMan® systems, detectable label-quencher systems (e.g., FRET, salicylate/DTPA ligand systems (see, e.g., Oser, et al. Angew. Chem. Int. Ed. Engl. 29:1167-1169 (1990), displacement hybridization, homologous probes, assays described in EP 070685), molecular beacons (e.g., NASBA®), locked nucleic acid (LNA) bases (Singh, et al. Chem. Commun 4:455-456 (1998)), peptide nucleic acid (PNA) probes (Pellestor, et al. Eur. J. Hum. Gen. 12:694-700 (2004)), Eclipse probes (Afonina, et al. Biotechniques 32:940-949 (2002)), light-up probes (Svanvik, et al. Anal. Biochem. 281:26-35 (2000)), molecular beacons (Tyagi, et al. Nat. Biotechnol. 14:303-308 (1996)), tripartite molecular beacons (Nutiu, et al. Nucleic Acids Res. 30:E94 (2002)), QuantiProbes (www.qiagen.com), HyBeacons (French, et al. Mol. Cell. Probes 15:363-374 (2001)), displacement probes (Li, et al. Nucleic Acids Res. 30:E5 (2002)), HybProbes (Cardullo, et al. Proc. Natl. Acad. Sci. USA 85:8790-8794 (1988)), MGB Alert (www.nanogen.com), Q-PNA (Fiandaca, et al. Genome Res. 11:609-613 (2001)), Plexor (www.Promega.com), LUX™ primers (Nazarenko, et al. Nucleic Acids Res. 30:E37 (2002)), Scorpion® primers (Whitcombe, et al. Nat. Biotechnol. 17:804-807 (1999)), AmpliFluor® (Sunrise) primers (Nazarenko, et al. Nucleic Acids Res. 25:2516-2521 (1997)), DzyNA primers (Todd, et al. Clin. Chem. 46:625-630 (2000)), and the like. In each of these assays, the generation of amplification products can be monitored while the reaction is in progress. An apparatus for detecting the signal generated by the detectable label can be used to detect, measure, and quantify the signal before, during, or after amplification. The particular type of signal may dictate the choice of detection method. For example, in some embodiments, fluorescent dyes are used to label probes or amplified products. The probes bind to single-stranded or double-stranded amplified products, or the dyes intercalate into the double-stranded amplified products, and consequently, the resulting fluorescence increases as the amount of amplified product increases. The use of other methods or reagents is also contemplated herein as would be understood by one of skill in the art.

Another exemplary system utilizes double-stranded probes in displacement hybridization methods (see, e.g., Morrison, et al. Anal. Biochem. 183:231-244 (1989); and Li, et al. (supra)). In such methods, the probe typically includes two complementary oligonucleotides of different lengths where one includes a detectable label and the other includes a quencher molecule. When not bound to a target nucleic acid, the quencher suppresses the signal from the detectable label. The probe becomes detectable upon displacement hybridization with a target nucleic acid. Multiple probes can be used, each containing different detectable labels, such that multiple target nucleic acids can be queried in a single reaction.

Additional exemplary methods for amplifying and detecting target nucleic acids involve "molecular beacons", which are single-stranded hairpin shaped oligonucleotide probes. In the presence of the target sequence, the probe unfolds, binds and emits a signal (e.g., fluoresces). A molecular beacon typically includes at least four components: 1) the "loop", an 18-30 nucleotide region which is complementary to the target sequence; 2) two 5-7 nucleotide "stems" found on either end of the loop and being complementary to one another; 3) at the 5' end, a detectable label; and 4) at the 3' end, a quencher molecule that prevents the detectable label from emitting a single when the probe is in the closed loop shape (i.e., not bound to a target nucleic acid). Thus, in the presence of a complementary target, the "stem" portion of the beacon separates out resulting in the probe hybridizing to the target. Other types of molecular beacons are also known and can be suitable for use in the methods described herein. Molecular beacons can be used in a variety of assay systems. One such system is nucleic acid sequence-based amplification (NASBA®), a single step isothermal process for amplifying RNA to double stranded DNA without temperature cycling. A NASBA® reaction typically requires avian myeloblastosis virus (AMV), reverse transcriptase (RT), T7 RNA polymerase, RNase H, and two oligonucleotide primers. After amplification, the amplified target nucleic acid can be detected using a molecular beacon. Other uses for molecular beacons are known in the art and would be suitable for use in the methods described herein.

The Scorpion® system is another exemplary assay format that may be used in the methods described herein. Scorpion® primers are bi-functional molecules in which a primer is covalently linked to the probe, along with a detectable label (e.g., a fluorophore) and a quencher. In the presence of a target nucleic acid, the detectable label and the quencher separate which leads to an increase in signal emitted from the detectable label. Typically, a primer used in the amplification reaction includes a probe element at the 5' end along with a "PCR blocker" element (such as an HEG monomer) at the start of the hairpin loop. The probe typically includes a self-complementary stem sequence with a detectable label at one end and a quencher at the other. In the initial amplification cycles, the primer hybridizes to the target and extension occurs due to the action of polymerase. The Scorpion® system can be used to examine and identify point mutations using multiple probes with different tags to distinguish between the probes. Using PCR as an example, after one extension cycle is complete, the newly synthesized target region is attached to the same strand as the probe. Following the second cycle of denaturation and annealing, the probe and the target hybridize. The hairpin sequence then hybridizes to a part of the newly produced PCR product. This results in the separation of the detectable label from the quencher and causes emission of the signal. Other uses for Scorpion® primers are known in the art and would be suitable for use in the methods described herein.

One or more detectable labels or quenching agents are typically attached to a primer or probe. The detectable label may emit a signal when free or when bound to one the target nucleic acid. The detectable label may also emit a signal when in proximity to another detectable label. Detectable labels may also be used with quencher molecules such that the signal is only detectable when not in sufficiently close proximity to the quencher molecule. For instance, in some embodiments, the assay system may cause the detectable label to be liberated from the quenching molecule. Any of several detectable labels may be used to label the primers and probes used in the methods described herein. As mentioned above, in some embodiments the detectable label can be attached to a probe which may be incorporated into a primer or may otherwise bind to amplified target nucleic acid (for example, a detectable nucleic acid binding agent such as an intercalating or non-intercalating dye). When using more than one detectable label, each label should differ in its spectral properties such that the labels may be distinguished from each other, or such that together the detectable labels emit a signal that is not emitted by either detectable label alone. Exemplary detectable labels include, but are not limited to, a fluorescent dye or fluorophore (i.e., a chemical group that may be excited by light to emit fluorescence or phosphorescence), "acceptor dyes" capable of quenching a fluorescent signal from a fluorescent donor dye, and the like.

Suitable detectable labels include, for example, fluoresceins (e.g., 5-carboxy-2,7-dichlorofluorescein; 5-Carboxyfluorescein (5-FAM); 5-HAT (Hydroxy Tryptamine); 6-HAT; 6-JOE; 6-carboxyfluorescein (6-FAM); FITC); Alexa fluors (e.g., 350, 405, 430, 488, 500, 514, 532, 546, 555, 568, 594, 610, 633, 635, 647, 660, 680, 700, 750); BODIPY® fluorophores (e.g., 492/515, 493/503, 500/510, 505/515, 530/550, 542/563, 558/568, 564/570, 576/589, 581/591, 630/650-X, 650/665-X, 665/676, FL, FL ATP, Fl-Ceramide, R6G SE, TMR, TMR-X conjugate, TMR-X, SE, TR, TR ATP, TR-X SE), coumarins (e.g., 7-amino-4-methylcoumarin, AMC, AMCA, AMCA-S, AMCA-X, ABQ, CPM methylcoumarin, coumarin phalloidin, hydroxycoumarin, CMFDA, methoxycoumarin), calcein, calcein AM, calcein blue, calcium dyes (e.g., calcium crimson, calcium green, calcium orange, calcofluor white), Cascade Blue, Cascade Yellow; CyTM dyes (e.g., 3, 3.18, 3.5, 5, 5.18, 5.5, 7), cyan GFP, cyclic AMP Fluorosensor (Fi-CRhR), fluorescent proteins (e.g., green fluorescent protein (e.g., GFP. EGFP), blue fluorescent protein (e.g., BFP, EBFP, EBFP2, Azurite, mKalama1), cyan fluorescent protein (e.g., ECFP, Cerulean, CyPet), yellow fluorescent protein (e.g., YFP, Citrine, Venus, YPet), FRET donor/acceptor pairs (e.g., fluorescein/tetramethylrhodamine, IAEDANS/fluorescein, EDANS/dabcyl, fluorescein/fluorescein, BODIPY® FL/BODIPY® FL, Fluorescein/QSY7 and QSY9), LysoTracker® and LysoSensor™ (e.g., LysoTracker® Blue DND-22, LysoTracker® Blue-White DPX, LysoTracker® Yellow HCK-123, LysoTracker® Green DND-26, LysoTracker® Red DND-99, LysoSensor™ Blue DND-167, LysoSensor™ Green DND-189, LysoSensor™ Green DND-153, LysoSensor™ Yellow/Blue DND-160, LysoSensor Yellow/Blue 10,000 MW dextran), Oregon Green (e.g., 488, 488-X, 500, 514); rhodamines (e.g., 110, 123, B, B 200, BB, BG, B extra, 5-carboxytetramethylrhodamine (5-TAMRA), 5 GLD, 6-Carboxyrhodamine 6G, Lissamine, Lissamine Rhodamine B, Phallicidine, Phalloidine, Red, Rhod-2, 5-ROX (carboxy-X-rhodamine), Sulphorhodamine B can C, Sulphorhodamine G Extra, Tetramethylrhodamine (TRITC), WT), Texas Red, Texas Red-X, VIC and other labels described in, e.g., US Pub. No. 2009/0197254), among others as would be known to those of skill in the art. Other detectable labels can also be used (see, e.g., U.S. Patent Application Publication No. 2009/0197254), as would be known to those of skill in the art.

As used herein "polymerase" refers to any enzyme having a nucleotide polymerizing activity. Polymerases (including DNA polymerases and RNA polymerases) useful in accordance with the present teachings include, but are not limited to, commercially available or natural DNA-directed DNA polymerases, DNA-directed RNA polymerases, RNA-directed DNA polymerases, and RNA-directed RNA polymerases. Polymerases used in accordance with the invention may be any enzyme that can synthesize a nucleic acid molecule from a nucleic acid template, typically in the 5' to 3' direction.

Exemplary DNA polymerases that may be used in the methods, kits and compositions provided herein include, but are not limited to: *Thermus thermophilus* (Tth) DNA polymerase, *Thermus aquaticus* (Taq) DNA polymerase, *Thermotoga neopolitana* (Tne) DNA polymerase, *Thermotoga maritima* (Tma) DNA polymerase, *Thermococcus litoralis* (Tli or VENT™) DNA polymerase, *Pyrococcus furiosus* (Pfu) DNA polymerase, DEEPVENT™ DNA polymerase, *Pyrococcus woosii* (Pwo) DNA polymerase, *Bacillus sterothermophilus* (Bst) DNA polymerase, *Bacillus caldophilus* (Bca) DNA polymerase, *Sulfolobus acidocaldarius* (Sac) DNA polymerase, *Thermoplasma acidophilum* (Tac) DNA polymerase, *Thermus flavus* (Tfl/Tub) DNA polymerase, *Thermus ruber* (Tru) DNA polymerase, *Thermus brockianus* (DYNAZYME™) DNA polymerase, *Methanobacterium thermoautotrophicum* (Mth) DNA polymerase, *mycobacterium* DNA polymerase (Mtb, Mlep), and mutants, and variants and derivatives thereof. RNA polymerases such as T3, T5 and SP6 and mutants, variants and derivatives thereof may also be used in accordance with the present teachings. Generally, any type I DNA polymerase may be used in accordance with the present teachings although other DNA polymerases may be used including, but not limited to, type III or family A, B, C etc., DNA polymerases.

The nucleic acid polymerases used in the methods, kits and compositions provided herein may be mesophilic or thermophilic. Exemplary mesophilic DNA polymerases include T7 DNA polymerase, T5 DNA polymerase, Klenow fragment DNA polymerase, DNA polymerase III and the like. Exemplary thermostable DNA polymerases include Taq, Tne, Tma, Pfu, Tfl, Tth, Stoffel fragment, VENT™ and DEEPVENT™ DNA polymerases, and mutants, variants and derivatives thereof (U.S. Pat. Nos. 5,436,149; 4,889,818; 4,965,188; 5,079,352; 5,614,365; 5,374,553; 5,270,179; 5,047,342; and 5,512,462; PCT Application Publication Nos. WO 92/06188, WO 92/06200, and WO 96/10640; Barnes, Gene 112:29-35 (1992); Lawyer, et al., PCR Meth. Appl. 2:275-287 (1993); Flaman, et al., Nucl. Acids Res. 22:3259-3260 (1994)). Examples of DNA polymerases substantially lacking in 3' exonuclease activity include, but are not limited to, Taq, Tne (exo-), Tma (exo-), Pfu (exo-), Pwo (exo-) and Tth DNA polymerases, and mutants, variants and derivatives thereof.

DNA polymerases for use in the present teachings may be obtained commercially, for example, from Life Technologies Corp. (Carlsbad, Calif.), Pharmacia (Piscataway, N.J.), Sigma (St. Louis, Mo.) and Boehringer Mannheim. Exemplary commercially available DNA polymerases for use in the present disclosure include, but are not limited to, Tsp DNA polymerase from Life Technologies Corp.

A hybridization method may also be used to assay the ligation product. Non-limiting examples of suitable hybridization methods include nucleic acid microarray. Microarray analyses may be performed using commercially available equipment and following the manufacturer's protocols. Typically, single-stranded nucleic acids are attached (arrayed) to a microchip surface. The arrayed sequences are then hybridized (probed) with nucleic acids, which may be fluorescently labeled. After stringent washing to remove the non-specifically bound nucleic acids, the chip surface is generally scanned by confocal laser microscopy or by another detection method, such as CCD camera. Methods of analysis of the raw fluorescent data are known in the art. A variety of arrayed nucleic acid and probe combinations may be used to detect the ligation product of the present teachings.

The 5' and 3' ligation adaptors may be free in solution, such that the mature small RNA is detected in solution. Alternatively, the 5' ligation adaptor or the 3' ligation adaptor may be attached to a solid support, whereby the 3'-terminal end of the 5' ligation adaptor or the 5' terminal end of the 3' ligation adaptor is free. Thus, in this embodiment, the mature small RNA or cDNA thereof is attached to the ligation adaptor that is attached to the solid support. The mature small RNA or cDNA thereof may hybridize to the immobilized ligation adaptor and be ligated when indirectly attached to the solid support. In other embodiments, the universal RT primer comprising a poly(T) portion may be attached to a solid support, whereby the 3'-terminal end of the universal RT primer is free. Thus, in this embodiment, the cDNA of the small RNA extended from the universal primer is attached to the solid support. Non-limiting examples of a suitable solid support include a glass surface, a silica surface, a plastic surface, a polymer surface, a co-polymer surface or a metal surface.

As used herein, the term "next generation sequencing" or "NGS" generally refers to high throughput sequencing technologies, including, but not limited to, massively parallel signature sequencing, high throughput sequencing, sequencing by ligation (e.g., SOLiD sequencing), proton ion semiconductor sequencing, DNA nanoball sequencing, single molecule sequencing, and nanopore sequencing.

As used herein, the term "reaction vessel" generally refers to any container in which a reaction can occur in accordance with the present teachings. In some embodiments, a reaction vessel may be a microcentrifuge tube and other containers of the sort in common practice in modern molecular biology laboratories. In some embodiments, a reaction vessel may be a well in a microtitre plate, a spot on a glass slide, or a spot in an Applied Biosystems TaqMan® Array Card (Life Technologies, Foster City, Calif.). For example, a plurality of reaction vessels may reside on the same support. In some embodiments, lab-on-a-chip-like devices, available for example from Caliper and Fluidigm, can provide for reaction vessels. In some embodiments, various microfluidic approaches may be employed. It will be recognized that a variety of reaction vessels are available in the art and fall within the scope of the present teachings.

In certain embodiments, compositions are provided that comprise a universal 5' ligation adaptor, a universal 3' ligation adaptor, a 5' semi-degenerate ligation splint and a 3' semi-degenerate ligation splint. In certain embodiments, compositions are provided that further comprise a universal forward and RT/reverse primer pair. In certain embodiments, compositions are provided that further comprise a blocking oligonucleotide. In certain embodiments, such compositions are reaction compositions.

In certain embodiments, compositions are provided that comprise a universal RT primer comprising a poly(T) portion, a universal 3' ligation adaptor, and a 3' semi-degenerate ligation splint. In certain embodiments, compositions are provided that further comprise a universal forward and reverse primer pair. In certain embodiments, compositions are provided that comprise a universal 3' ligation adaptor, a 3' ligation splint, and a universal forward and reverse primer pair. In certain embodiments, compositions are provided that further comprise a blocking oligonucleotide. In certain embodiments, such compositions are reaction compositions.

In certain embodiments, the present teachings also provide kits designed to expedite performing certain methods. In some embodiments, kits serve to expedite the performance of the methods of interest by assembling two or more components used in carrying out the methods. In some embodiments, kits may contain components in pre-measured unit amounts to minimize the need for measurements by end-users. In some embodiments, kits may include instructions for performing one or more methods of the present teachings. In certain embodiments, the kit components are optimized to operate in conjunction with one another.

In certain embodiments, the present teachings provide a kit comprising a 5' ligation adaptor, a 3' ligation adaptor, a 5' ligation splint and a 3' ligation splint. In certain embodiments, the present teachings provide a kit comprising a universal RT primer comprising an poly(T) portion, a 3' ligation adaptor, and a 3' ligation splint. In certain embodiments, the kits may further comprise one or more of a ligase, a reverse transcriptase, and a DNA polymerase. In some embodiments, the kits may comprise a universal primer pair. In some embodiments, the kits may further comprise primer pairs specific for one or more mature small RNA. In some embodiments, the kits may comprise a plurality of primer pairs, wherein each primer pair is in one reaction vessel of a plurality of reaction vessels. In some embodiments, the kits may comprise a detector probe. In some embodiments, the detector probe comprises a nucleotide of the 5' linker or the 3' linker in the amplification product or a nucleotide of the 5' or 3' linker complement in the amplification product and the detector probe further comprises a nucleotide of the 3' end region of the mature small RNA or a nucleotide of the 5' end region of the mature small RNA in the amplification product or a nucleotide of the 3' end region of the mature small RNA or a nucleotide of the 5' end region of the mature small RNA complement in the amplification product. In certain embodiments, the kit may further comprise a blocking oligonucleotide.

The methods provided herein are of use in detecting or quantitating mature small RNA in a sample. In some embodiments, the methods provided may be used to detect and/or distinguish a specific species of mature small RNA from among other species of small RNAs in the sample. In some embodiments, the methods provided may be used to distinguish several miRNAs from one another in a sample essentially concurrently in a single assay. In certain embodiments, the methods provided can detect very low quantities of small mature RNA in a sample. For example, in certain embodiments, the provided methods can detect fewer than about 1500 copies of an miRNA in a sample. In certain embodiments, the provided methods can detect fewer than about 1000 copies, fewer than about 800 copies, fewer than about 600 copies, fewer than about 400 copies, fewer than about 300 copies, fewer than about 200 copies, fewer than about 100 copies, fewer than about 60 copies, fewer than about 30 copies of an miRNA in a sample. In certain embodiments, the provided methods can detect as few as about 20 copies to about 1500 copies of an miRNA in a sample. Additional sensitivity ranges of certain embodiments of the provided methods include, but are not limited to, detection of about 20 copies to about 1000 copies, about 20 copies to about 600 copies, about 20 copies to about 300 copies, about 20 copies to about 100 copies, and about 20 copies to about 60 copies of an miRNA in a sample. In certain embodiments, the provided methods can detect as few as: about 1000 copies to about 1500 copies, about 500 copies to about 1000 copies, about 50 copies to about 500 copies, about 50 copies to about 200 copies, or about 50 copies to about 100 copies of an miRNA in a sample. In certain embodiments, the provided methods can detect as few as about 600 copies of an miRNA in a sample. In certain embodiments, the provided methods can detect as few as about 60 copies of an miRNA in a sample.

In certain embodiments, the provided methods can detect less than about 0.01 pM of an miRNA in a sample. In certain embodiments, the provided methods can detect less than about 0.001 pM of an miRNA in a sample. In certain embodiments, the provided methods can detect less than about 0.0001 pM of an miRNA in a sample. In certain embodiments, the provided methods can detect in the range of about 0.0001 pM to about 0.01 pM miRNA in a sample. In certain embodiments, the provided methods can detect in the range of about 0.0001 pM to about 0.001 pM miRNA in a sample. In certain embodiments, the provided methods can detect in the range of about 0.001 pM to about 0.01 pM miRNA in a sample. In certain embodiments, the provided methods can detect about 0.01 pM miRNA in a sample. In certain embodiments, the provided methods can detect in about 0.001 pM miRNA in a sample. In certain embodiments, the provided methods can detect about 0.0001 pM miRNA in a sample. According to another embodiment of the present teachings, the methods disclosed herein may be used in diagnostic and/or prognostic methods for identifying diseases and/or in determining patient response to treatment with certain drugs, medications or methods of therapy. An exemplary condition that can be associated with mature small RNAs such as miRNA is cancer. Thus, the present teachings provide a method of diagnosing susceptibility to a cancer, prognosis of outcome for treatment of cancer, or the stage and/or identity of the cancer based on the miRNA profile of the sample.

The prognostic methods of the present teachings are useful for determining if a patient is at risk for recurrence. Cancer recurrence is a concern relating to a variety of types of cancer. For example, of patients undergoing complete surgical removal of colon cancer, 25-40% of patients with stage II colon carcinoma and about 50% of patients with stage III colon carcinoma experience cancer recurrence. One explanation for cancer recurrence is that patients with relatively early stage disease, for example, stage II or stage III, already have small amounts of cancer spread outside of the affected organ that were not removed by surgery. These cancer cells, referred to as micrometastases, cannot typically be detected with currently available tests.

The prognostic methods disclosed herein can be used to identify surgically treated patients likely to experience cancer recurrence so that they can be offered additional therapeutic options, including preoperative or postoperative adjuncts such as chemotherapy, radiation, biological modifiers and other suitable therapies. The methods are especially effective for determining the risk of metastasis in patients who demonstrate no measurable metastasis at the time of examination or surgery.

The prognostic methods according to certain embodiments also are useful for determining a proper course of treatment for a patient having cancer. A course of treatment refers to the therapeutic measures taken for a patient after diagnosis or after treatment for cancer. For example, a determination of the likelihood for cancer recurrence, spread, or patient survival, can assist in determining whether a more conservative or more radical approach to therapy should be taken, or whether treatment modalities should be combined. For example, when cancer recurrence is likely, it can be advantageous to precede or follow surgical treatment with chemotherapy, radiation, immunotherapy, biological modifier therapy, gene therapy, vaccines, and the like, or adjust the span of time during which the patient is treated.

Exemplary cancers that may be evaluated using a method as disclosed herein include, but are not limited to hematopoietic neoplasms, Adult T-cell leukemia/lymphoma, Lymphoid Neoplasms, Anaplastic large cell lymphoma, Myeloid Neoplasms, Histiocytoses, Hodgkin Diseases (HD), Precursor B lymphoblastic leukemia/lymphoma (ALL), Acute myelogenous leukemia (AML), Precursor T lymphoblastic leukemia/lymphoma (ALL), Myelodysplastic syndromes, Chronic Myeloproliferative disorders, Chronic lymphocytic leukemia/small lymphocytic lymphoma (SLL), Chronic Myelogenous Leukemia (CML), Lymphoplasmacytic lymphoma, Polycythemia Vera, Mantle cell lymphoma, Essential Thrombocytosis, Follicular lymphoma, Myelofibrosis with Myeloid Metaplasia, Marginal zone lymphoma, Hairy cell leukemia, Hemangioma, Plasmacytoma/plasma cell myeloma, Lymphangioma, Glomangioma, Diffuse large B-cell lymphoma, Kaposi Sarcoma, Hemanioendothelioma, Burkitt lymphoma, Angiosarcoma, T-cell chronic lymphocytic leukemia, Hemangiopericytoma, Large granular lymphocytic leukemia, head & neck cancers, Basal Cell Carcinoma, Mycosis fungoids and sezary syndrome, Squamous Cell Carcinoma, Ceruminoma, Peripheral T-cell lymphoma, Osteoma, Nonchromaffin Paraganglioma, Angioimmunoblastic T-cell lymphoma, Acoustic Neurinoma, Adenoid Cystic Carcinoma, Angiocentric lymphoma, Mucoepidermoid Carcinoma, NK/T-cell lymphoma, Malignant Mixed Tumors, Intestinal T-cell lymphoma, Adenocarcinoma, Malignant Mesothelioma, Fibrosarcoma, Sarcomotoid Type lung cancer, Osteosarcoma, Epithelial Type lung cancer, Chondrosarcoma, Melanoma, cancer of the gastrointestinal tract, olfactory Neuroblastoma, Squamous Cell Carcinoma, Isolated Plasmocytoma, Adenocarcinoma, Inverted Papillomas, Carcinoid, Undifferentiated Carcinoma, Malignant Melanoma, Mucoepidermoid Carcinoma, Adenocarcinoma, Acinic Cell Carcinoma, Gastric Carcinoma, Malignant Mixed Tumor, Gastric Lymphoma, Gastric Stromal Cell Tumors, Amenoblastoma, Lymphoma, Odontoma, Intestinal Stromal Cell tumors, thymus cancers, Malignant Thymoma, Carcinids, Type I (Invasive thymoma), Malignant Mesethelioma, Type II (Thymic carcinoma), Non-mucin producing adenocarcinoma, Squamous cell carcinoma, Lymph epithelioma, cancers of the liver and biliary tract, Squamous Cell Carcinoma, Hepatocellular Carcinoma, Adenocarcinoma, Cholangiocarcinoma, Hepatoblastoma, papillary cancer, Angiosarcoma, solid Bronchioalveolar cancer, Fibrolameller Carcinoma, Small Cell Carcinoma, Carcinoma of the Gallbladder, Intermediate Cell carcinaoma, Large Cell Carcinoma, Squamous Cell Carcinoma, Undifferentiated cancer, cancer of the pancreas, cancer of the female genital tract, Squamous Cell Carcinoma, Cystadenocarcinoma, Basal Cell Carcinoma, Insulinoma, Melanoma, Gastrinoma, Fibrosarcoma, Glucagonamoa, Intraepithelial Carcinoma, Adenocarcinoma Embryonal, cancer of the kidney, Rhabdomysarcoma, Renal Cell Carcinoma, Large Cell Carcinoma, Nephroblastoma (Wilm's tumor), Neuroendocrine or Oat Cell carcinoma, cancer of the lower urinary tract, Adenosquamous Carcinoma, Urothelial Tumors, Undifferentiated Carcinoma, Squamous Cell Carcinoma, Carcinoma of the female genital tract, Mixed Carcinoma, Adenoacanthoma, Sarcoma, Small Cell Carcinoma, Carcinosarcoma, Leiomyosarcoma, Endometrial Stromal Sarcoma, cancer of the male genital tract, Serous Cystadenocarcinoma, Mucinous Cystadenocarcinoma, Sarcinoma, Endometrioid Tumors, Speretocytic Sarcoma, Embryonal Carcinoma, Celioblastoma, Choriocarcinoma, Teratoma, Clear Cell Carcinoma, Leydig Cell Tumor, Unclassified Carcinoma, Sertoli Cell Tumor, Granulosa-Theca Cell Tumor, Sertoli-Leydig Cell Tumor, Disgerminoma, Undifferentiated Prostatic Carcinoma, Teratoma, Ductal Transitional carcinoma, breast cancer, Phyllodes Tumor, cancer of the bones joints and soft tissue, Paget's Disease, Multiple Myeloma, In situ Carcinoma, Malignant Lymphoma, Invasive Carcinoma, Chondrosarcoma, Mesenchymal Chondrosarcoma, cancer of the endocrine system, Osteosarcoma, Adenoma, Ewing Tumor, endocrine Carcinoma, Malignant Giant Cell Tumor, Meninginoma, Adamantinoma, Craniopharlingioma, Malignant Fibrous Histiocytoma, Papillary Carcinoma, Histiocytoma, Follicular Carcinoma, Desmoplastic Fibroma, Medullary Carcinoma, Fibrosarcoma, Anoplastic Carcinoma, Chordoma, Adenoma, Hemangioendothelioma, Memangispericytoma, Pheochromocytoma, Liposarcoma, Neuroblastoma, Paraganglioma, Histiocytoma, Pineal cancer, Rhabdomysarcoma, Pineoblastoma, Leiomyosarcoma, Pineocytoma, Angiosarcoma, skin cancer, cancer of the nervous system, ovarian cancer, prostate cancer, liver cancer, stomach cancer, Melanoma, Schwannoma, Squamous cell carcinoma, Neurofibroma, Basal cell carcinoma, Malignant Peripheral Nerve Sheath Tumor, Merkel cell carcinoma, Sheath Tumor, Extramamary Paget's Disease, Astrocytoma, Paget's Disease of the nipple, Fibrillary Astrocytoma, Glioblastoma Multiforme, Brain Stem Glioma, Cutaneous T-cell lymphoma, Pilocytic Astrocytoma, Xanthorstrocytoma, Histiocytosis, Oligodendroglioma, Ependymoma, Gangliocytoma, Cerebral Neuroblastoma, Central Neurocytoma, Dysembryoplastic Neuroepithelial Tumor, Medulloblastoma, Malignant Meningioma, Primary Brain Lymphoma, Primary Brain Germ Cell Tumor, cancers of the eye, Squamous Cell Carcinoma, Mucoepidermoid Carcinoma, Melanoma, Retinoblastoma, Glioma, Meningioma, cancer of the heart, Myxoma, Fibroma, Lipoma, Papillary Fibroelastoma, Rhasdoyoma, or Angiosarcoma among others.

While the present teachings have been described in terms of these exemplary embodiments, the skilled artisan will readily understand that numerous variations and modifications of these exemplary embodiments are possible without undue experimentation. All such variations and modifications are within the scope of the current teachings. Aspects of the present teachings may be further understood in light of the following examples, which should not be construed as limiting the scope of the teachings in any way.

EXAMPLES

Example 1: miRNA Analysis Using Dual-End Ligation-Based RT-qPCR (3-Step Method)

Total RNAs from human brain were obtained from Ambion® (Carlsbad, Calif.). Ligation adaptor, primer and synthetic oligonucleotides were purchased from Integrated DNA Technologies (IDT, Coralville, Iowa). TaqMan® assays were obtained from Applied Biosystems® Custom Gene Expression Laboratory.

Ligation Reaction

The ligation reaction was performed to ligate the 5' and 3' ligation adaptors to the miRNA in the presence of the 5' and 3' ligation splints with semi-degenerate overhangs. The ligation reaction was performed by combining the following components:

| |
|---|
| 2 μl 5 × Adaptor Mix |
| 5 μl 2 × Ligation Buffer |
| 1 μl 10 × Ligation Enzyme Mix |
| 2 μl total RNA ranging from 2 pg to 20 ng |
| 10 μl Total ligation reaction volume |

The ligation reaction mix was mixed, spun briefly, and incubated in a thermal cycler at 37° C. for 30 min.

Reverse Transcription Reaction

The reverse transcription (RT) step allows synthesis of the first strand cDNA from the ligation product as template. The RT reaction was performed by combining the following components:

| |
|---|
| 2 μl 10 × RT Buffer |
| 4 μl 25 mM MgCl$_2$ |
| 2 μl 0.1M DTT |
| 1 μl 40 U/(μl RNaseOUT ™ |
| 0.2 μl 100 mM dNTP |
| 0.2 μl 100 × Universal RT primer |
| 0.5 μl 200 U/μl SuperScript ™ III |
| 0.1 μl nuclease-free water |
| 10 μl ligation reaction |
| 20 μl Total RT reaction volume |

The RT reaction was mixed, spun briefly, and incubated in a thermal cycler at 50° C. for 50 min, 85° C. for 5 min, 4° C. hold.

Pre-Amplification Reaction

Pre-amplification (pre-amp) is an optional step to increase sensitivity for detection. The pre-amp reaction was performed by combining the following components:

| |
|---|
| 12.5 μl 2 × TaqMan ® Pre-amp Master Mix |
| 2.5 μl 10 × Pre-amp Universal Primers |
| 7.5 μl nuclease-free water |
| 2.5 μl cDNA from RT reaction mix |
| 25 μl Total pre-amp reaction volume |

The pre-amp reaction was mixed, spun briefly and incubated in a thermal cycler at 95° C. for 10 min, followed by 12 cycles of (95° C. for 15 sec, 60° C. for 2 min), followed by 99° C. for 10 min and a 4° C. hold.

Polymerase Chain Reaction (PCR)

Real-time PCR was performed for the detection of the target miRNA. The RT or pre-amp reactions were diluted at 1:10, 1:50 or 1:100 in nuclease-free water. The PCR reaction was prepared by combining the following components:

| |
|---|
| 10 μl 2 × TaqMan ® Universal Master Mix II |
| 1 μl 20x TaqMan ® Assay |
| 4 μl nuclease-free water |
| 5 μl diluted RT or pre-amp reaction |
| 20 μl Total PCR reaction volume |

The PCR reaction was mixed and spun briefly. The reactions were run with a real-time PCR system, such as the ABI PRISM® 7900HT Sequence Detection System or the ViiA™7 Real-Time PCR System. The data was analyzed according to the instrument specifications and guidelines.

Figure 7:
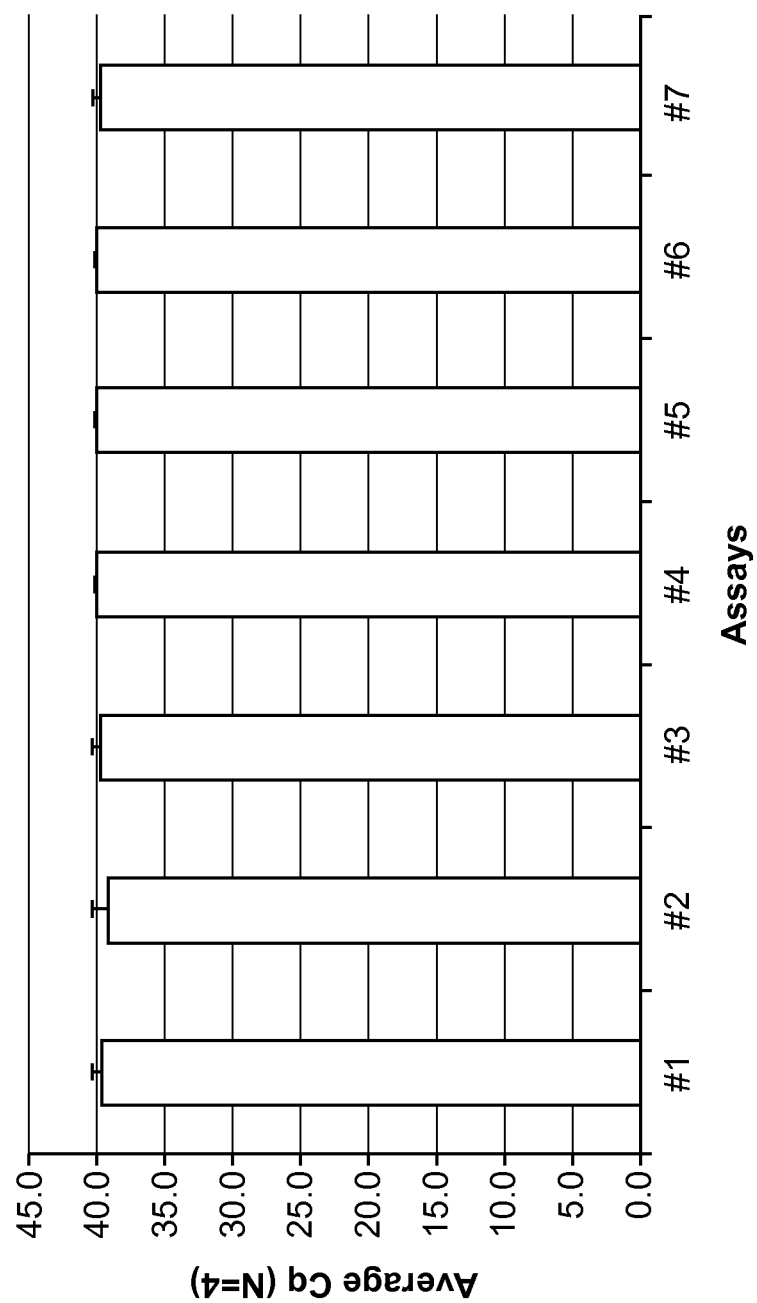
FIG. 7 graphically represents the background signal observed when the sample was substituted with nuclease-free water in the ligation reaction in methods according to the embodiments of the present teachings.

As can be seen in FIG. 7, no or minimal background signal was detected when the miRNA sample was substituted with nuclease-free water in the ligation reaction.

Figure 8:
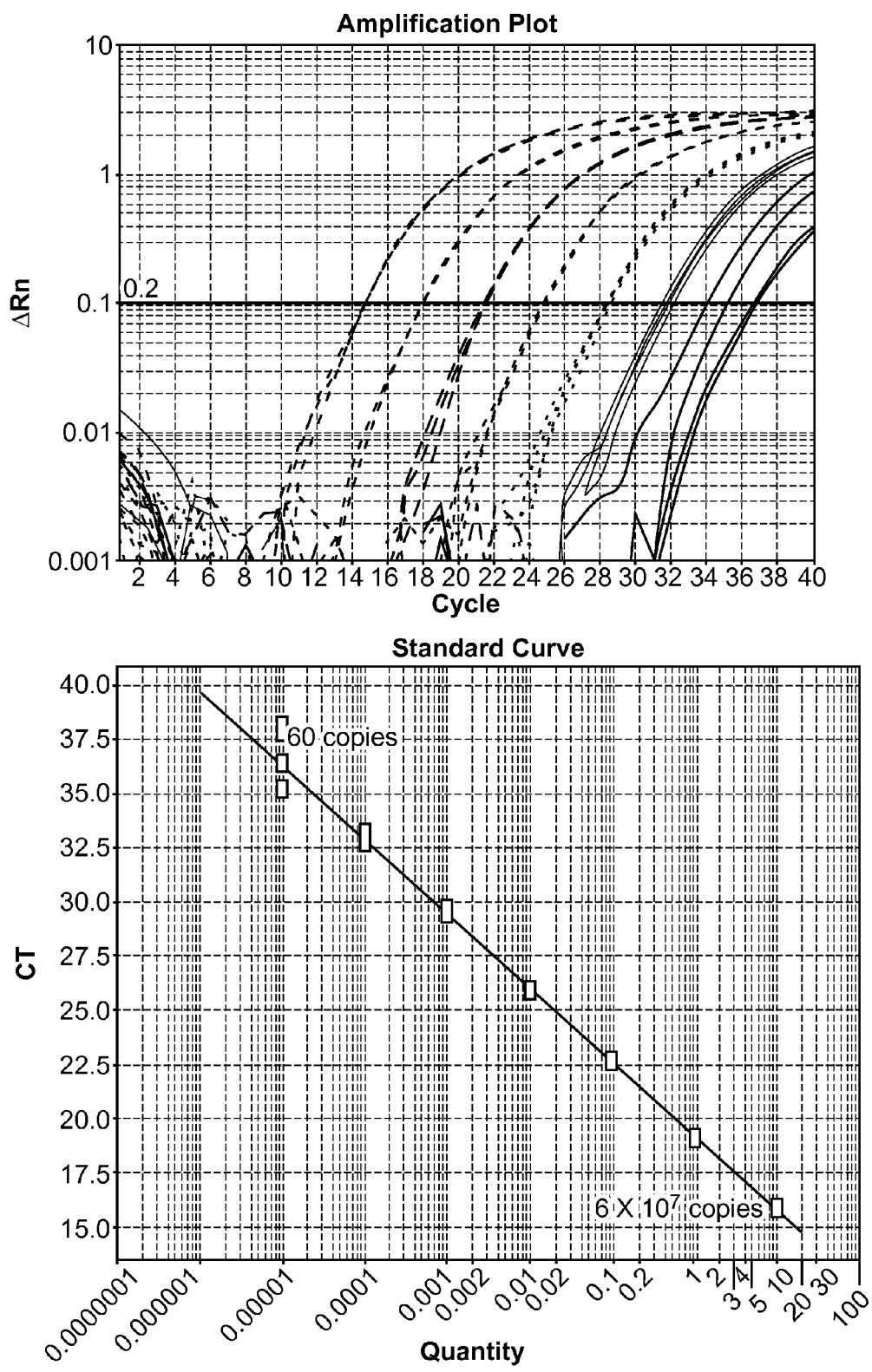
FIG. 8 graphically represents the sensitivity and linear dynamic range of the methods according to the embodiments of the present teachings.

As can be seen in FIG. 8, the titration of the synthetic template pool ranging from 6×10$^7$ to 60 copies in the ligation reaction showed at least a 6-log linear dynamic range and limit of detection of 60 copies that is distinguishable from the no template reaction.

Figure 9:
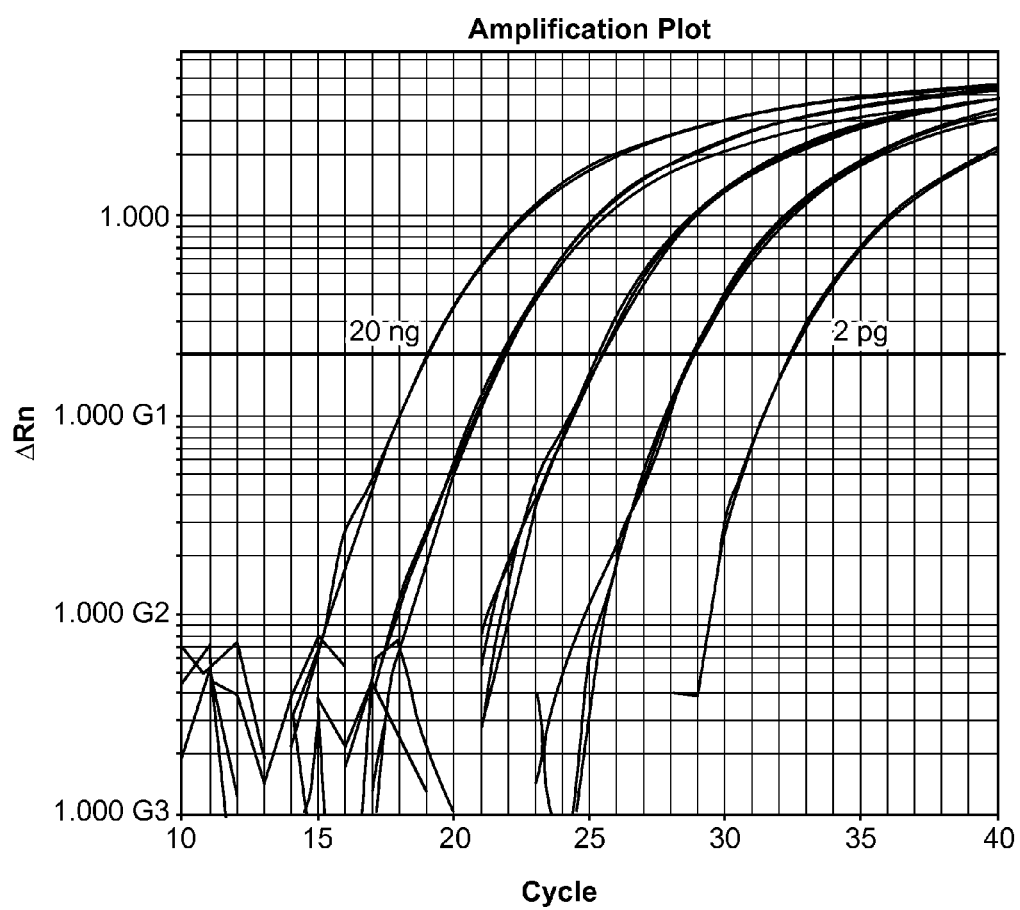
FIG. 9 shows an amplification plot of the expression level of hsa-let7a in total RNA and a sample titration response according to embodiments of the present teachings.

As can be seen in FIG. 9, the amplification plot shows the expression level of hsa-let-7a in total RNA from human brain, and a sample titration response ranging from 20 ng to 2 pg total RNA in the ligation reaction.

Specificity of the reaction was evaluated with cross-reactivity experiments where an assay was tested with the intended miRNA as well as the unintended miRNA homolog with only a single mismatch. The data showed minimal cross-reactivity for the hsa-let-7b TaqMan® assay with the hsa-let-7c template and the hsa-let-7c TaqMan® assay with the hsa-let-7b template. The sequence alignment is shown in Table 1 below for hsa-let-7b and hsa-let-7c (the variable nucleotides are shown in bold):

TABLE 1

| Sequence | Assay | Template | Cross-reactivity |
|---|---|---|---|
| hsa-let-7b:<br>UGAGGUAGUAGGUUGUGUGGUU<br>(SEQ ID NO: 1) | let-7b | let-7c | 0% |
| hsa-let-7c:<br>UGAGGUAGUAGGUUGUAUGGUU<br>(SEQ ID NO: 2) | let-7c | let-7b | 0.70% |

Figure 10:
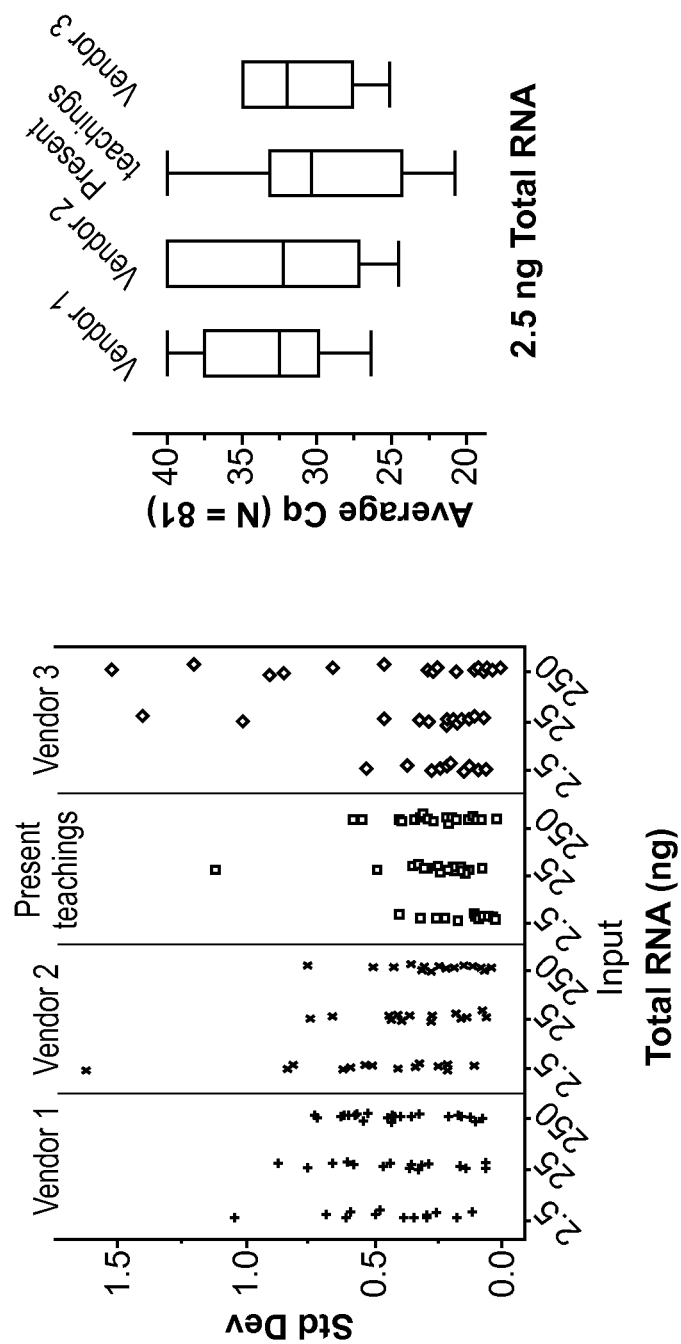
FIG. 10 graphically represents the sensitivity of the present methods relative to other methods.

As can be seen in FIG. 10, miRNA detection data using the assays and methods described herein were compared to miRNA detection methods from one internal source (Vendor 2) and two external sources (Vendors 1 and 3). Each method was performed according to the product specifications and guidelines. The greatest sensitivity was obtained using the methods according to the present teachings relative to the other methods as observed with 2.5 ng total RNA (right plot), with the least amount of variation (left plot).

Example 2: miRNA Analysis Using Dual-End Ligation-Based RT-qPCR (2-Step Method)

Two-step methods were performed essentially as described in Example 1, except that either the ligation and RT steps or the RT and pre-amplification steps were combined.

Figure 11:
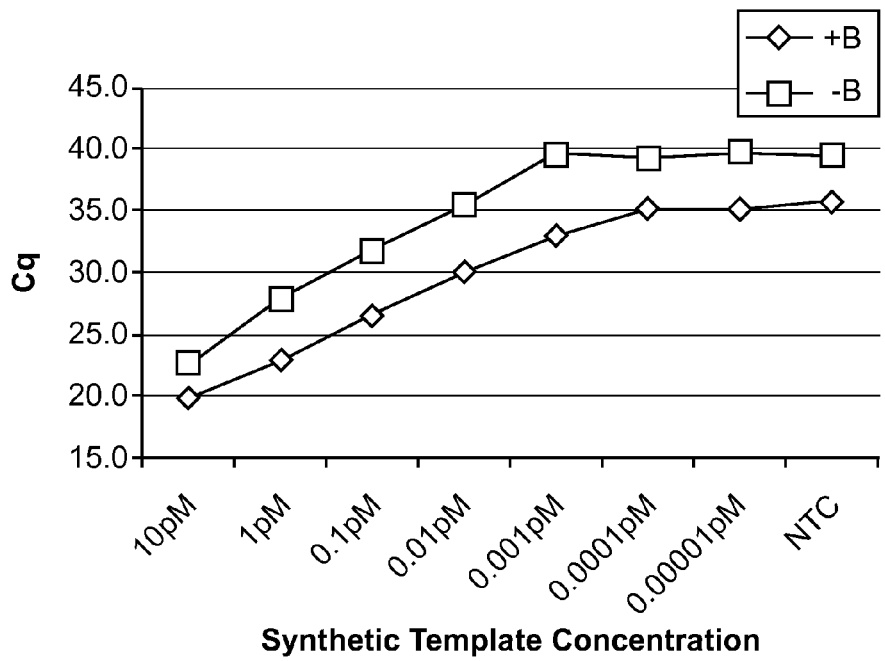
FIG. 11 graphically represents the linear dynamic range and sensitivity of a combined ligation/RT 2-step method according to embodiments of the present teachings.

The "2-in-1" combined ligation/RT method was performed by combining the miRNA with the following components: 5' ligation adaptor, 5' ligation splint, 3' ligation adaptor, 3' ligation splint, universal RT/reverse primer, T4 ligase, reaction buffer, SuperScript® III, and nuclease-free water. Pre-amplification and PCR were performed as in Example 1 with the ligation-RT product. As can be seen in FIG. 11 in the combined ligation/RT 2-step method, the titration of the synthetic template showed at least a 4- to 5-log linear dynamic range using an hsa-let-7a assay with blocking oligonucleotide (solid diamonds) or without blocking oligonucleotides (solid squares).

Figure 12:
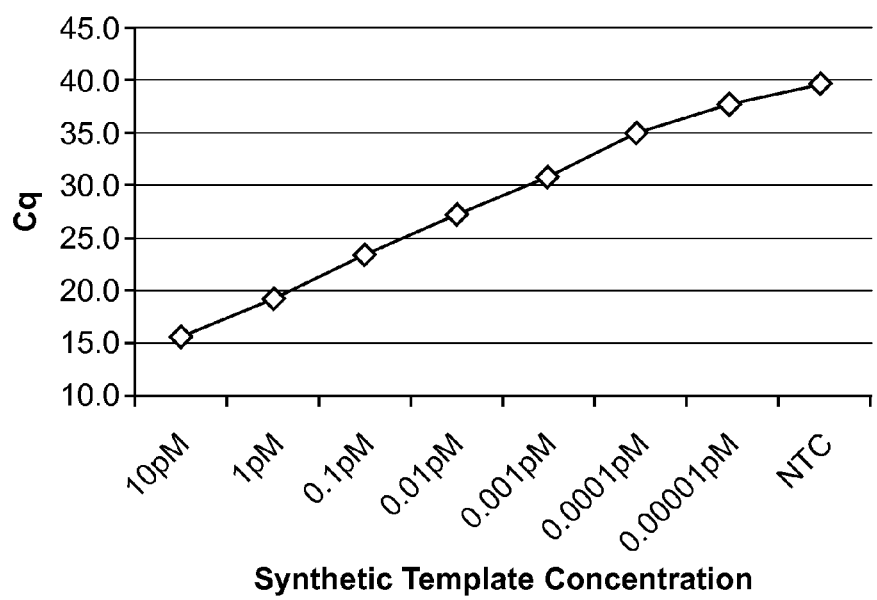
FIG. 12 graphically represents the linear dynamic range and sensitivity of a combined RT/pre-amplification 2-step method according to embodiments of the present teachings.

The "2-in-1" combined RT/pre-amp method was performed by combining the ligation product (ligation reaction as in Example 1) with the following components: universal forward primer, universal RT/reverse primer, SuperScript® III, reaction master mix, and nuclease-free water. PCR was performed as in Example 1 with the RT/pre-amp product. As can be seen in FIG. 12 in the combined RT/pre-amplification 2-step method, the titration of the synthetic template showed at least a 6-log linear dynamic range using an hsa-let-7a assay.

Example 3: miRNA Analysis Using Dual-End Ligation-Based RT-qPCR (1-Step Method)

Figure 13:
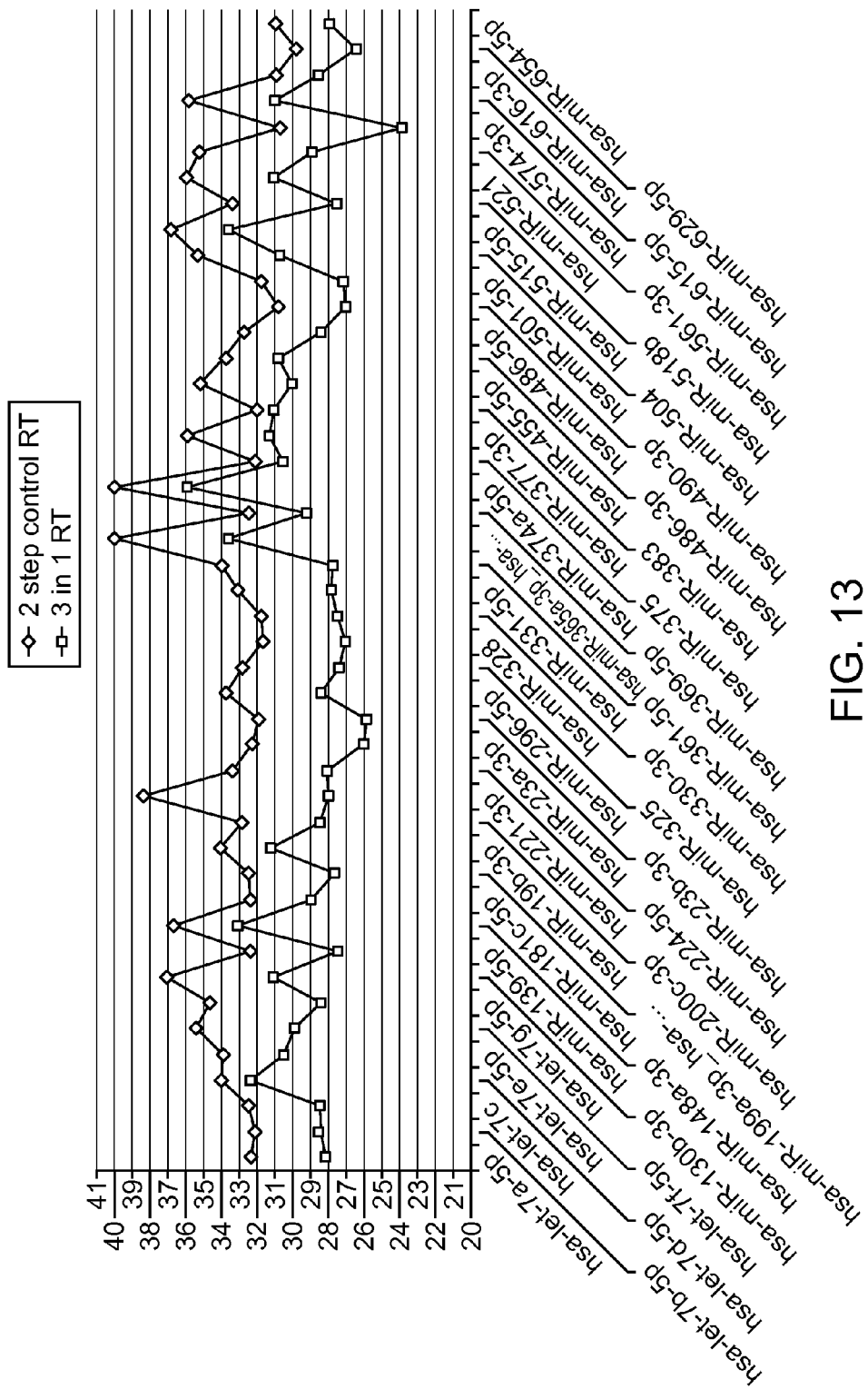
FIG. 13 graphically represents a comparison of the 3-in-1 combined method (i.e., combined ligation, extension (RT), and pre-amp/amplification; squares) and a two-step control (diamonds) according to embodiments of the present teachings.

A "3-in-1" method was performed by combining the miRNA with the following components: a 5' ligation adaptor, a 5' ligation splint, a 3' ligation adaptor, a 3' ligation splint, universal forward primer, universal RT/reverse primer, ligase (T4 ligase), reverse transcriptase (SuperScript® III) and AmpliTaq® Gold DNA polymerase. The reaction was stopped after RT by heating the mixture to 99° C. for 10 minutes. For comparison, a separate ligation and reverse transcription protocol (according to standard methods) was used as a control (FIG. 13, diamonds) to compare to the performance of the 3-in-1 method (FIG. 13, squares) using 45 miRNA templates. As can be seen in FIG. 13, both methods are comparable.

Figure 14:
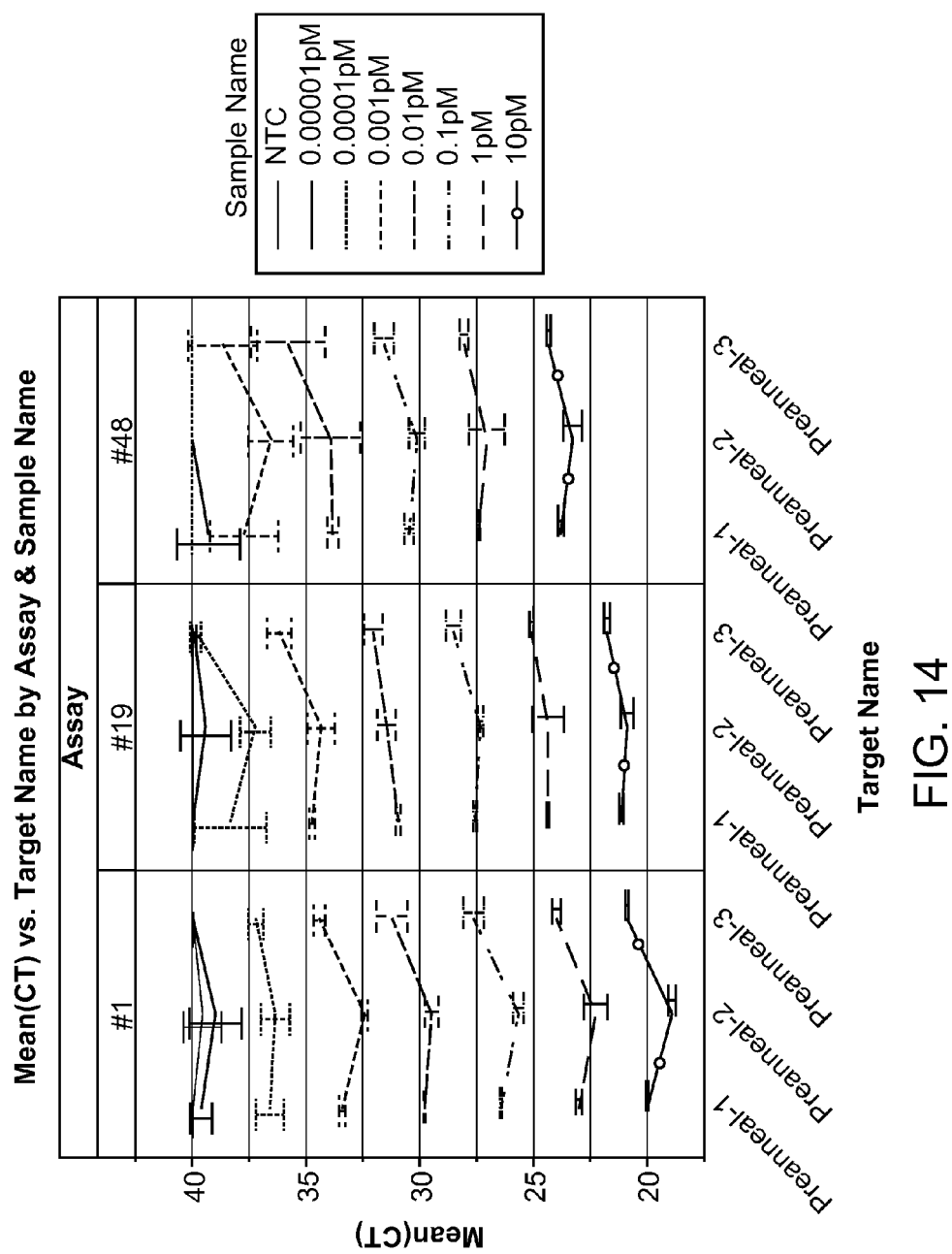
FIG. 14 graphically represents the sensitivity of the 3-in-1 combined method according to embodiments of the present teachings showing Ct vs. assay.

Serial dilutions of 48 template miRNAs were used to test the 3-in-1 method for sensitivity and dynamic range (see, FIG. 14). Pre-amp #1, 2, 3 as labeled along the x-axis indicates the different amount of universal RT/reverse primers included in the 3-in-1 reaction. A concentration of 0.5 µM of RT/reverse primer performs the best. The linear dynamic range of the 3-in-1 method has a 6- to 7-log linear dynamic range.

Example 4: Selective Blocking of Background Amplification Using Blocking Oligonucleotides The universal ligation adaptor sequences facilitate the synthesis of cDNA in RT and pre-amplification of cDNA in PCR using universal primers. To drive the ligation of ligation adaptors to miRNA, an excess amount of ligation adaptors are used; therefore, ligation between the two ligation linkers may be produced as a non-specific background by-product in the methods disclosed herein. This background compromises the detection of low abundant transcripts in both qPCR and NGS analysis and detection. To reduce the background, blocking oligonucleotides were developed to selectively suppress the amplification of the adaptor-adaptor by-product in the pre-amplification step. DNA oligonucleotides labeled at the 5' or 3' end with MGB, 2'-O-methyl RNA and sequence-targeted amplification restrictive (STAR) blockers were used in pre-amplification reactions (see FIG. 15). The addition of such blocking oligonucleotides was found to dramatically reduce background amplification and increase sensitivity of miRNA detection by qPCR with TaqMan® qPCR assays. Application of blocking oligonucleotides in library preparation of next-generation sequencing (NGS) for small RNA analysis is expected to greatly reduce the background and increase the proportion of sequence analysis of miRNA and the effective numbers of coverage for miRNA sequences.

Figure 16:
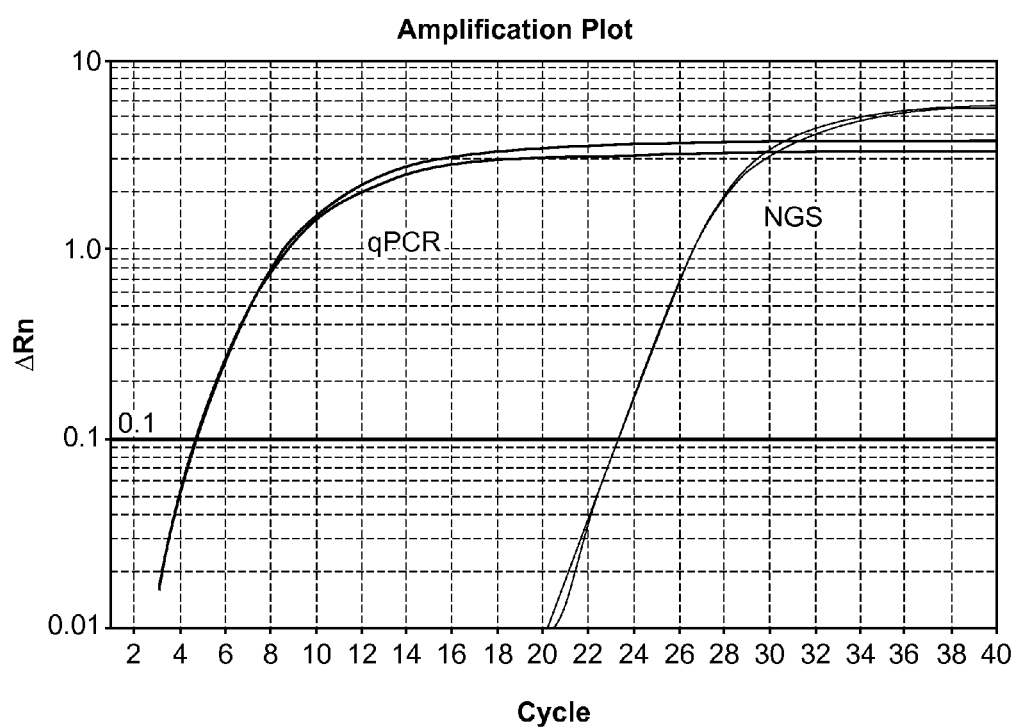
FIG. 16 graphically represents an amplification plot showing background adaptor-adaptor by-product after amplification using quantitative PCR (qPCR, left-most curve) or next-generation sequencing (NGS, right-most curve).

The dual-end ligation mRNA analysis was performed essentially as described in Example 1. As can be seen in FIG. 16, an excess amount of background adaptor-adaptor by-product was generated in qPCR (left-most curve) and next-generation sequencing (right-most curve). The ΔCt of target miRNA and background by-product was about 18, which translates into more than 100,000-fold more background was introduced in the process.

Figure 17:
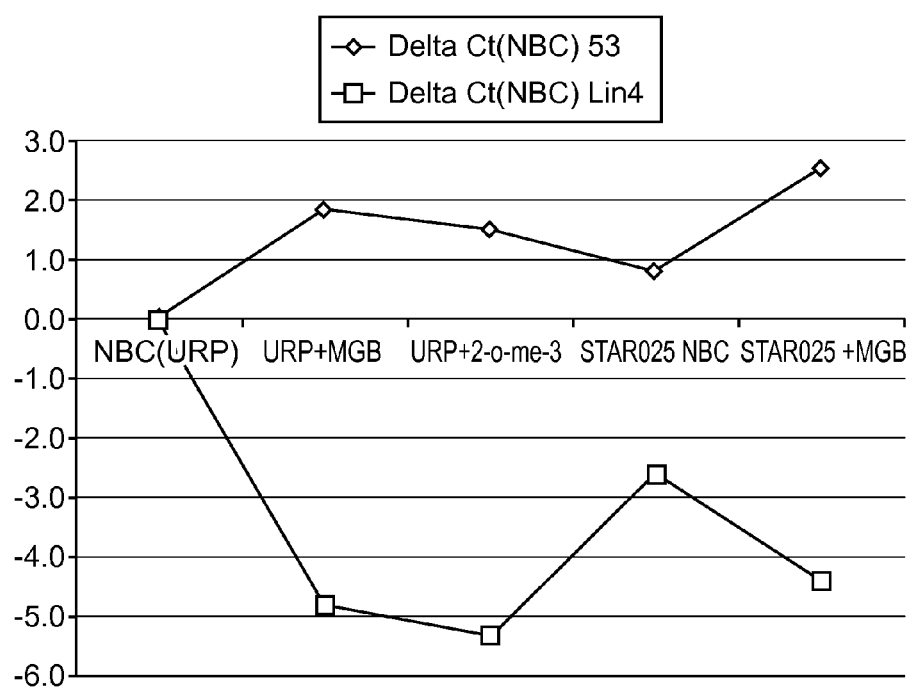
FIG. 17 graphically represents qPCR quantification of the effect of blocking oligonucleotides on background adaptor-adaptor by-product and target miRNA amplification.

As can be seen in FIG. 17, an artificial background (53) or C. Lin 4 was mixed with 5' and 3' ligation adaptors at a ratio of 10,000:1. Blocking oligonucleotides were added during the pre-amplification step. The ΔCt of samples with or without blockers was compared. The upper line (solid diamonds) represents the background Ct shift—the higher the shift, the better for background reduction. The bottom line (solid squares) shows the Ct shift with blocking oligonucleotides—the lower the shift, the better for improving the sensitivity.

Figure 18:
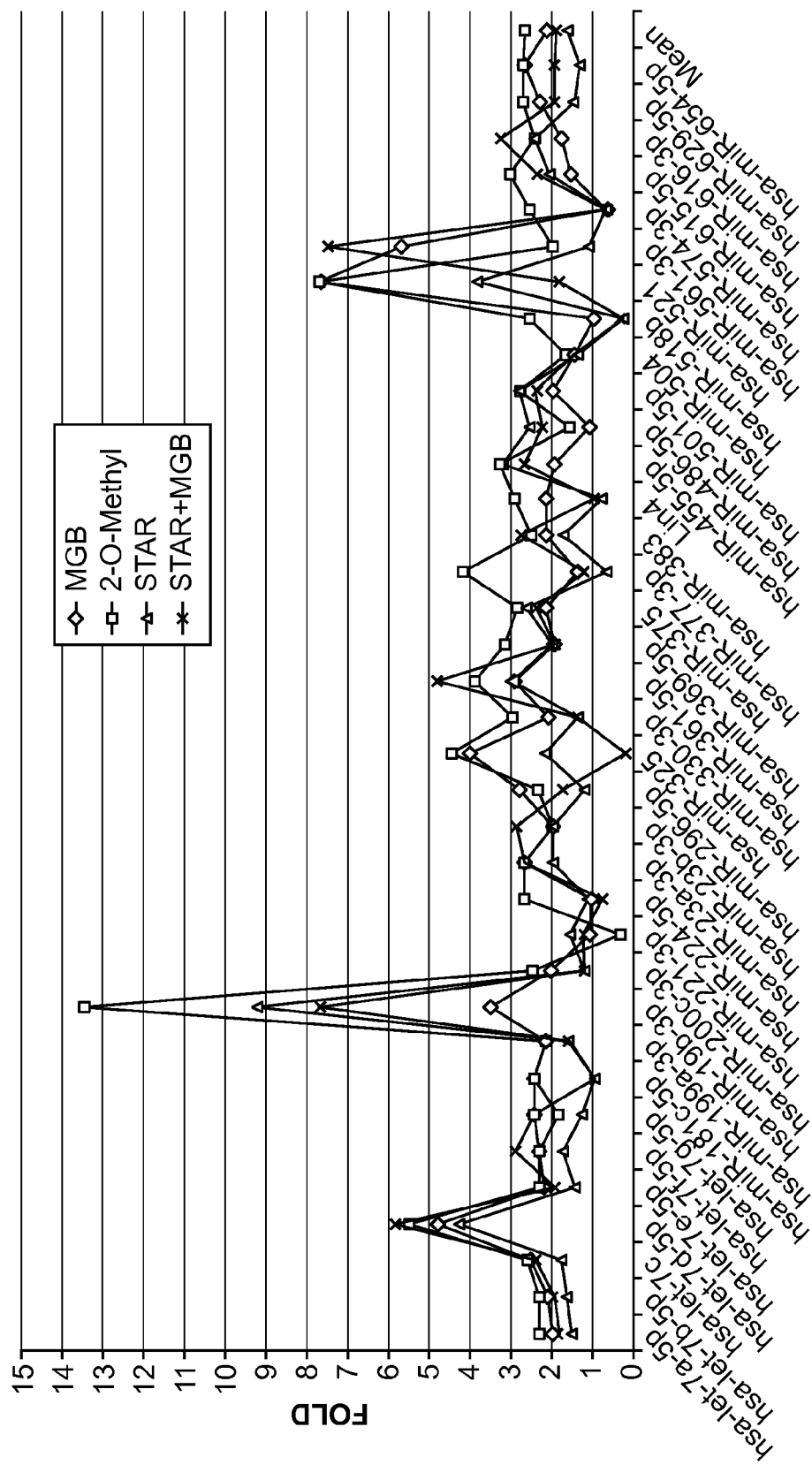
FIG. 18 graphically represents the increase in sensitivity of qPCR detection of target miRNA using various blocking oligonucleotides: 3'-MGB blocking oligonucleotide (diamond line), 2'-O-methyl RNA blocking oligonucleotide (square line), STAR URP blocking oligonucleotide (triangle line), and STAR URP+MGB blocking oligonucleotide (x-line).
Figure 19:
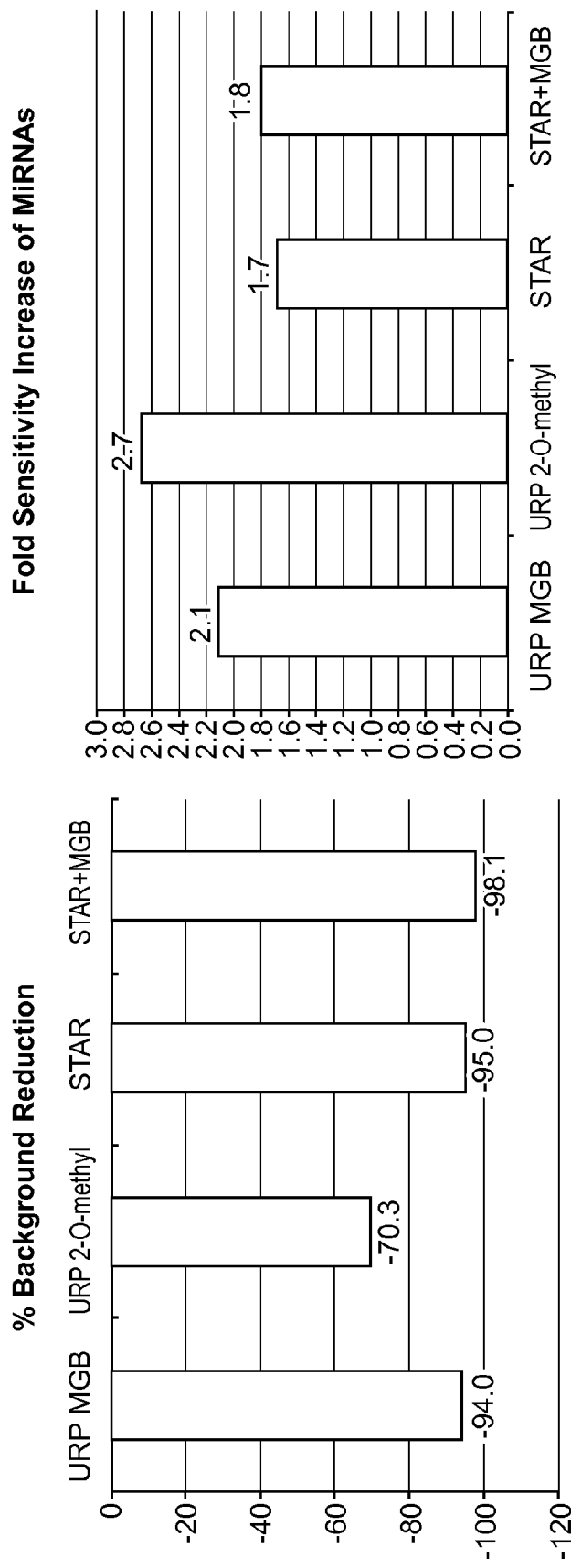
FIG. 19 graphically represents the percent reduction in background adaptor-adaptor by-product (left plot) and the fold increase in sensitivity (right plot) using blocking oligonucleotides in qPCR amplification.

FIGS. 17-18 show that blocking oligonucleotides increase the sensitivity of qPCR detection through the reduction of background in biological samples. Human brain total RNA was used in the dual-end ligation assay essentially as described in Example 1. Three different blockers (3'-MGB blocking oligonucleotide, 2'-O-methyl RNA blocking oligonucleotide, and STAR blocking oligonucleotide) were added during pre-amplification. qPCR was performed using 45 TaqMan® assays against 45 miRNAs. FIG. 18 shows the fold increase in sensitivity of each miRNA assay with each blocking oligonucleotide. FIG. 19, left panel shows the percent reduction of background by-product amplification using the blocking oligonucleotides. FIG. 19, right panel shows the average fold increase in sensitivity of detection across the 45 miRNA assays.

Figure 20:
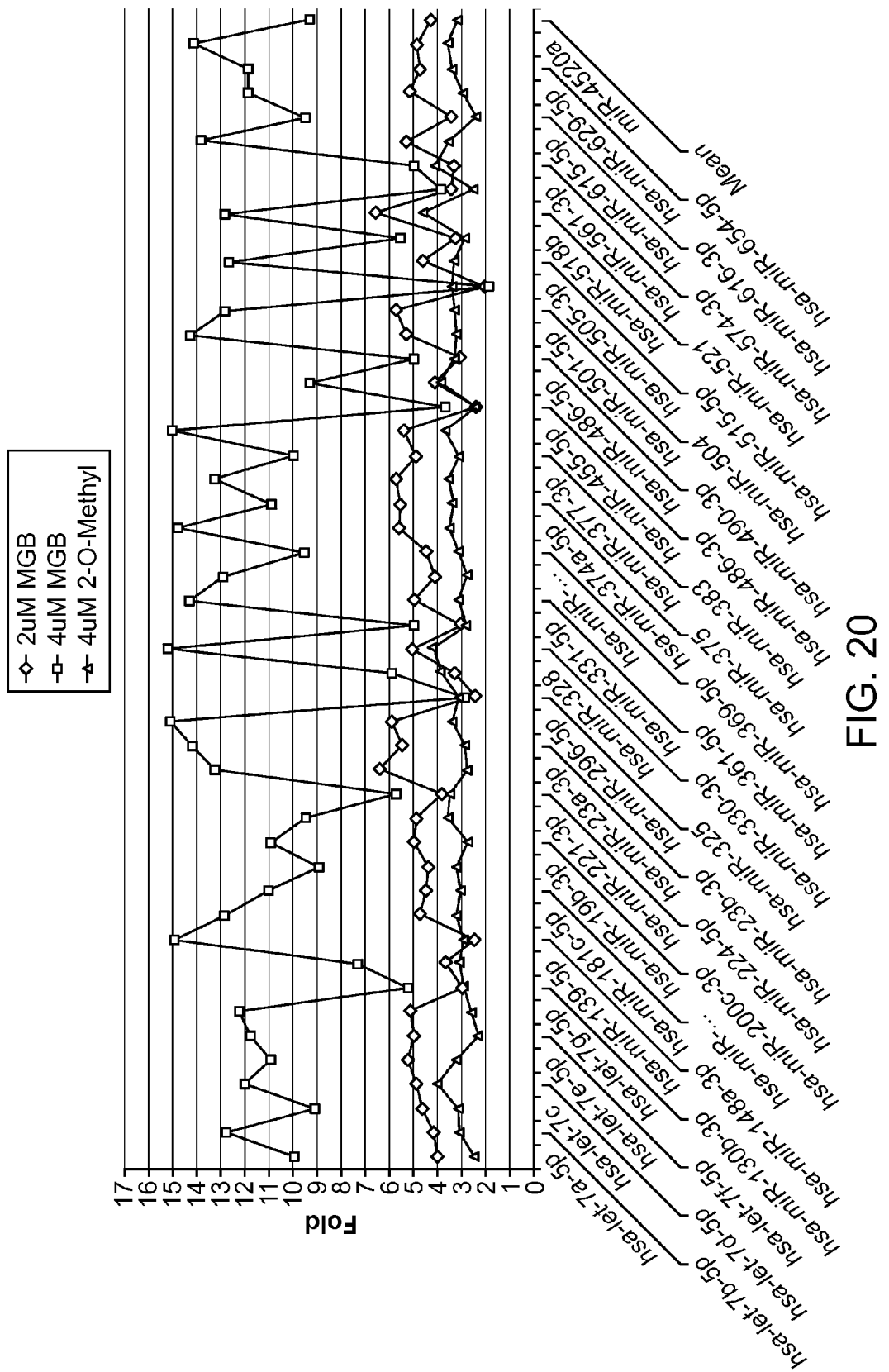
FIG. 20 graphically represents the reduction of background adaptor-adaptor by-product and increase in sensitivity of detection of miRNAs in next-generation sequencing (NGS) using various blocking oligonucleotides: 2 μM 3'-MGB blocking oligonucleotide (diamond line), 4 μM 3'-MGB blocking oligonucleotide (square line), and 4 μM 2'-O-methyl RNA blocking oligonucleotide (triangle line).
Figure 21:
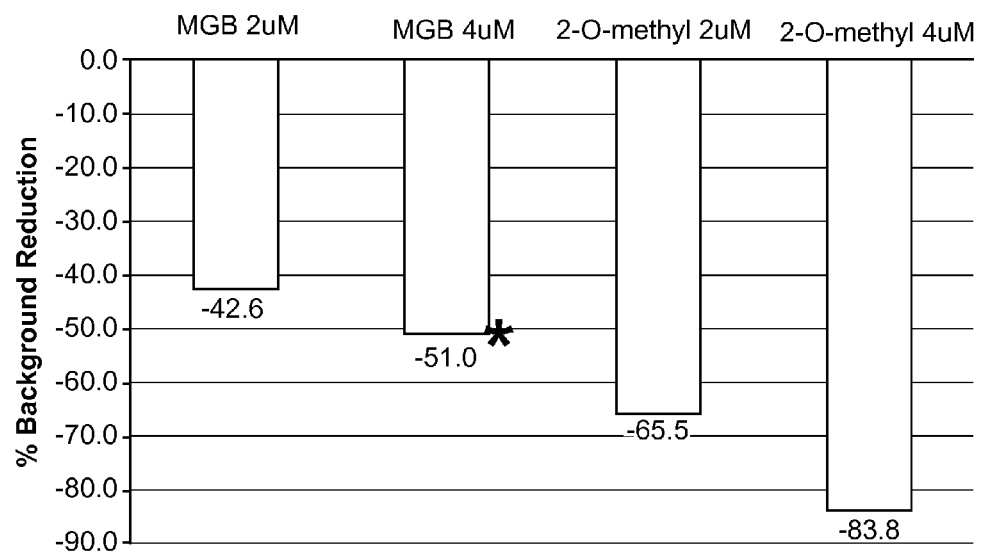
FIG. 21 graphically represents the percent reduction in background adaptor-adaptor by-product using blocking oligonucleotides in NGS analysis of miRNA.
Figure 22:
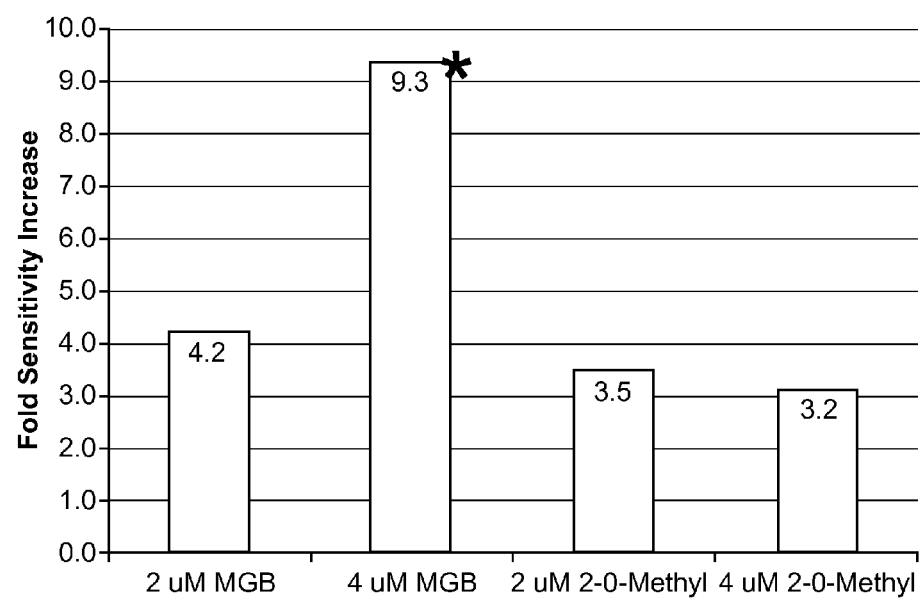
FIG. 22 graphically represents the fold increase in sensitivity using blocking oligonucleotides in NGS analysis of miRNA.

FIGS. 20-22 show that the blocking oligonucleotides increase the sensitivity of next generation sequencing through reduction in background by-product formation in biological samples. Human brain total RNA was used in the NGS RNASeq workflow according to manufacturer's instructions. Two different blocking oligonucleotides (3'-MGB blocking oligonucleotide and 2-O-methyl RNA blocking oligonucleotide) at either 2 μM or 4 μM were added during the cDNA library pre-amplification. qPCR was performed using 48 TaqMan® assays against 48 miRNAs. FIG. 20 shows the increase in fold sensitivity of each miRNA with the various blocking oligonucleotides. FIG. 21 shows the percent reduction in background by-product formation with each blocking oligonucleotide. FIG. 22 shows the average fold increase in sensitivity of detection across the 48 miRNA assays.

Both dual-end ligation miRNA analysis using qPCR and next generation sequencing analysis of miRNA used blocking oligonucleotides to reduce ligated adaptor-adaptor by-product formation. For the qPCR analysis, both the MGB blocking oligonucleotide and STAR blocking oligonucleotide showed higher background reduction (>90%), but the 2'-O-methyl RNA blocking oligonucleotide showed a higher fold increase in sensitivity (mean=2.7 fold). However, for the next generation sequencing analysis, the 2'-O-methyl RNA blocking oligonucleotide showed the higher reduction in background, whereas the MGB blocking oligonucleotide (4 μM) showed the highest increase in sensitivity (mean=9 fold) for target miRNA detection.

Example 5: miRNA Analysis Using Two-Ended Extension Based Assay

Adaptor, primer, and synthetic miRNA oligonucleotides were purchased from Integrated DNA Technologies (IDT, Coralville, Iowa). Taqman® assays were obtained from Applied Biosystems® Custom Gene Expression Laboratory.

Poly A Tailing and Reverse Transcription Reactions

First strand cDNA was generated by a one-step poly A tailing and reverse transcription (RT) reaction. The polyadenylation and RT reaction was performed by combining 2 μl 5×RT buffer, 1 μl 200 U/μl SuperScript™ III, 3 μl nuclease-free water, and 4 μl synthetic miRNA templates ranging from 60 to 60 million copies in a total reaction volume of 10 μl. The reaction mix was mixed, spun briefly, and incubated in a thermal cycler at 37° C. for 60 minutes, 95° C. for 5 min, 4° C. hold.

Ligation Reaction

The ligation reaction was performed to ligate the cDNA to the ligation adaptor in the presence of ligation splint oligo with semi-degenerate overhang. The ligation reaction was performed by combining the following components: 1.5 μl 10× Adaptor Mix, 1.5 μl 10× Ligation Buffer, 1.5 μl 10× Ligation Enzyme, 0.5 μl nuclease-free water, and 10 μl cDNA from the poly A tailing RT reaction for a total ligation reaction volume of 15 μl. The ligation reaction was mixed, spun briefly, and incubated in a thermal cycler at 25° C. for 60 minutes, 65° C. for 10 min, 4° C. hold.

Preamplification Reaction

Preamplification (preamp) is an optional step to increase sensitivity for detection. The pre-amp reaction was performed by combining the following components: 25 μl 2× TaqMan® PreAmp Master Mix, 2.5 μl 20× PreAmp Universal Primers, 7.5 μl nuclease-free water, and 15 μl ligated cDNA from the ligation reaction for a total preamp reaction of 50 μl. the pre-amp reaction was mixed, spun briefly, and incubated in a thermal cycler at 95° C. for 10 min, followed by 12 cycles of (95° C. for 15 sec, 60° C. for 2 min), followed by 99° C. for 10 min, and a 4° C. hold.

PCR

Real-time PCR (qPCR) was performed for the detection of miRNAs. The ligation reactions or preamp reactions were diluted at 1:4, 1:10, 1:50, or 1:100 in nuclease-free water. The PCR reaction was prepared by combining the following components: 10 μl 2× TaqMan® Universal Master Mix II, 1 μl 20× TaqMan® Assay, 4 μl nuclease-free water, and 5 μl diluted ligation or preamp reaction for a total of 20 μl PCR volume. The PCR reaction was mixed and spun briefly. The reactions were run with a real-time PCR system, such as ABI PRISM® 7900HT Sequence Detection System or ViiA™ 7 Real-Time PCR System. The data was analyzed according to the instrument specifications and guidelines.

Figure 23:
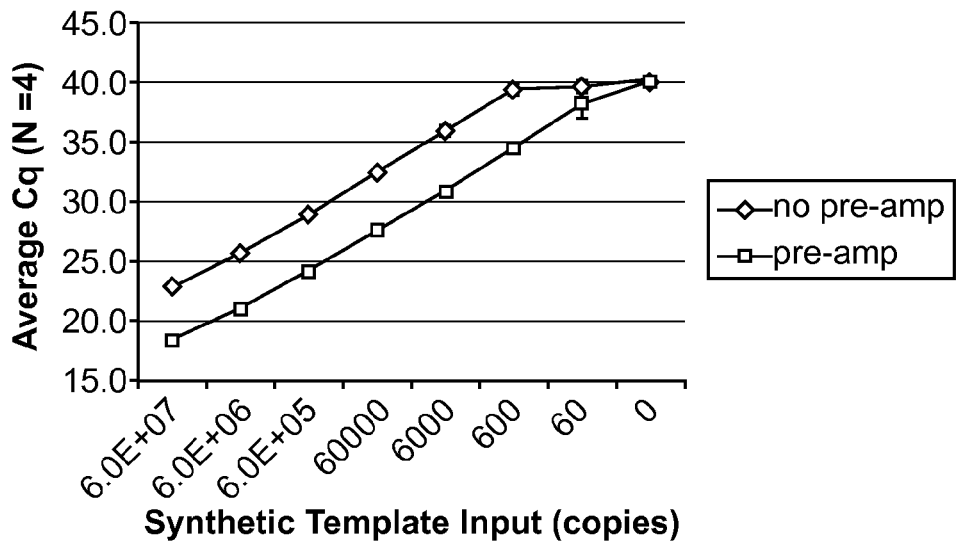
FIG. 23 graphically represents the linear dynamic range and sensitivity of a combined polyadenylation/RT 2-step method followed by a cDNA ligation reaction, with (square line) or without (diamond line) a pre-amplification step according to embodiments of the present teachings.

As can be seen in FIG. 23, titration of the synthetic miRNA template ranging from $6 \times 10^7$ to 60 copies in the polyadenylation/RT reaction showed at least a 6-log linear dynamic range with detection sensitivity of 60 copies. Background signal was not an issue as shown in the no template reactions. Inclusion of a pre-amplification step enhanced detection sensitivity (see FIG. 23, closed squares).

This miRNA analysis method was also performed with an oligonucleotide blocker present in the ligation reaction. The oligonucleotide blocker has a stem-loop structure and a poly(A) containing single-stranded overhang portion at its 3' end as depicted in FIG. 15 D. The blocker can hybridize with any universal RT primer which is unannealed or unextended. Accordingly, the oligonucleotide blocker would suppress ligation of the ligation adaptor to free universal RT primer.

Figure 24:
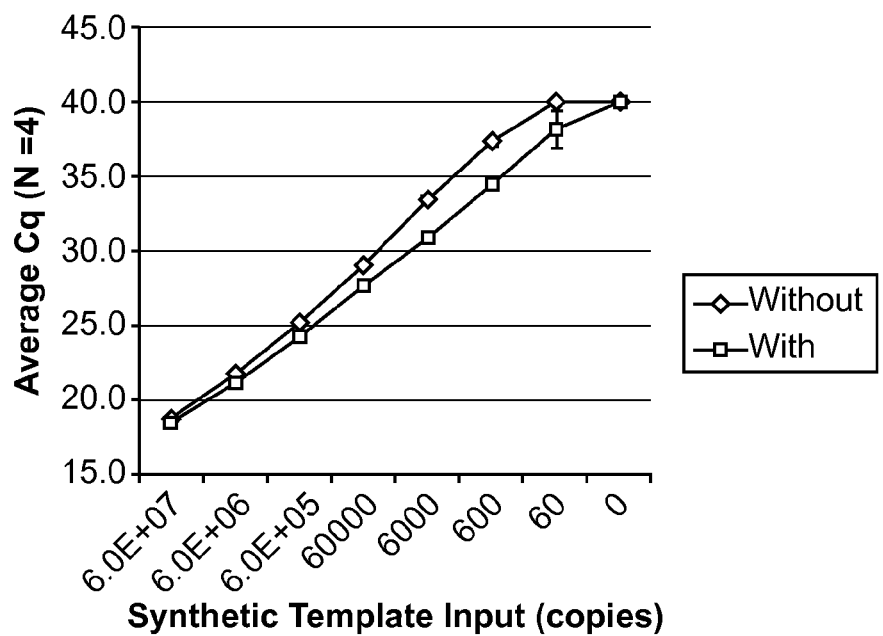
FIG. 24 graphically represents the increase in sensitivity of qPCR detection of target miRNA with a blocker oligonucleotide (square line) in the ligation reaction compared to the ligation reaction without the blocker oligonucleotide (diamond line).

As can be seen in FIG. 24, use of an oligonucleotide blocker in the ligation reaction increased amplification efficiency for low copy number by reducing non-specific ligation by-product.

What is claimed is:

1. A method for detecting a mature small RNA, the method comprising:
providing a sample comprising a mature small RNA;
polyadenylating the 3' end of the mature small RNA;
reverse transcribing the polyadenylated mature small RNA using a universal reverse transcription primer, thereby forming a cDNA of the mature small RNA, wherein the universal reverse transcription primer comprises a poly(T) portion and a tail portion, wherein the tail portion comprises a universal reverse primer portion;
ligating a universal ligation adaptor to the 3' end of the cDNA, whereby a cDNA ligation product is formed, wherein the universal ligation adaptor comprises a ligation splint portion and further comprises a stem-loop structure;
amplifying the cDNA ligation product using a universal forward and reverse primer pair to form an amplification product; and
detecting the amplification product with a probe specific for the mature small RNA, wherein the ligating and the amplifying occur during overlapping intervals in the same reaction vessel.

2. The method of claim 1, wherein the polyadenylating step and the reverse transcribing step occur during overlapping intervals in the same reaction vessel.

3. The method of claim 1, wherein the universal ligation adaptor is selected from the group consisting of a DNA oligonucleotide and a DNA oligonucleotide comprising at least one blocking agent.

4. The method of claim 3, wherein the blocking agent is selected from the group consisting of 2'-0-methyl, acridine, a minor groove binder (MGB), and an intercalating dye compound.

5. The method of claim 1, wherein the ligation splint portion comprises a 3' single-stranded overhang which hybridizes with the 3' region of the cDNA.

6. The method of claim 5, wherein the 3' single-stranded overhang comprises about 3 to about 6 nucleotide bases.

7. The method of claim 1, wherein the ligation splint portion is a semi-degenerate.

8. The method of claim 7, wherein the semi-degenerate ligation splint portion comprises a 3' terminal region comprising about 3 to about 6 degenerate nucleotide bases that hybridizes with the 3' end of the cDNA and a 5' region that hybridizes with the 5' end of the universal ligation adaptor.

9. The method of claim 1, further comprising adding a blocking oligonucleotide to the ligating and/or amplifying step.

10. The method of claim 9, wherein the blocking oligonucleotide is selected from the group consisting of a 3'-MGB blocking oligonucleotide, a 5'-MGB blocking oligonucleotide, a 2'-O-methyl blocking oligonucleotide, a 3'-acridine blocking oligonucleotide, a 5'-acridine blocking oligonucleotide, a STAR blocking oligonucleotide, and a blocking oligonucleotide comprising a poly(A) sequence.

11. The method of claim 1, wherein the universal ligation adaptor comprises a second portion complementary to the ligation splint portion.

12. The method of claim 11, wherein the complementarity between the second portion and the ligation splint portion of the universal ligation adaptor is located within the stem of the stem-loop structure.

13. The method of claim 1, wherein the universal ligation adaptor comprises at least one blocking agent at the 3' end.

14. The method of claim 13, wherein the blocking agent is selected from the group consisting of 2'-0-methyl, acridine, a minor groove binder (MGB), and an intercalating dye compound.

15. The method of claim 1, wherein the universal ligation adaptor is a DNA-RNA hybrid oligonucleotide.

16. The method of claim 1, wherein the universal ligation adaptor comprises a forward primer binding site.

17. The method of claim 1, wherein the forward primer binding site is located within the stem of the stem-loop structure.

18. The method of claim 1, wherein the forward primer binding site is located within the loop of the stem-loop structure.

19. The method of claim 1, wherein the forward primer binding site is located within some portion of both the stem and loop of the stem-loop structure.

* * * * *